US011344872B2

(12) United States Patent
Chang et al.

(10) Patent No.: US 11,344,872 B2
(45) Date of Patent: May 31, 2022

(54) METAL COMPLEX, METHOD FOR PRODUCING SAME, AND METHOD FOR PRODUCING GAMMA-LACTAM COMPOUND USING SAME

(71) Applicants: INSTITUTE FOR BASIC SCIENCE, Daejeon (KR); KOREA ADVANCED INSTITUTE OF SCIENCE AND TECHNOLOGY, Daejeon (KR)

(72) Inventors: Sukbok Chang, Daejeon (KR); Seung Youn Hong, Daejeon (KR); Yoon Su Park, Daejeon (KR); Yeongyu Hwang, Daejeon (KR); Yeong Bum Kim, Daejeon (KR)

(73) Assignees: INSTITUTE FOR BASIC SCIENCE, Daejeon (KR); KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 0 days.

(21) Appl. No.: 16/959,880

(22) PCT Filed: Jan. 2, 2019

(86) PCT No.: PCT/KR2019/000040
§ 371 (c)(1),
(2) Date: Jul. 2, 2020

(87) PCT Pub. No.: WO2019/135600
PCT Pub. Date: Jul. 11, 2019

(65) Prior Publication Data
US 2020/0330969 A1  Oct. 22, 2020

(30) Foreign Application Priority Data

Jan. 2, 2018  (KR) .................. 10-2018-0000449
Dec. 28, 2018 (KR) .................. 10-2018-0172885

(51) Int. Cl.
C07F 15/06    (2006.01)
C07F 17/02    (2006.01)
B01J 31/22    (2006.01)
C07D 207/267  (2006.01)
C07D 209/46   (2006.01)
C07D 209/52   (2006.01)
C07D 209/54   (2006.01)
C07D 209/56   (2006.01)
C07D 209/70   (2006.01)
C07D 403/04   (2006.01)
C07D 405/04   (2006.01)
C07D 409/04   (2006.01)
C07J 43/00    (2006.01)

(52) U.S. Cl.
CPC ...... *B01J 31/2295* (2013.01); *C07D 207/267* (2013.01); *C07D 209/46* (2013.01); *C07D 209/52* (2013.01); *C07D 209/54* (2013.01); *C07D 209/56* (2013.01); *C07D 209/70* (2013.01); *C07D 403/04* (2013.01); *C07D 405/04* (2013.01); *C07D 409/04* (2013.01); *C07F 17/02* (2013.01); *C07J 43/003* (2013.01); *B01J 2231/60* (2013.01)

(58) Field of Classification Search
CPC ........................... B01J 31/183; B01J 31/2295; B01J 2531/821; B01J 2531/822; B01J 2351/827; B01J 2351/845; C07F 15/0033; C07F 15/0046; C07F 15/0073; C07F 15/06; C07F 17/02
See application file for complete search history.

(56) References Cited

FOREIGN PATENT DOCUMENTS

CN  101503487 A  8/2009
JP  58-192874 A  11/1983

OTHER PUBLICATIONS

Allu et al., Ruthenium-Catalyzed Synthesis of Isoquinolones with 8-Aminoquinoline as a Bidentate Directing Group in C—H Functionalization, The Journal of Organic Chemistry, vol. 79, No. 9, pp. 3963-3972 (Year: 2014).*
Dayan et al., Synthesis and Characterization of Half-Sandwich Ruthenium Complexes Containing Aromatic Sulfonamides Bearing Pyridinyl Rings: Catalysts for Transfer Hydrogenation of Acetophenone Derivatives, European Journal of Inorganic Chemistry, vol. 2013, No. 18, pp. 3224-3232 (Year: 2013).*
Simal et al., Ruthenium Complexes Containing Diamine-Based Ligands as Catalysts for Insertion of Carbenes into O—H Bonds of Alcohols, Tetrahedron Letters, vol. 40, No. 1, pp. 63-66 (Year: 1999).*
International Search Report dated Apr. 5, 2019, in connection with corresponding International Patent Application No. PCT/KR2019/000040, citing the above references.
Chemical Abstract compounds, STN express, cited in NPL No. 1, 2017.
Brancatelli, G. et al., "Basicity and bulkiness effects of 1,8-diaminonaphthalene, 8-aminoquinoline and their alkylated derivatives on the different efficiencies of η5-C5H5 and η5-C5Me5 ruthenium precatalysts in allylic etherification reactions," New Journal of Chemistry, 2010, vol. 34, No. 12, pp. 2853-2860, cited in NPL No. 1.
Enquist, P.-A. et al., "ESI-MS Detection of Proposed Reaction Intermediates in the Air-Promoted and Ligand-Modulated Oxidative Heck Reaction," The Journal of Organic Chemistry, 2006, vol. 71, No. 23, pp. 8779-8786, cited in NPL No. 1.

(Continued)

*Primary Examiner* — Brenda L Coleman
(74) *Attorney, Agent, or Firm* — Hauptman Ham, LLP

(57) ABSTRACT

The present invention relates to a novel metal complex, a method for producing same, and a method for producing a gamma-lactam compound using same, and the metal complex according to the present invention is used as a catalyst for producing a gamma-lactam compound and can efficiently produce a gamma-lactam compound with an excellent yield and excellent selectivity.

6 Claims, No Drawings

(56) References Cited

OTHER PUBLICATIONS

Hong, S. Y. et al., "Selective formation of gamma-lactams via C—H amidation enabled by tailored iridium catalysts," Science, Mar. 2, 2018, vol. 359, No. 6379, pp. 1016-1021, cited in NPL No. 1.
Korean Notice of Allowance dated Jun. 8, 2020, in connection with corresponding Korean Patent Application No. 10-2018-0172885.
Korean Office Action dated Mar. 10, 2020, in connection with corresponding Korean Patent Application No. 10-2018-0172885.
Hao-Jie Rong et al., "Synthesis of Gamma-Lactams by Mild, o-Benzoquinone-Induced Oxidation of Pyrrolidines Containing Oxidation-Sensitive Functional Groups," The Journal of Organic Chemistry, 2017, 82, 532-540, cited in NPL No. 6 and No. 7.
J. Caruano et al., "Biologically active Gamma-lactams: synthesis and natural sources," Organic & Biomolecular Chemistry, 2016, 14, 10134-10156, cited in NPL No. 6 and No. 7.
Jain, N. et al., "Oxidative Amidation in the Naphthalene Series," Synlett. 2015, vol. 26, No. 05, pp. 631-634, cited in NPL No. 6.

\* cited by examiner

METAL COMPLEX, METHOD FOR PRODUCING SAME, AND METHOD FOR PRODUCING GAMMA-LACTAM COMPOUND USING SAME

CROSS-REFERENCE TO RELATED APPLICATION

The present application is a national stage filing under 35 U.S.C § 371 of PCT application number PCT/KR2019/000040 filed on Jan. 2, 2019 which is based upon and claims the benefit of priorities to Korean Patent Application No. 10-2018-0000449, filed on Jan. 2, 2018 and Korean Patent Application No. 10-2018-0172885, filed on Dec. 28, 2018, in the Korean Intellectual Property Office, which are incorporated herein in their entireties by reference.

TECHNICAL FIELD

The present invention relates to a novel metal complex, a method of preparing the same, and a method of preparing a gamma-lactam compound using the same, and more particularly, to a novel metal complex allowing a gamma-lactam compound to be prepared from a dioxazol-one compound with excellent selectivity and yield, a method of preparing the same, and a method of preparing a gamma-lactam compound using the same.

BACKGROUND ART

The most preferred method of purifying hydrocarbon with low added value which is supplied in large quantities in petroleum or a renewable biomass source into a chemical material with high added value is a reaction of oxidizing a C—H bond using a catalyst.

Therefore, the reaction of oxidizing a C—H bond using a catalyst is regarded as being one of the most important reactions in chemistry, and a nitration reaction of an aliphatic compound having a C—H compound using a catalyst is a very important reaction which is most commonly used in various organic synthesis, medicines, and material chemistry.

An effective and general method for performing a C—N coupling reaction is to convert a nucleophilic amino functional group into an electrophilic nitrene having a much stronger reactivity in a C—H amidation reaction using a metal catalyst.

This reaction is very efficient and the related reactions have been studied by many researchers for a long time.

As an example, it is known by Breslow et al. that in the synthesis of oxathiazolidine catalyzed by Fe(III) or Rh(II), $ROSO_2N=IR'$ (iminoiodinanes) which is a reactive peroxide may serve as a sulfonylnitrene precursor, and thereafter, various methods related thereto have been studied.

However, C—H amidation has an unsolved problem for being applied to preparation of cyclic amides such as lactam which is very useful for a raw material and an intermediate in organic synthesis and a medicinal use, and the route thereof is also unclear.

The simplest precursor and the most important intermediate which may directly produce a cyclic amide compound is known as carbonylnitrene produced in an in-situ reaction.

Therefore, in principle, it is considered that in a catalytic reaction using a metal, the reaction proceeds through a main metal-nitrene intermediate and then a C—H bond is inserted to produce an aziheterocyclic compound corresponding thereto.

However, the main reason for not synthesizing a lactam compound by the C—H amidation reaction is that a metal-carbonylnitrene intermediate which is regarded as an intermediate is unstable and easily produce isocyanate by Curtius type rearrangement.

This instability is also accounted for as acyl azide as a synthesis precursor under photolysis, pyrolysis, and transition metal catalyst conditions.

Accordingly, acyl azide is inappropriate as an amide source of a C—H amidation reaction and a specific amide source is needed, and furthermore, a study on a catalyst for preparing a lactam compound with excellent selectivity and yield is also needed.

DISCLOSURE

Technical Problem

While trying to solve the problem described above, the present inventor found that a gamma-lactam compound may be prepared with excellent selectivity and yield by a novel metal complex having a specific functional group, thereby completing the present invention.

Therefore, an object of the present invention is to provide a novel metal complex, a method of preparing the same, and a method of preparing a gamma-lactam compound using the same.

Another object of the present invention is to provide a lactam compound prepared by the method of preparing a gamma-lactam compound.

Technical Solution

In one general aspect, a novel metal complex used as a catalyst for preparing a gamma-lactam compound is provided, which is represented by the following Chemical formula 1:

[Chemical Formula 1]

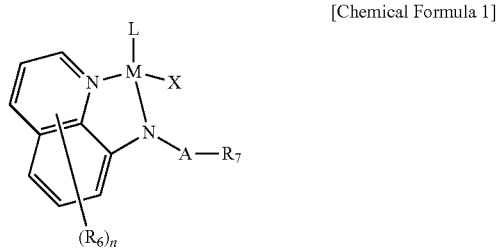

wherein
M is iridium, rhodium, ruthenium, or cobalt;
L is

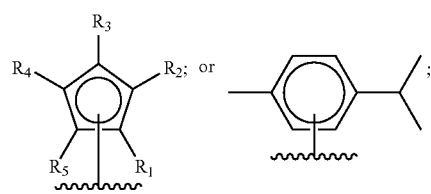

X is a halogen;
$R_1$ to $R_5$ are independently of one another hydrogen or (C1-C20)alkyl; and $R_6$ is a halogen, (C1-C20)alkyl, halo(C1-C20)alkyl, (C1-C20)alkoxy, (C6-C20)aryl, or (C3-C20)heteroaryl;

A is —CO— or —SO$_2$—;

$R_7$ is (C1-C20)alkyl, (C1-C20)alkoxy, (C6-C20)aryl, (C1-C20)alkyl(C6-C20) aryl, or —NR$_{11}$R$_{12}$;

$R_{11}$ and $R_{12}$ are independently of each other hydrogen or (C1-C20)alkyl; and n is an integer of 0 to 6.

Preferably, in Chemical Formula 1 according to an exemplary embodiment of the present invention, L may be

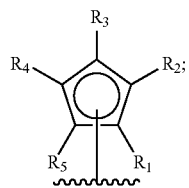

X may be Cl or Br; $R_1$ to $R_5$ may be independently of one another (C1-C20)alkyl; $R_6$ may be halo(C1-C20)alkyl or (C1-C20)alkoxy; and n may be an integer of 0 to 6.

Preferably, Chemical Formula 1 according to an exemplary embodiment of the present invention may be represented by the following Chemical Formula 2:

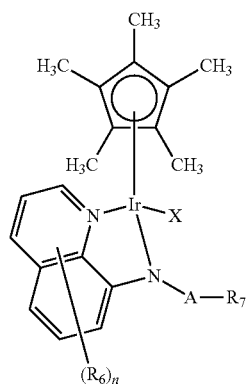
[Chemical Formula 2]

wherein

X is a halogen;

$R_6$ is halo(C1-C20)alkyl or (C1-C20)alkoxy;

A is —CO— or —SO$_2$—;

$R_7$ is (C1-C20)alkyl, (C1-C20)alkoxy, (C6-C20)aryl, (C1-C20)alkyl(C6-C20) aryl, or —NR$_{11}$R$_{12}$;

$R_{11}$ and $R_{12}$ are independently of each other hydrogen or (C1-C20)alkyl; and n is an integer of 0 or 1.

Preferably, in Chemical Formula 2 according to an exemplary embodiment of the present invention, A may be —CO—; $R_6$ and $R_7$ may be independently of each other (C1-C20)alkoxy; and n may be an integer of 1.

The metal complex of Chemical Formula 1 according to an exemplary embodiment of the present invention may be used as a catalyst for preparing a gamma-lactam compound from a dioxazol-one compound.

In another general aspect, a method of preparing a metal complex represented by the following Chemical Formula 1 includes: reacting a metal precursor compound of the following Chemical Formula 3A and a quinoline-based compound of the following Chemical Formula 3B in the presence of a base to prepare the metal complex of the following Chemical Formula 1:

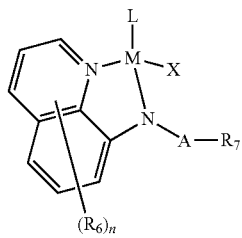
[Chemical Formula 1]

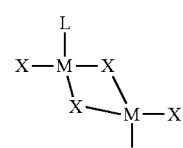
[Chemical Formula 2]

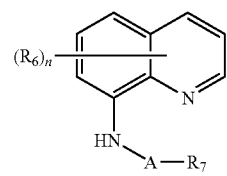
[Chemical Formula 3]

wherein

M is iridium, rhodium, ruthenium, or cobalt;

L is

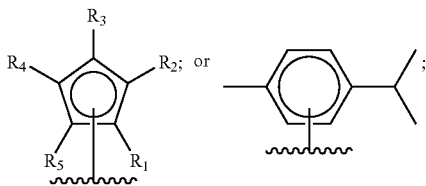

X is independently of each other a halogen;

$R_1$ to $R_5$ are independently of one another hydrogen or (C1-C20)alkyl; and $R_6$ is a halogen, (C1-C20)alkyl, halo(C1-C20)alkyl, (C1-C20)alkoxy, (C6-C20)aryl, or (C3-C20)heteroaryl;

A is —CO— or —SO$_2$—;

$R_7$ is (C1-C20)alkyl, (C1-C20)alkoxy, (C6-C20)aryl, (C1-C20)alkyl(C6-C20) aryl, or —NR$_{11}$R$_{12}$;

$R_{11}$ and $R_{12}$ are independently of each other hydrogen or (C1-C20)alkyl; and n is an integer of 0 to 6.

Preferably, in the method of preparing the compound of Chemical Formula 1 according to an exemplary embodiment of the present invention, the base may be any one or two or more selected from NaOAc, Na$_2$CO$_3$, NaHNO$_3$, Cu(OAc)$_2$, Cu(OAc)$_2$·H$_2$O, and Net$_3$, and may be used at 2 to 10 mol with respect to 1 mol of the metal precursor compound of Chemical Formula 3A.

The quinoline-based compound of Chemical Formula 3B according to an exemplary embodiment of the present invention may be used at 1.5 to 2.5 mol with respect to 1 mol of the metal precursor compound of Chemical Formula 3A.

In another general aspect, a method of preparing a gamma-lactam compound includes: amidating a dioxazol-one compound in the presence of a metal complex represented by the following Chemical Formula 1 and a base to prepare the gamma-lactam compound:

[Chemical Formula 1]

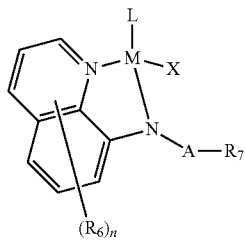

wherein
M is iridium, rhodium, ruthenium, or cobalt;
L is

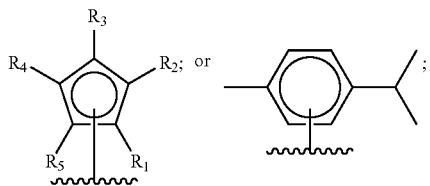

X is a halogen;
$R_1$ to $R_5$ are independently of one another hydrogen or (C1-C20)alkyl; and
$R_6$ is a halogen, (C1-C20)alkyl, halo(C1-C20)alkyl, (C1-C20)alkoxy, (C6-C20)aryl, or (C3-C20)heteroaryl;
A is —CO— or —SO$_2$—;
$R_7$ is (C1-C20)alkyl, (C1-C20)alkoxy, (C6-C20)aryl, (C1-C20)alkyl(C6-C20) aryl, or —NR$_{11}$R$_{12}$;
$R_{11}$ and $R_{12}$ are independently of each other hydrogen or (C1-C20)alkyl; and
n is an integer of 0 to 6.

Preferably, the dioxazol-one compound according to an exemplary embodiment of the present invention may be represented by the following Chemical Formula 4, and the gamma-lactam compound may be presented by the following Chemical Formula 5:

[Chemical Formula 4]

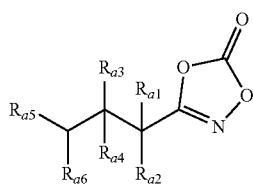

[Chemical Formula 5]

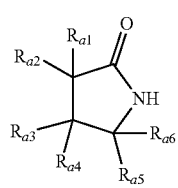

wherein
$R_{a1}$ to $R_{a6}$ are independently of one another hydrogen, (C1-C20)alkyl, (C3-C20)cycloalkyl, (C2-C20)alkenyl, (C2-C20)alkynyl, (C1-C20)alkoxy, (C6-C20)aryl, (C3-C20)heteroaryl, or (C3-C20)heterocycloalkyl, or may be connected to an adjacent substituent to form an aromatic ring, an alicyclic ring, or spiro ring with or without a fused ring;

the alkyl, the cycloalkyl, the alkenyl, the alkynyl, the alkoxy, the aryl, the heteroaryl, the aromatic ring, the alicyclic ring, or the spiro ring of $R_{a1}$ to $R_{a6}$ may be further substituted by any one or more substituents selected from a halogen, nitro, cyano, (C1-C20)alkyl, (C1-C20)alkenyl, (C1-C20)alkoxy, (C6-C20)aryl, (C6-C20)aryl(C1-C20)alkyl (C3-C20)heteroaryl, (C3-C20)heterocycloalkyl, and —N(R$_{a11}$)(R$_{a12}$);

$R_{a11}$ and $R_{a12}$ are independently of each other hydrogen, (C1-C20)alkyl, or (C1-C20)alkoxycarbonyl.

Preferably, the base according to an exemplary embodiment of the method of preparing a gamma-lactam compound of the present invention may be one or two or more selected from NaBAr$^F_4$ (Sodium tetrakis[3,5-bis(trifluoromethyl)phenyl]borate), AgSbF$_6$ (Silver hexafluoroantimonate(V)), AgNTf$_2$ (Silver bis(trifluoromethanesulfonyl)imide), AgBF$_4$ (Silver tetrafluoroborate), AgPF$_6$ (Silver hexafluorophosphate), AgOTf (Silver trifluoromethanesulfonate), and AgOAc (Silver acetate), and may be used at 0.01 to 0.1 mol with respect to 1 mol of the dioxazol-one compound.

The metal complex of Chemical Formula 1 according to an exemplary embodiment of the present invention may be used as a catalyst and may be used at 0.01 to 0.1 mol with respect to 1 mol of the dioxazol-one compound.

Preferably, the amidation according to an exemplary embodiment of the present invention may be performed at 20 to 60° C.

Preferably, in Chemical Formula 1 according to an exemplary embodiment of the method of preparing a gamma-lactam compound of the present invention, M may be iridium; L may be

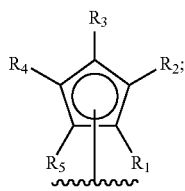

X may be chloro; $R_1$ to $R_5$ may be independently of one another (C1-C20)alkyl; $R_6$ may be (C1-C20)alkoxy; A may be —CO—; $R_7$ may be (C1-C20)alkoxy; and n may be an integer of 0 or 1.

Preferably, in Chemical Formulae 4 and 5 according to an exemplary embodiment of the method of preparing a gamma-lactam compound of the present invention, $R_{a1}$ to $R_{a6}$ may be independently of one another hydrogen, (C1-C20)alkyl, (C3-C20)cycloalkyl, (C2-C20)alkenyl, (C2-C20)alkynyl, (C6-C20)aryl, (C3-C20)heteroaryl, or (C3-C20)heterocycloalkyl, or connected to an adjacent substituent to form an aromatic ring, an alicyclic ring, or a spiro ring with or without a fused ring; the alkyl, the cycloalkyl, the alkenyl, the alkynyl, the aryl, the heteroaryl, the aromatic ring, the alicyclic ring, or the spiro ring of $R_{a1}$ to $R_{a6}$ may be further substituted by any one or more substituents selected from a halogen, nitro, cyano, (C1-C20)alkyl, (C1-C20)alkenyl, (C1-C20)alkoxy, (C6-C20)aryl, (C6-C20)aryl(C1-C20)alkyl (C3-C20)heteroaryl, (C3-C20)heterocycloalkyl, and —N(R$_{a11}$)(R$_{a12}$); and R$_{a11}$ and R$_{a12}$ may be independently of each other (C1-C20)alkyl or (C1-C20)alkoxycarbonyl.

More preferably, $R_{a1}$ to $R_{a5}$ may be independently of each other hydrogen, (C1-C20)alkyl, or (C3-C20)heterocycloalkyl; $R_{a6}$ may be independently of each other hydrogen, (C1-C20)alkyl, (C3-C20)cycloalkyl, (C2-C20)alkenyl, (C2-C20)alkynyl, (C6-C20)aryl, or (C3-C20)heteroaryl, or $R_{a5}$ and $R_{a6}$ may be connected to form a (C5-C8)spiro ring, $R_{a2}$ and $R_{a3}$ may be connected with (C2-C10)alkenylene to form a (C6-C12)aromatic ring, and in this case, $R_{a1}$ and $R_{a2}$ are absent, $R_{a3}$ and $R_{a6}$ may be connected to each other to form a (C3-C20)alicyclic ring with or without an aromatic ring, $R_{a3}$ and $R_{a4}$ and $R_{a6}$ may be connected to each other to form a (C3-C20)alicyclic ring with or without an aromatic ring; the alkyl of $R_{a1}$ to $R_{a5}$, and the alkyl, the cycloalkyl, the alkenyl, the alkynyl, the aryl, or the heteroaryl of $R_{a6}$ may be further substituted by any one or more substituents selected from a halogen, nitro, cyano, (C1-C20)alkyl, (C1-C20)alkenyl, (C1-C20)alkoxy, (C6-C20)aryl, (C6-C20)aryl (C1-C20)alkyl (C3-C20) heterocycloalkyl, and —N($R_{a11}$)($R_{a12}$); and $R_{a11}$ and $R_{a12}$ may be independently of each other hydrogen, (C1-C20)alkyl, or (C1-C20)alkoxycarbonyl.

Specifically, the method of preparing a gamma-lactam compound according to an exemplary embodiment of the present invention may include amidating the dioxazol-one compound of the following Chemical Formula 6 in the presence of the compound represented by Chemical Formula 1 and the base to prepare a gamma-lactam compound of the following Chemical Formula 7:

[Chemical Formula 6]

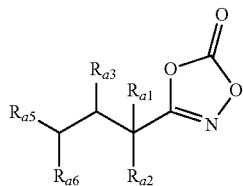

[Chemical Formula 7]

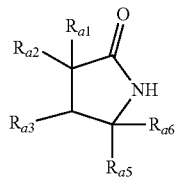

wherein $R_{a1}$ and $R_{a3}$ are independently of each other hydrogen, (C1-C20)alkyl, or (C3-C20)heterocycloalkyl;

$R_{a2}$ and $R_{a5}$ are independently of each other hydrogen or (C1-C20)alkyl;

$R_{a6}$ is (C1-C20)alkyl, (C3-C20)cycloalkyl, (C2-C20)alkenyl, (C2-C20)alkynyl, (C6-C20)aryl, or (C3-C20)heteroaryl;

the alkyl, the cycloalkyl, the alkenyl, the alkynyl, the aryl, and the heteroaryl of $R_{a6}$ may be further substituted by any one or more substituents selected from a halogen, nitro, cyano, (C1-C20)alkyl, (C2-C20)alkenyl, (C1-C20)alkoxy, (C6-C20)aryl, (C6-C20)aryl(C1-C20)alkyl, and —N($R_{a11}$)($R_{a12}$); and $R_{a11}$ and $R_{a12}$ are independently of each other hydrogen, (C1-C20)alkyl, or (C1-C20)alkoxycarbonyl.

Specifically, the method of preparing a gamma-lactam compound according to a second embodiment of the present invention may include amidating the dioxazol-one compound of the following Chemical Formula 8 in the presence of the compound represented by Chemical Formula 1 and the base to prepare a gamma-lactam compound of the following Chemical Formula 9:

[Chemical Formula 8]

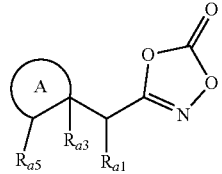

[Chemical Formula 9]

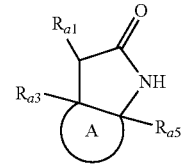

wherein ring A is a (C3-C20)alicyclic ring with or without an aromatic ring;

$R_{a1}$ and $R_{a3}$ are independently of each other hydrogen or (C1-C20)alkyl, and $R_{a5}$ is hydrogen or (C2-C20)alkenyl;

the alkyl of $R_{a1}$ and $R_{a3}$ and the alkenyl of $R_{a5}$ may be further substituted by any one or more substituents selected from a halogen, nitro, cyano, (C1-C20)alkyl, (C2-C20)alkenyl, (C1-C20)alkoxy, (C6-C20)aryl, (C6-C20)heteroaryl, (C3-C20)heterocycloalkyl, and —N($R_{a21}$)($R_{a22}$) and $R_{a21}$ and $R_{a22}$ are independently of each other hydrogen, (C1-C20)alkyl, or (C1-C20)alkoxycarbonyl.

Specifically, the method of preparing a gamma-lactam compound of a third embodiment of the present invention may include amidating the dioxazol-one compound of the following Chemical Formula 10 in the presence of the compound represented by Chemical Formula 1 and the base to prepare a gamma-lactam compound of the following Chemical Formula 11:

[Chemical Formula 10]

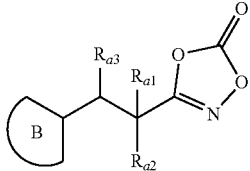

[Chemical Formula 11]

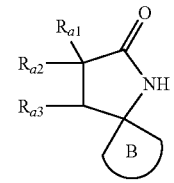

wherein $R_{a1}$ to $R_{a3}$ are independently of one another hydrogen or (C1-C20)alkyl;

ring B is an alicyclic ring; and the alkyl of $R_{a1}$ to $R_{a3}$ and the alicyclic ring of ring B may be further substituted by any one or more substituents selected from a halogen, nitro, cyano, (C1-C20)alkyl, (C2-C20)alkenyl, (C1-C20)alkoxy, (C6-C20)aryl, and (C6-C20)aryl(C1-C20)alkyl.

Specifically, the method of preparing a gamma-lactam compound of a fourth embodiment of the present invention may include amidating the dioxazol-one compound of the following Chemical Formula 12 in the presence of the compound represented by Chemical Formula 1 and the base to prepare a gamma-lactam compound of the following Chemical Formula 13:

[Chemical Formula 12]

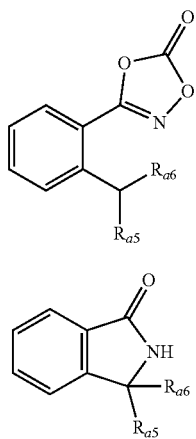

[Chemical Formula 13]

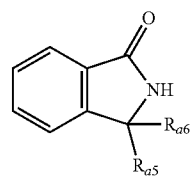

wherein $R_{a5}$ and $R_{a6}$ are independently of each other hydrogen, (C1-C20)alkyl, or (C6-C20)aryl.

In still another general aspect, a gamma-lactam compound represented by Chemical Formula 5 is provided.

Advantageous Effects

The metal complex of the present invention adopts a specific functional group as a ligand in a metal, and thus, is very useful as a catalyst for preparing a gamma-lactam compound from a dioxazol-one compound.

Therefore, the method of preparing a gamma-lactam compound using the metal complex of Chemical Formula 1 of the present invention as a catalyst may easily produce a high-purity gamma-lactam compound with high selectivity and yield from various dioxazol-one compounds, and thus, the prepared gamma-lactam compound may be useful as a raw material, an intermediate, and the like in various fields.

BEST MODE

Hereinafter, the novel metal complex of the present invention, the method of preparing the same, and the method of preparing a gamma-lactam compound from a dioxazol-one compound using the same will be described in detail, but the present invention is not limited thereto.

"Alkyl", "alkoxy", and a substituent containing "alkyl" described herein refer to a hydrocarbon radical in a linear or branched form having 1 to 20 carbon atoms.

"Alkenyl" described herein is an organic radical derived from a hydrocarbon containing one or more double bonds, and "alkynyl" described herein is an organic radical derived from a hydrocarbon containing one or more triple bonds.

"Haloalkyl" described herein refers to one or more hydrogens of the alkyl being substituted by one or more halogens, preferably fluorines.

"Cycloalkyl" described herein refers to a non-aromatic monocyclic or multicyclic ring system having 3 to 20 carbon atoms, and a monocyclic ring includes cyclopropyl, cyclobutyl, cyclopentyl, and cyclohexyl, without limitation. An example of the multicyclic cycloalkyl group includes perhydronaphthyl, perhydroindenyl, and the like; and a bridged multicyclic cycloalkyl group includes adamantyl, norbornyl, and the like.

"Heterocycloalkyl" described herein refers to a non-aromatic monocyclic or multicyclic ring system having 3 to 20 carbon atoms containing 1 to 4 heteroatoms selected from B, N, O, S, P(=O), Si, and P, and phthalimido

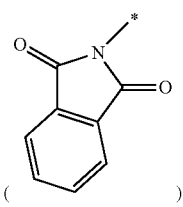

of the present invention is included therein.

"Aryl" described herein is an organic radical derived from an aromatic hydrocarbon by removal of one hydrogen, including a monocyclic or fused ring system containing appropriately 4 to 7, preferably 5 or 6 ring atoms in each ring, and even including a form in which a plurality of aryls are connected by a single bond. A specific example includes phenyl, naphthyl, biphenyl, terphenyl, anthryl, indenyl, fluorenyl, phenanthryl, triphenylenyl, pyrenyl, perylenyl, crycenyl, naphthacenyl, fluoranthenyl, and the like. Naphthyl includes 1-naphthyl and 2-naphthyl, anthryl includes 1-anthryl, 2-anthryl, and 9-anthryl, and fluorenyl includes all of 1-fluorenyl, 2-fluorenyl, 3-fluorenyl, 4-fluorenyl, and 9-fluorenyl.

"Heteroaryl" described herein refers to an aryl group containing 1 to 4 heteroatoms selected from B, N, O, S, P(=O), Si, and P as an aromatic ring backbone atom, and carbons as remaining aromatic ring backbone atoms, and is a 5- or 6-membered monocyclic heteroaryl and a multicyclic heteroaryl fused with one or more benzene rings, which may be partially saturated. In addition, heteroaryl in the present invention also includes a form in which one or more heteroaryls are connected by a single bond.

"Arylalkyl" described herein alone or as a portion of another group refers to a functional group in which one or more hydrogens of an aryl group are substituted with alkyl, and as an example, may be methylphenyl or the like.

A fused ring of an aromatic ring, an alicyclic ring, or a spiro ring containing a fused ring described herein may be an aromatic ring, an alicyclic ring, or a spiro ring, preferably an aromatic ring or alicyclic ring, and specifically a C6-C12 aromatic ring or a C1-C12 alicyclic ring, but is not limited thereto.

In addition, a "(C1-C20)alkyl group" described herein is preferably (C1-C10)alkyl, and more preferably (C1-C7) alkyl, a "(C3-C20)cycloalkyl group" is preferably (C3-C12) cycloalkyl, a "(C3-C20)heterocycloalkyl group" is preferably (C3-C12)heterocycloalkyl, a "(C6-C20)aryl group" is preferably (C6-C12)aryl, and a "(C3-C30)heteroaryl group" is preferably (C3-C12)heteroaryl.

The present invention provides a novel metal complex, and the metal complex of the present invention may be useful as a catalyst for preparing gamma-lactam having excellent activity and chemical selectivity and is represented by the following Chemical Formula 1:

[Chemical Formula 1]

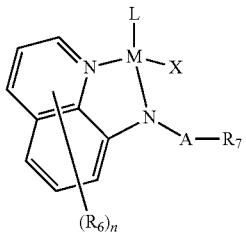

wherein

M is iridium, rhodium, ruthenium, or cobalt;

L is

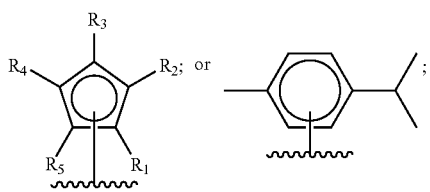

X is a halogen;

$R_1$ to $R_5$ are independently of one another hydrogen or (C1-C20)alkyl; and $R_6$ is a halogen, (C1-C20)alkyl, halo(C1-C20)alkyl, (C1-C20)alkoxy, (C6-C20)aryl, or (C3-C20)heteroaryl;

A is —CO— or —$SO_2$—;

$R_7$ is (C1-C20)alkyl, (C1-C20)alkoxy, (C6-C20)aryl, (C1-C20)alkyl(C6-C20) aryl, or —$NR_{11}R_{12}$;

$R_{11}$ and $R_{12}$ are independently of each other hydrogen or (C1-C20)alkyl; and n is an integer of 0 to 6.

The novel metal complex of the present invention is a catalyst of a gamma-lactam compound, has excellent catalytic activity, and amidates a dioxazol-one compound under mild conditions unlike conventional catalysts to prepare a gamma-lactam compound with high selectivity and yield.

In terms of obtaining a gamma-lactam compound with excellent selectivity and yield, in Chemical Formula 1, L may be

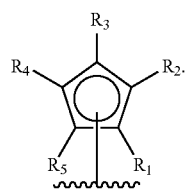

More preferably, in Chemical Formula 1, L may be

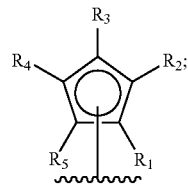

X may be Cl or Br; $R_1$ to $R_5$ may be independently of one another (C1-C20)alkyl; $R_6$ may be halo(C1-C20)alkyl or (C1-C20)alkoxy; and n may be an integer of 0 to 6.

More preferably, Chemical Formula 1 according to an exemplary embodiment of the present invention may be represented by the following Chemical Formula 2:

[Chemical Formula 2]

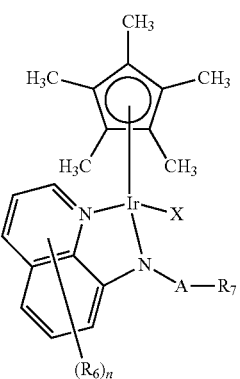

wherein

X is a halogen;

$R_6$ is halo(C1-C20)alkyl or (C1-C20)alkoxy;

A is —CO— or —$SO_2$—;

$R_7$ is (C1-C20)alkyl, (C1-C20)alkoxy, (C6-C20)aryl, (C1-C20)alkyl(C6-C20) aryl, or —$NR_{11}R_{12}$;

$R_{11}$ and $R_{12}$ are independently of each other hydrogen or (C1-C20)alkyl; and n is an integer of 0 or 1.

In terms of a more efficient reaction, preferably, in Chemical Formula 2 according to an exemplary embodiment of the present invention, A may be —CO—.

In terms of a still more efficient reaction, preferably, in Chemical Formula 2 according to an exemplary embodiment of the present invention, A may be —CO—; $R_6$ and $R_7$ may be independently of each other (C1-C20)alkoxy; n may be an integer of 1, and the compound represented by Chemical Formula 1 of the present invention may be used as a catalyst which may easily produce a gamma-lactam compound from a dioxazol-one compound.

The metal complex according to an exemplary embodiment of the present invention has excellent catalytic activity and significantly improved selectivity as compared with conventional catalyst, by introducing a different ligand from those of the conventional catalysts, and thus, a gamma-lactam compound may be easily obtained with high selectivity and yield.

Furthermore, the metal complex according to an exemplary embodiment of the present invention progresses an amidation reaction under mild conditions, thereby allowing mass production of a gamma-lactam compound which is very useful as a raw material, an intermediate, and the like.

In addition, the present invention provides a method of preparing a metal complex represented by Chemical Formula 1 including: reacting a metal precursor compound of the following Chemical Formula 3A and a quinoline-based compound of the following Chemical Formula 3B in the presence of a base to prepare the metal complex of Chemical Formula 1:

[Chemical Formula 3A]

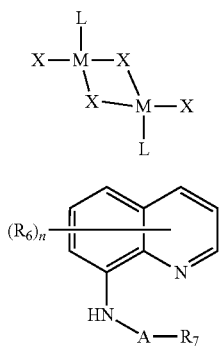

[Chemical Formula 3B]

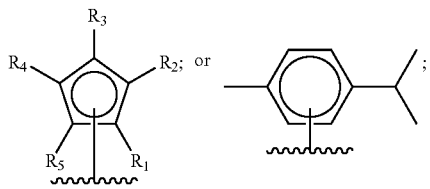

wherein
M is iridium, rhodium, ruthenium, or cobalt;
L is

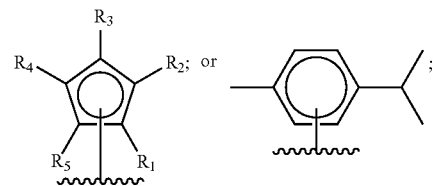

X is independently of each other a halogen;
$R_1$ to $R_5$ are independently of one another hydrogen or (C1-C20)alkyl; and
$R_6$ is a halogen, (C1-C20)alkyl, halo(C1-C20)alkyl, (C1-C20)alkoxy, (C6-C20)aryl, or (C3-C20)heteroaryl;
A is —CO— or —SO$_2$—;
$R_7$ is (C1-C20)alkyl, (C1-C20)alkoxy, (C6-C20)aryl, (C1-C20)alkyl(C6-C20) aryl, or —NR$_{11}$R$_{12}$;
$R_{11}$ and $R_{12}$ are independently of each other hydrogen or (C1-C20)alkyl; and
n is an integer of 0 to 6.

Preferably, in the method of preparing the compound of Chemical Formula 1 according to an exemplary embodiment of the present invention, the base may be any one or two or more selected from NaOAc, Na$_2$CO$_3$, NaHNO$_3$, Cu(OAc)$_2$, Cu(OAc)$_2$·H$_2$O, and NEt$_3$, and more preferably any one or two or more selected from NaOAc, Na$_2$CO$_3$, NaHNO$_3$, and Net$_3$, and may be used at 2 to 10 mol, preferably 4 to 8 mol with respect to 1 mol of the metal precursor compound of Chemical Formula 3A.

The quinoline-based compound of Chemical Formula 3B according to an exemplary embodiment of the present invention may be used at 1.5 to 2.5 mole, preferably 1.7 to 2.3 mol with respect to 1 mol of the metal precursor compound of Chemical Formula 3A.

In another general aspect, a method of preparing a gamma-lactam compound includes: amidating a dioxazol-one compound in the presence of a metal complex represented by the following Chemical Formula 1 and a base to prepare the gamma-lactam compound:

[Chemical Formula 1]

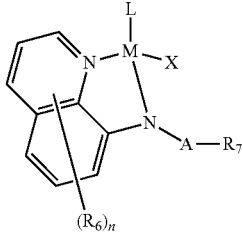

wherein
M is iridium, rhodium, ruthenium, or cobalt;
L is

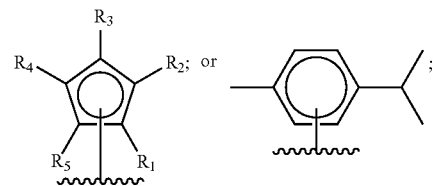

X is a halogen;
$R_1$ to $R_5$ are independently of one another hydrogen or (C1-C20)alkyl; and
$R_6$ is a halogen, (C1-C20)alkyl, halo(C1-C20)alkyl, (C1-C20)alkoxy, (C6-C20)aryl, or (C3-C20)heteroaryl;
A is —CO— or —SO$_2$—;
$R_7$ is (C1-C20)alkyl, (C1-C20)alkoxy, (C6-C20)aryl, (C1-C20)alkyl(C6-C20) aryl, or —NR$_{11}$R$_{12}$;
$R_{11}$ and $R_{12}$ are independently of each other hydrogen or (C1-C20)alkyl; and
n is an integer of 0 to 6.

Preferably, the metal complex according to an exemplary embodiment of the present invention may be represented by the following Chemical Formula 1-1:

[Chemical Formula 1-1]

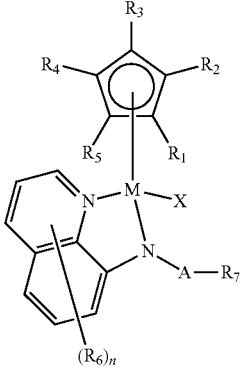

wherein M, X, $R_1$ to $R_7$, A, and n are as defined in Chemical Formula 1.

Preferably, the dioxazol-one compound according to an exemplary embodiment of the present invention may be represented by the following Chemical Formula 4, and the gamma-lactam compound may be presented by the following Chemical Formula 5:

[Chemical Formula 4]

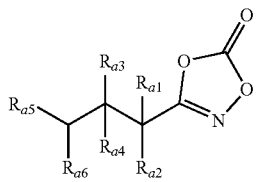

[Chemical Formula 5]

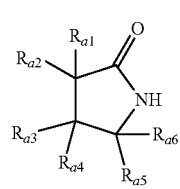

wherein $R_{a1}$ to $R_{a6}$ are independently of one another hydrogen, (C1-C20)alkyl, (C3-C20)cycloalkyl, (C2-C20)alkenyl, (C2-C20)alkynyl, (C1-C20)alkoxy, (C6-C20)aryl, (C3-C20)heteroaryl, or (C3-C20)heterocycloalkyl, or may be connected to an adjacent substituent to form an aromatic ring, an alicyclic ring, or spiro ring with or without a fused ring;

the alkyl, the cycloalkyl, the alkenyl, the alkynyl, the alkoxy, the aryl, the heteroaryl, the aromatic ring, the alicyclic ring, or the spiro ring of $R_{a1}$ to $R_{a6}$ may be further substituted by any one or more substituents selected from a halogen, nitro, cyano, (C1-C20)alkyl, (C1-C20)alkenyl, (C1-C20)alkoxy, (C6-C20)aryl, (C6-C20)aryl(C1-C20)alkyl, (C3-C20)heteroaryl, (C3-C20)heterocycloalkyl, and —N($R_{a11}$)($R_{a12}$); and $R_{a11}$ and $R_{a12}$ are independently of each other hydrogen, (C1-C20)alkyl, or (C1-C20)alkoxycarbonyl.

The method of preparing a gamma-lactam compound of the present invention may easily produce a gamma-lactam compound unlike unstable conventional methods, by introducing a dioxazol-one compound which is a specific starting material as a starting material instead of carbonylnitrenes which have been used as a conventional starting material, and furthermore, may produce a gamma-lactam compound with high selectivity under mild conditions.

Besides, the method of preparing a gamma-lactam compound of the present invention adopts a quinoline amine compound which is not a conventionally used catalyst but a specific ligand, thereby easily preparing a gamma-lactam compound with high selectivity and yield under mild conditions.

Preferably, the base according to an exemplary embodiment of the method of preparing a gamma-lactam compound of the present invention may be one or two or more selected from NaBAr$^F_4$ (sodium tetrakis[3,5-bis(trifluoromethyl)phenyl]borate), AgSbF$_6$ (silver hexafluoroantimonate(V)), AgNTf$_2$ (silver bis(trifluoromethanesulfonyl)imide), AgBF$_4$ (silver tetrafluoroborate), AgPF$_6$ (silver hexafluorophosphate), AgOTf (silver trifluoromethanesulfonate), and AgOAc (silver acetate), preferably one or two or more selected from NaBAr$^F_4$ (sodium tetrakis[3,5-bis(trifluoromethyl)phenyl]borate), AgSbF$_6$, AgNTf$_2$, and AgBF$_4$, and may be used at 0.01 to 0.1 mol, preferably 0.01 to 0.07 mol with respect to 1 mol of the dioxazol-one compound.

The metal complex according to an exemplary embodiment of the present invention is used as a catalyst, and may be used at 0.01 to 0.1 mol, preferably 0.01 to 0.07 mol with respect to 1 mol of the dioxazol-one compound.

Preferably, amidation according to an exemplary embodiment of the present invention may be performed by stirring at 20 to 60° C., preferably 30 to 50° C. for 8 to 24 hours, preferably 10 to 15 hours.

In the method of preparing a gamma-lactam compound according to an exemplary embodiment of the present invention, amidation may be performed under an organic solvent, and it is not necessary to limit the organic solvent as long as it dissolves the reaction material. As the organic solvent according to an exemplary embodiment of the present invention, one or more selected from acetonitrile, dichloromethane, dichloroethane, nitromethane, toluene, and benzene may be used, and considering solubility and ease of removal of the reactant, one or more selected from dichloromethane, dichloroethane, and acetonitrile may be used as a solvent.

Preferably, in Chemical Formula 1 according to an exemplary embodiment of the method of preparing a gamma-lactam compound of the present invention, M may be iridium; L may be

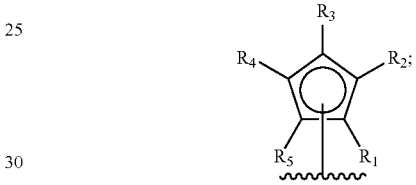

X may be chloro; $R_1$ to $R_5$ may be independently of one another (C1-C20)alkyl; $R_6$ may be (C1-C20)alkoxy; A may be —CO—; $R_7$ may be (C1-C20)alkoxy; and n may be an integer of 0 or 1.

Preferably, in Chemical Formulae 4 and 5 according to an exemplary embodiment of the method of preparing a gamma-lactam compound of the present invention, $R_{a1}$ to $R_{a5}$ may be independently of each other hydrogen, (C1-C20) alkyl, or (C3-C20)heterocycloalkyl; $R_{a6}$ may be independently of each other hydrogen, (C1-C20)alkyl, (C3-C20) cycloalkyl, (C2-C20)alkenyl, (C2-C20)alkynyl, (C6-C20) aryl, or (C3-C20)heteroaryl, or $R_{a5}$ and $R_{a6}$ may be connected to form a (C5-C8)spiro ring, $R_{a2}$ and $R_{a3}$ may be connected with (C2-C10)alkenylene to form a (C6-C12) aromatic ring, and in this case, $R_{a1}$ and $R_{a2}$ are absent, $R_{a3}$ and $R_{a6}$ may be connected to each other to form a (C3-C20) alicyclic ring with or without an aromatic ring, $R_{a3}$ and $R_{a4}$ and $R_{a6}$ may be connected to each other to form a (C3-C20) alicyclic ring with or without an aromatic ring; the alkyl of $R_{a1}$ to $R_{a5}$, and the alkyl, the cycloalkyl, the alkenyl, the alkynyl, the aryl, or the heteroaryl of $R_{a6}$ may be further substituted by any one or more substituents selected from a halogen, nitro, cyano, (C1-C20)alkyl, (C1-C20)alkenyl, (C1-C20)alkoxy, (C6-C20)aryl, (C6-C20)aryl(C1-C20)alkyl (C3-C20) heterocycloalkyl, and —N($R_{a11}$)($R_{a12}$); and $R_{a11}$ and $R_{a12}$ may be independently of each other hydrogen, (C1-C20)alkyl, or (C1-C20)alkoxycarbonyl.

Preferably, a first embodiment of the method of preparing a gamma-lactam compound of the present invention may include amidating the dioxazol-one compound of the following Chemical Formula 6 in the presence of the compound represented by Chemical Formula 1 and the base to prepare a gamma-lactam compound of the following Chemical Formula 7:

[Chemical Formula 6]

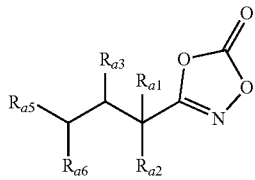

[Chemical Formula 7]

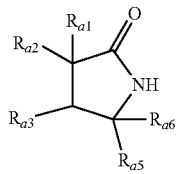

wherein $R_{a1}$ and $R_{a3}$ are independently of each other hydrogen, (C1-C20)alkyl, or (C3-C20)heterocycloalkyl;

$R_{a2}$ and $R_{a5}$ are independently of each other hydrogen or (C1-C20)alkyl;

$R_{a6}$ is (C1-C20)alkyl, (C3-C20)cycloalkyl, (C2-C20)alkenyl, (C2-C20)alkynyl, (C6-C20)aryl, or (C3-C20)heteroaryl;

the alkyl, the cycloalkyl, the alkenyl, the alkynyl, the aryl, and the heteroaryl of $R_{a6}$ may be further substituted by any one or more substituents selected from a halogen, nitro, cyano, (C1-C20)alkyl, (C2-C20)alkenyl, (C1-C20)alkoxy, (C6-C20)aryl, (C6-C20)aryl(C1-C20)alkyl, and —N($R_{a11}$)($R_{a12}$); and $R_{a11}$ and $R_{a12}$ are independently of each other hydrogen, (C1-C20)alkyl, or (C1-C20)alkoxycarbonyl.

Preferably, a second embodiment of the gamma-lactam compound of the present invention may be prepared by including amidating the dioxazol-one compound of the following Chemical Formula 8 in the presence of the compound represented by Chemical Formula 1 and the base to prepare a gamma-lactam compound of the following Chemical Formula 9:

[Chemical Formula 8]

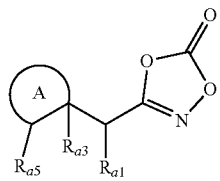

[Chemical Formula 9]

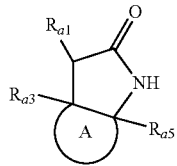

wherein ring A is a (C3-C20)alicyclic ring with or without an aromatic ring;

$R_{a1}$ and $R_{a3}$ are independently of each other hydrogen or (C1-C20)alkyl, and $R_{a5}$ is hydrogen or (C2-C20)alkenyl;

the alkyl of $R_{a1}$ and $R_{a3}$ and the alkenyl of $R_{a5}$ may be further substituted by any one or more substituents selected from a halogen, nitro, cyano, (C1-C20)alkyl, (C2-C20)alkenyl, (C1-C20)alkoxy, (C6-C20)aryl, (C6-C20)heteroaryl, (C3-C20)heterocycloalkyl, and —N($R_{a21}$)($R_{a22}$) and $R_{a21}$ and $R_{a22}$ are independently of each other hydrogen, (C1-C20)alkyl, or (C1-C20)alkoxycarbonyl.

Preferably, a third embodiment of the gamma-lactam compound of the present invention may be prepared by including amidating the dioxazol-one compound of the following Chemical Formula 10 in the presence of the compound represented by Chemical Formula 1 and the base to prepare a gamma-lactam compound of the following Chemical Formula 11:

[Chemical Formula 10]

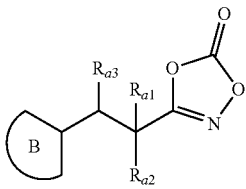

[Chemical Formula 11]

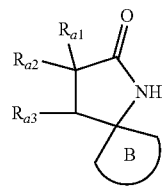

wherein $R_{a1}$ to $R_{a3}$ are independently of one another hydrogen or (C1-C20)alkyl;

ring B is an alicyclic ring; and the alkyl of $R_{a1}$ to $R_{a3}$ and the alicyclic ring of ring B may be further substituted by any one or more substituents selected from a halogen, nitro, cyano, (C1-C20)alkyl, (C2-C20)alkenyl, (C1-C20)alkoxy, (C6-C20)aryl, and (C6-C20)aryl(C1-C20)alkyl.

Preferably, a fourth embodiment of the gamma-lactam compound of the present invention may be prepared by including amidating the dioxazol-one compound of the following Chemical Formula 12 in the presence of the compound represented by Chemical Formula 1 and the base to prepare a gamma-lactam compound of the following Chemical Formula 13:

[Chemical Formula 12]

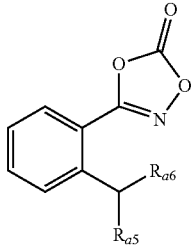

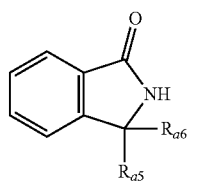

wherein $R_{a5}$ and $R_{a6}$ are independently of each other hydrogen, (C1-C20)alkyl, or (C6-C20)aryl.

In addition, the present invention provides a gamma-lactam compound represented by Chemical Formula 5.

Hereinafter, the constitution of the present invention will be described in detail by the Examples, and the following Examples are for better understanding of the present invention, but the scope of the present invention is not limited thereto.

Preparation Example I: Preparation of Quinoline Ligand

Method 1.

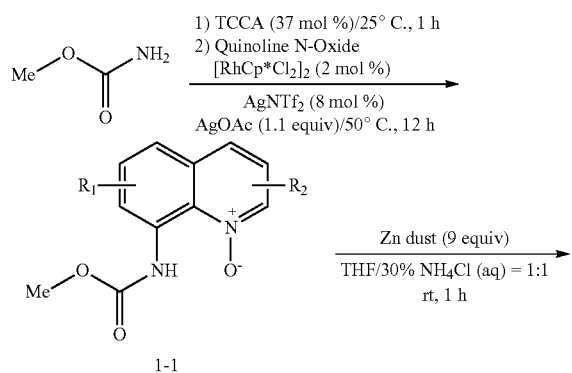

Methyl carbamate (1.1 mmol, 1.1 equivalents to quinoline N-oxide, 82.5 mg), trichloroisocyanuric acid (TCCA, 86 mg, 0.36 mmol, 37 mol %), and MeOH (2 mL) were added to a vial and the mixture was stirred at 25° C. for 1 hour. Quinoline N-oxide (1.0 mmol), [RhCp*Cl$_2$]$_2$ (Cp*: pentamethylcyclopentadienyl) (12.5 mg, 0.02 mmol, 2 mol %), AgNTf$_2$ (31 mg, 0.08 mmol, 8 mol %), AgOAc (183.5 mg, 1.1 mmol), and MeOH (1 mL) were added thereto again and the mixture was stirred at 50° C. for 12 hours. After the reaction was completed, the reaction mixture was filtered with celite (dichloromethane (15 mL×3)). After the solvent was removed by distillation under reduced pressure, separation and purification were performed by column chromatography (dichloromethane/methanol=30:1 to 10:1) to obtain compound 1-1 as a title compound.

Compound 1-1 was dissolved in THF (15 mL), an aqueous 30% NH$_5$Cl solution (15 mL) and zinc dust (0.59 g, 9 mmol) were added thereto, and the mixture was stirred at room temperature for 1 hour. Thereafter, H$_2$O (50 mL) was added to the reaction mixture, extraction was performed with EtOAc (50 mL×3), and drying was performed with MgSO$_4$ to remove residual moisture. After the solvent was removed by distillation under reduced pressure, separation and purification were performed by column chromatography (eluent: n-hexane/EtOAc=4:1 to 1:1) to prepare quinoline ligand compound 1-2.

The following quinoline ligand compound was prepared in the same manner as in the above, except that a starting material having different substituents was used.

[Preparation Example 1] Preparation of methyl quinolin-8-ylcarbamate

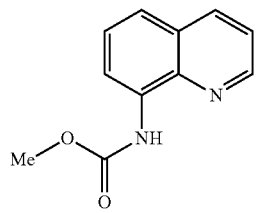 [SMILES: COC(=O)Nc1cccc2cccnc12]

White solid (0.12 g, 61%, 2 steps yield); m.p. 65-67° C.; $^1$H NMR (600 MHz, CDCl$_3$) δ 9.21 (s, 1H), 8.78 (d, J=4.2 Hz, 1H), 8.42 (d, J=6.3 Hz, 1H), 8.13 (dd, J=8.2, 1.5 Hz, 1H), 7.53 (t, J=8.0 Hz, 1H), 7.47-7.40 (m, 2H), 3.85 (s, 3H); $^{13}$C NMR (150 MHz, CDCl$_3$) δ 154.1, 148.1, 138.2, 136.2, 134.7, 128.0, 127.3, 121.6, 120.6, 114.5, 52.3; IR (cm$^{-1}$) 3358, 1728, 1524, 1486, 1200; HRMS (EI) m/z calcd. for C$_{11}$H$_{10}$N$_2$O$_2$[M]$^+$: 202.0742, found: 202.0741.

[Preparation Example 2] Preparation of Methyl (4-methoxyquinolin-8-yl)carbamate

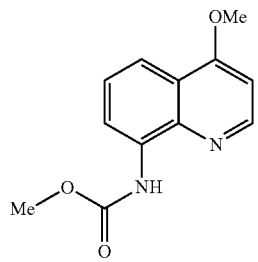 [SMILES: COC(=O)Nc1cccc2c(OC)ccnc12]

White solid (0.13 g, 56%, 2 steps yield); m.p. 151-153° C.; $^1$H NMR (600 MHz, CDCl$_3$) δ 9.21 (s, 1H), 8.63 (d, J=5.2 Hz, 1H), 8.41 (d, J=6.6 Hz, 1H), 7.80 (d, J=9.6 Hz, 1H), 7.47 (t, J=8.1 Hz, 1H), 6.77 (d, J=5.2 Hz, 1H), 4.05 (s, 3H), 3.84 (s, 3H); $^{13}$C NMR (150 MHz, CDCl$_3$) δ 162.5, 154.1, 149.1, 139.1, 134.4, 126.1, 121.0, 114.9, 114.6, 100.6, 55.8, 52.2; IR (cm$^{-1}$) 3366, 1719, 1527, 1411, 1232, 1023, 753, 634; HRMS (EI) m/z calcd. for C$_{12}$H$_{12}$N$_2$O$_3$ [M]$^+$: 232.0848, found: 232.0845.

[Preparation Example 3] Preparation of Methyl (6-methoxyquinolin-8-yl)carbamate

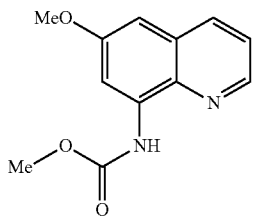 [SMILES: COC(=O)Nc1cc(OC)cc2cccnc12]

White solid (0.18 g, 76%, 2 steps yield); m.p. 82-84° C.; $^1$H NMR (600 MHz, CDCl$_3$) δ 9.17 (s, 1H), 8.62 (dd, J=4.1, 1.4 Hz, 1H), 8.14 (s, 1H), 8.01 (d, J=8.2 Hz, 1H), 7.38 (dd, J=8.2, 4.2 Hz, 1H), 6.74 (d, J=2.5 Hz, 1H), 3.92 (s, 3H), 3.85 (s, 3H); $^{13}$C NMR (150 MHz, CDCl$_3$) δ 158.5, 153.9, 145.5, 135.7, 134.9, 129.0, 122.0, 110.0, 107.1, 98.8, 55.5, 52.3; IR (cm$^{-1}$) 3364, 1728, 1529, 1221; HRMS (EI) m/z calcd. for C$_{12}$H$_{12}$N$_2$O$_3$ [M]$^+$: 232.0848, found: 232.0851.

[Preparation Example 4] Preparation of Methyl (5-methoxyquinolin-8-yl)carbamate

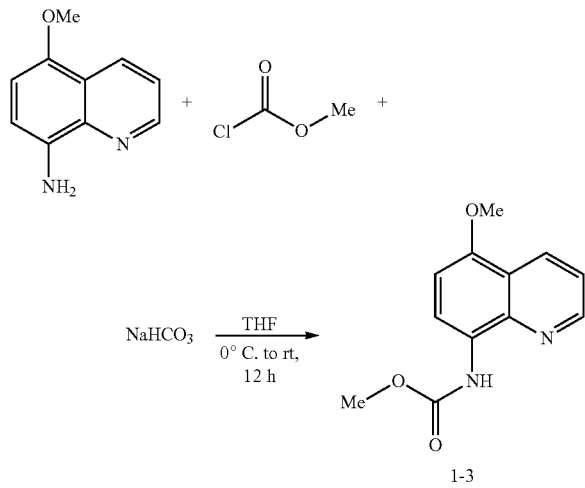

8-amino-5-methoxyquinoline (0.87 g, 5 mmol) and sodium bicarbonate (0.46 g, 5.5 mmol) were added to dried THF (20 mL) and cooled to 0° C. using an ice-bath, methyl chloroformate (0.42 mL, 5.5 mmol) was slowly added, and the reaction mixture was stirred at room temperature for 12 hours. The reaction mixture was filtered with celite (dichloromethane (15 mL×3)), distilled under reduced pressure, and separated and purified by column chromatography (eluent: n-hexane/EtOAc=4:1) to obtain quinoline ligand compound 1-3.

Light brown solid (0.95 g, 84%); m.p. 118-120° C.; $^1$H NMR (600 MHz, CD$_2$Cl$_2$) δ 8.86 (s, 1H), 8.78 (d, J=4.0 Hz, 1H), 8.54 (d, J=9.8 Hz, 1H), 8.26 (d, J=7.0 Hz, 1H), 7.43 (dd, J=8.4, 4.2 Hz, 1H), 6.85 (d, J=8.5 Hz, 1H), 3.96 (s, 3H), 3.78 (s, 3H); $^{13}$C NMR (150 MHz, CD$_2$Cl$_2$) δ 154.0, 149.7, 148.7, 138.8, 131.0, 128.0, 120.8, 120.5, 114.3, 104.3, 55.7, 52.0; IR (cm$^{-1}$) 3366, 1719, 1524, 1493, 1221, 1086, 837, 604; HRMS (EI) m/z calcd. for C$_{12}$H$_{12}$N$_2$O$_3$ [M]$^+$: 232.0848, found: 232.0848.

[Preparation Example 5] Preparation of Methyl (5-(trifluoromethyl)quinolin-8-yl)carbamate

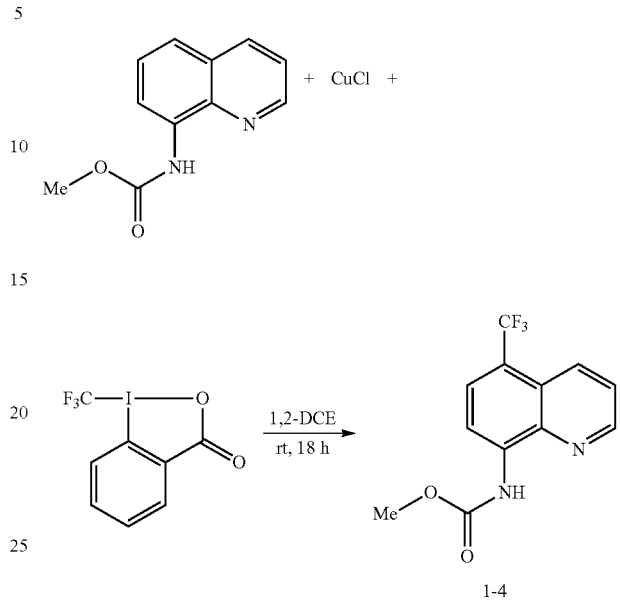

After methyl quinolin-8-ylcarbamate (404 mg, 2 mmol) was dissolved in 1,2-dichloroethane (20 mL) in a 100 mL round flask, CuCl (9.9 mg, 0.1 mmol, 5.0 mol %) and 1-trifluoromethyl-1,2-benziodoxol-3(1H)-one (632 mg, 2 mmol) were added thereto and the mixture was stirred at 25° C. for 18 hours. After the reaction was completed, the solvent was removed, and separation and purification were performed by column chromatography (n-hexane/ethyl acetate=10/1) to obtain desired quinoline ligand compound 1-4.

White solid (147 mg, 27%); m.p. 114-116° C.; $^1$H NMR (600 MHz, CDCl$_3$) δ 9.41 (s, 1H), 8.85 (d, J=4.0 Hz, 1H), 8.48 (d, J=8.6 Hz, 1H), 8.44 (d, J=8.0 Hz, 1H), 7.90 (d, J=8.2 Hz, 1H), 7.57 (dd, J=8.6, 4.1 Hz, 1H), 3.88 (s, 3H); $^{13}$C NMR (150 MHz, CDCl$_3$) δ 153.8, 148.5, 138.4, 137.9, 133.0 (q, J=2.4 Hz), 126.4 (q, J=5.8 Hz), 124.3 (q, J=272.4 Hz), 124.3, 122.8, 118.7 (q, J=31.0 Hz), 112.1, 52.6; $^{19}$F NMR (564 MHz, CDCl$_3$) δ-58.70 (s); IR (cm$^{-1}$) 3370, 1735, 1529, 1316, 1086, 858; HRMS (EI) m/z calcd. for C$_{12}$H$_9$F$_3$N$_2$O$_2$ [M]$^+$: 270.0616, found: 270.0613.

Example I: Preparation of Metal Complex

[Examples 1 to 4] Preparation of Metal Complexes C to F

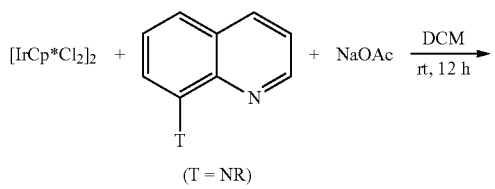

-continued

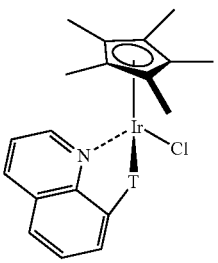

[IrCp*Cl₂]₂ (Cp*: pentamethylcyclopentadienyl) (0.20 g, 0.25 mmol), a quinoline ligand compound (0.50 mmol), sodium acetate (0.12 g, 1.5 mmol), and dichloromethane (10 mL) were added to a vial and the mixture was stirred at room temperature for 12 hours. After the reaction was completed, the reaction mixture was filtered with celite (dichloromethane (15 mL×3)), the solvent was removed by distillation under reduced pressure, and separation and purification were performed by column chromatography (n-hexane/acetone=2:1 to 1:1) to prepare metal catalysts C to F.

[Example 1] 8-(N-Tosyl)aminoquinoline Bound Cp*-Iridium Complex (Metal Catalyst C)

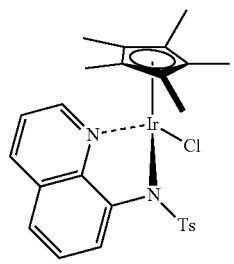

Orange solid (0.22 g, 66%); $^1$H NMR (600 MHz, CDCl₃) δ 8.66 (d, J=5.0 Hz, 1H), 8.10 (d, J=8.3 Hz, 2H), 7.98 (d, J=8.3 Hz, 1H), 7.39 (dd, J=8.3, 5.1 Hz, 1H), 7.34 (d, J=8.0 Hz, 1H), 7.22 (t, J=8.0 Hz, 1H), 7.04 (d, J=8.1 Hz, 2H), 6.89 (d, J=8.0 Hz, 1H), 2.22 (s, 3H), 1.68 (s, 15H); $^{13}$C NMR (150 MHz, CDCl₃) δ 149.3, 147.3, 145.2, 141.3, 138.0, 137.4, 129.7, 129.0, 128.9, 128.7, 122.2, 118.0, 116.6, 87.3 (Cp*), 21.3, 9.3 (Cp*); IR (cm⁻¹) 3051, 1462, 1375, 1299, 1138, 869, 655, 572; HRMS (EI) m/z calcd. for C₂₆H₂₈ClIrN₂O₂S [M]⁺: 660.1189, found: 660.1187.

[Example 2] 8-(N-Benzylamino)quinoline Bound Cp*-Iridium Complex (Metal Catalyst D)

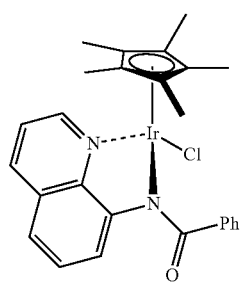

Orange solid (0.22 g, 70%); $^1$H NMR (400 MHz, CDCl₃) δ 8.67 (d, J=4.9 Hz, 1H), 8.03 (d, J=8.3 Hz, 1H), 7.91 (d, J=7.7 Hz, 2H), 7.38 (d, J=7.8 Hz, 2H), 7.28-7.22 (m, 3H), 7.19 (t, J=8.0 Hz, 1H), 6.98 (d, J=7.9 Hz, 1H), 1.45 (s, 15H); $^{13}$C NMR (150 MHz, CDCl₃) δ 177.6, 151.7, 148.8, 145.8, 140.2, 137.8, 130.0, 129.7, 129.4, 128.8, 127.7, 122.5, 122.0, 117.1, 86.9 (Cp*), 8.9 (Cp*); IR (cm⁻¹) 2914, 1599, 1501, 1373, 1316; HRMS (EI) m/z calcd. for C₂₆H₂₆ClIrN₂O [M]⁺: 610.1363, found: 610.1367.

[Example 3] 8-(N-Acetylamino)quinoline Bound Cp*-Iridium Complex (Metal Catalyst E)

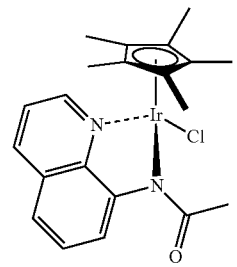

Yellow solid (0.19 g, 68%); $^1$H NMR (600 MHz, CDCl₃) δ 8.84 (d, J=8.0 Hz, 1H), 8.59 (d, J=4.9 Hz, 1H), 8.05 (d, J=8.2 Hz, 1H), 7.50 (t, J=8.0 Hz, 1H), 7.38 (dd, J=8.2, 5.0 Hz, 1H), 7.14 (d, J=8.0 Hz, 1H), 2.59 (s, 3H), 1.50 (s, 15H); $^{13}$C NMR (150 MHz, CDCl₃) δ 177.1, 150.2, 149.6, 146.3, 138.0, 129.8, 128.9, 123.3, 121.9, 118.4, 86.6 (Cp*), 28.8, 8.7 (Cp*); IR (cm⁻¹) 1602, 1492, 1365, 1315, 829, 762; HRMS (EI) m/z calcd. for C₂₁H₂₄ClIrN₂O [M]⁺: 548.1206, found: 548.1204.

[Example 4] 8-[N-(tert-Butyloxycarbonyl)amino]quinoline Bound Cp*-Iridium Complex (Metal Catalyst F)

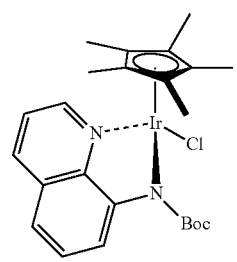

Orange solid (0.21 g, 70%); $^1$H NMR (600 MHz, CDCl₃) δ 8.61-8.57 (m, 1H), 8.35 (d, J=8.0 Hz, 1H), 8.01-7.95 (m, 1H), 7.47 (t, J=8.0 Hz, 1H), 7.34 (dd, J=8.3, 5.0 Hz, 1H), 7.02 (d, J=7.9 Hz, 1H), 1.56 (s, 24H); $^{13}$C NMR (150 MHz, CDCl₃) δ 158.6, 151.4, 149.4, 146.4, 137.6, 129.4, 129.1, 122.4, 121.8, 116.5, 86.2 (Cp*), 78.6, 28.9, 8.9 (Cp*); IR (cm⁻¹) 2970, 1652, 1447, 1296, 1154, 1108, 993, 761; HRMS (EI) m/z calcd. for C₂₄H₃₀ClIrN₂O₂[M]⁺: 606.1625, found: 606.1627.

[Examples 5 to 10] Preparation of Metal Complexes G to L

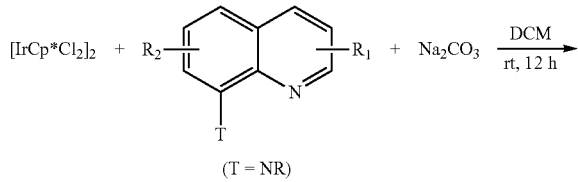

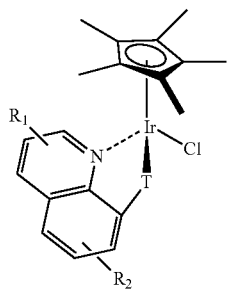

[IrCp*Cl$_2$]$_2$ (Cp*: pentamethylcyclopentadienyl) (0.20 g, 0.25 mmol), a quinoline ligand compound (0.50 mmol), sodium carbonate (0.16 g, 1.50 mmol), and dichloromethane (10 mL) were added to a vial and the mixture was stirred at room temperature for 12 hours. After the reaction was completed, the reactants were filtered with celite (dichloromethane (15 mL×3)), the solvent was removed by distillation under reduced pressure, and separation and purification were performed by column chromatography (n-hexane/acetone=2:1 to 1:1) to prepare metal catalysts G to L.

[Example 5] 8-[N-(Methyloxycarbonyl)amino]quinoline Bound Cp*-Iridium Complex (Metal Catalyst G)

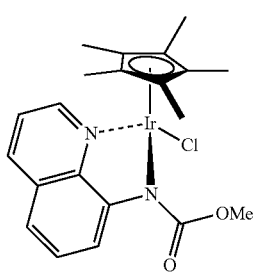

Yellow solid (0.24 g, 84%); $^1$H NMR (600 MHz, CDCl$_3$) δ 8.64 (dd, J=10.2, 6.6 Hz, 2H), 8.05 (d, J=8.2 Hz, 1H), 7.51 (t, J=8.0 Hz, 1H), 7.34 (dd, J=8.2, 5.1 Hz, 1H), 7.09 (d, J=7.9 Hz, 1H), 3.75 (s, 3H), 1.57 (s, 15H); $^{13}$C NMR (150 MHz, CDCl$_3$) δ 159.7, 150.7, 148.9, 145.8, 137.8, 129.7, 129.5, 121.8, 121.7, 117.1, 86.6 (Cp*), 52.6, 8.9 (Cp*); IR (cm$^{-1}$) 1645, 1500, 1376, 1302, 1174, 1030, 831; HRMS (EI) m/z calcd. for C$_{21}$H$_{24}$ClIrN$_2$O$_2$[M]$^+$: 564.1156, found: 564.1157.

[Example 6] 8-[N—(N,N-Dimethylaminocarbonyl)amino]quinoline Bound Cp*-Iridium Complex (Metal Catalyst H)

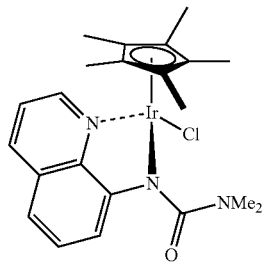

Red solid (0.15 g, 51%); $^1$H NMR (400 MHz, CDCl$_3$) δ 8.47 (d, J=5.0 Hz, 1H), 7.92 (d, J=8.4 Hz, 1H), 7.34-7.28 (m, 2H), 6.93 (d, J=8.0 Hz, 1H), 6.68 (d, J=7.9 Hz, 1H), 3.17 (s, 6H), 1.62 (s, 15H); $^{13}$C NMR (150 MHz, CDCl$_3$, two carbons merged to others) δ 166.5, 154.8, 147.0, 145.0, 137.7, 130.5, 129.9, 121.7, 115.6, 111.6, 86.0 (Cp*), 8.4 (Cp*); IR (cm$^{-1}$) 2910, 1622, 1460, 1358, 1327, 1150, 811, 772; HRMS (EI) m/z calcd. for C$_{22}$H$_{27}$ClIrN$_3$O [M]$^+$: 577.1472, found: 577.1475.

[Example 7] 8-[N-(Methyloxycarbonyl)amino]-5-trifluoromethyl quinoline Bound Cp*-Iridium Complex (Metal Catalyst I)

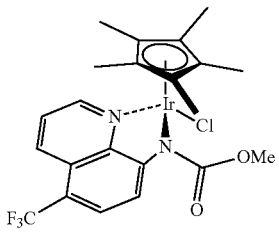

Orange solid (0.22 g, 70%); $^1$H NMR (600 MHz, CDCl$_3$) δ 8.73 (d, J=5.1 Hz, 1H), 8.61 (d, J=8.6 Hz, 1H), 8.37 (d, J=8.7 Hz, 1H), 7.86 (d, J=8.7 Hz, 1H), 7.49 (dd, J=8.7, 5.1 Hz, 1H), 3.77 (s, 3H), 1.57 (s, 15H); $^{13}$C NMR (150 MHz, CDCl$_3$) δ 159.6, 154.4, 149.6, 145.8, 134.6, 128.7 (q, J=5.2 Hz), 126.2, 124.2 (q, J=271.9 Hz), 123.0, 119.0, 115.0 (q, J=31.4 Hz), 86.9 (Cp*), 52.9, 8.9 (Cp*); $^{19}$F NMR (564 MHz, CDCl$_3$) δ-58.08 (s); IR (cm$^{-1}$) 1660, 1511, 1314, 1285, 1133, 1098, 847; HRMS (EI) m/z calcd. for C$_{22}$H$_{23}$ClF$_3$IrN$_2$O$_2$ [M]$^+$: 632.1029, found: 632.1031.

[Example 8] 4-Methoxy-8-[N-(methyloxycarbonyl)amino]quinoline Bound Cp*-Iridium Complex (Metal Catalyst J)

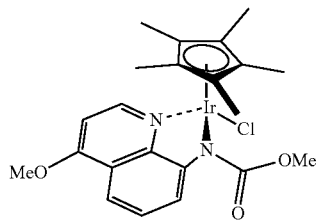

Yellow solid (0.24 g, 80%); $^1$H NMR (600 MHz, CDCl$_3$) δ 8.65 (d, J=8.0 Hz, 1H), 8.52 (d, J=6.0 Hz, 1H), 7.43 (t, J=8.1 Hz, 1H), 7.33 (d, J=8.8 Hz, 1H), 6.50 (d, J=6.0 Hz, 1H), 3.80 (s, 3H), 3.75 (s, 3H), 1.55 (s, 15H); $^{13}$C NMR (150

MHz, CDCl$_3$) δ 163.5, 159.8, 150.4, 150.3, 146.0, 128.4, 121.9, 121.7, 111.4, 101.7, 86.1 (Cp*), 56.1, 52.6, 8.9 (Cp*); IR (cm$^{-1}$) 1641, 1513, 1410, 1308, 1198, 1028, 750; HRMS (EI) m/z calcd. for C$_{22}$H$_{26}$ClIrN$_2$O$_3$ [M]$^+$: 594.1261, found: 594.1261.

[Example 9] 5-Methoxy-8-[N-(methyloxycarbonyl)amino]quinoline Bound Cp*-Iridium Complex (Metal Catalyst K)

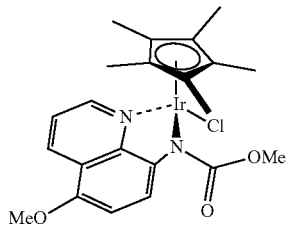

Orange solid (0.27 g, 91%); $^1$H NMR (600 MHz, CDCl$_3$) δ 8.66 (d, J=4.8 Hz, 1H), 8.59 (d, J=8.8 Hz, 1H), 8.46 (d, J=8.4 Hz, 1H), 7.35 (dd, J=8.3, 5.0 Hz, 1H), 6.95 (d, J=8.8 Hz, 1H), 3.96 (s, 3H), 3.73 (s, 3H), 1.56 (s, 15H); $^{13}$C NMR (150 MHz, CDCl$_3$) δ 159.6, 149.6, 147.5, 145.9, 143.9, 132.9, 121.2, 120.9, 120.8, 107.2, 86.4 (Cp*), 56.2, 52.5, 8.9 (Cp*); IR (cm$^{-1}$) 1645, 1571, 1470, 1378, 1323, 1295, 1093; HRMS (EI) m/z calcd. for C$_{22}$H$_{26}$ClIrN$_2$O$_3$[M]$^+$: 594.1261, found: 594.1260.

[Example 10] 6-Methoxy-8-[N-(methyloxycarbonyl)amino]quinoline Bound Cp*-Iridium Complex (Metal Catalyst L)

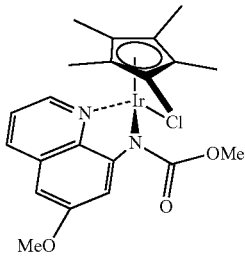

Yellow solid (0.24 g, 81%); $^1$H NMR (600 MHz, CDCl$_3$) δ 8.45 (d, J=5.0 Hz, 1H), 8.39 (d, J=2.3 Hz, 1H), 7.90 (d, J=8.3 Hz, 1H), 7.29-7.24 (m, 1H), 6.51 (d, J=2.2 Hz, 1H), 3.89 (s, 3H), 3.75 (s, 3H), 1.56 (s, 15H); $^{13}$C NMR (150 MHz, CDCl$_3$) δ 160.9, 159.7, 151.8, 146.2, 142.8, 136.2, 129.7, 122.2, 112.2, 97.2, 86.5 (Cp*), 55.7, 52.7, 8.9 (Cp*); IR (cm$^{-1}$) 1637, 1572, 1497, 1378, 1296, 1258, 1054, 724; HRMS (EI) m/z calcd. for C$_{22}$H$_{26}$ClIrN$_2$O$_3$[M]$^+$: 594.1261, found: 594.1260.

[Example 11] Preparation of Metal Complex M

[Ru(p-cymene)Cl$_2$]$_2$ (122 mg, 0.20 mmol), methyl (5-methoxyquinolin-8-yl)carbamate (92 mg, 0.40 mmol), sodium carbonate (126 mg, 1.50 mmol), and dichloromethane (10 mL) were added to a vial and the mixture was stirred at room temperature for 12 hours. After the reaction was completed, the reaction mixture was filtered with celite and washed (dichloromethane (15 mL×3)), the solvent was removed under reduced pressure, and the residue was separated and purified by column chromatography (n-hexane/acetone=2:1 to 1:1) to prepare the following metal catalyst M.

5-Methoxy-8-[N-(methyloxycarbonyl)amino]quinoline Bound p-cymene-ruthenium Complex (Metal Catalyst M)

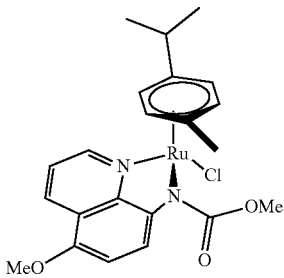

Orange solid (150 mg, 75%); $^1$H NMR (600 MHz, CDCl$_3$) δ 9.07 (d, J=4.8 Hz, 1H), 8.70 (d, J=8.8 Hz, 1H), 8.48 (d, J=8.2 Hz, 1H), 7.32 (dd, J=8.2, 5.1 Hz, 1H), 6.87 (d, J=8.8 Hz, 1H), 5.71 (d, J=5.9 Hz, 1H), 5.31 (d, J=5.9 Hz, 1H), 5.24 (t, J=6.2 Hz, 2H), 3.91 (s, 3H), 3.80 (s, 3H), 2.46 (hept, J=7.0 Hz, 1H), 2.29 (s, 3H), 0.96 (d, J=6.9 Hz, 3H), 0.87 (d, J=6.8 Hz, 3H); $^{13}$C NMR (150 MHz, CDCl$_3$) δ 160.8, 151.4, 146.6, 145.0, 143.6, 132.6, 120.8, 120.7, 120.6, 107.5, 103.1, 100.1, 86.2, 84.5, 82.9, 82.7, 56.2, 52.1, 30.8, 22.2, 22.0, 19.0.

[Example 12] Preparation of Metal Complex N

[RhCp*Cl$_2$]$_2$ (77 mg, 0.125 mmol), methyl (5-methoxyquinolin-8-yl)carbamate (58 mg, 0.25 mmol), sodium carbonate (79.5 mg, 0.75 mmol), and dichloromethane (5 mL) were added to a vial and the mixture was stirred at room temperature for 12 hours. After the reaction was completed, the reaction mixture was filtered with celite and washed (dichloromethane (15 mL×3)), the solvent was removed under reduced pressure, and recrystallization was performed with a small amount of acetone at −30° C. to prepare the following metal catalyst N.

5-Methoxy-8-{N-(methyloxycarbonyl)amino}quinoline Bound Cp*-rhodium Complex (Metal Catalyst N)

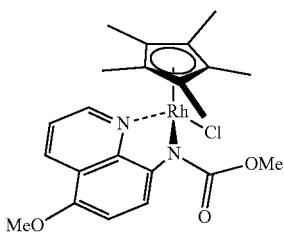

Orange solid (90 mg, 71%); $^1$H NMR (600 MHz, CDCl$_3$) δ 8.71 (d, J=4.9 Hz, 1H), 8.60 (d, J=8.7 Hz, 1H), 8.51 (d, J=8.3 Hz, 1H), 7.39 (dd, J=8.4, 5.0 Hz, 1H), 6.89 (d, J=8.7

Hz, 1H), 3.93 (s, 3H), 3.73 (s, 3H), 1.54 (s, 15H); $^{13}$C NMR (150 MHz, CDCl$_3$) δ 160.3, 150.0, 146.9, 145.5, 143.3, 132.9, 121.1, 120.9, 120.7, 107.4, 94.5, 94.4, 56.2, 52.0, 8.9.

[Example 13] Preparation of Metal Complex O

[CoCp*Cl$_2$]$_2$ (66 mg, 0.125 mmol), methyl (5-methoxyquinolin-8-yl)carbamate (58 mg, 0.25 mmol), potassium hydroxide (42 mg, 0.75 mmol), and dichloromethane (5 mL) were added to a vial and the mixture was stirred at room temperature for 12 hours. After the reaction was completed, the reaction mixture was filtered with celite and washed (dichloromethane (15 mL×3)), the solvent was removed under reduced pressure, and recrystallization was performed with a small amount of acetone at −30° C. to prepare the following metal catalyst O.

5-Methoxy-8-{N-(methyloxycarbonyl)amino}quinoline Bound Cp*-cobalt Complex (Metal Complex O)

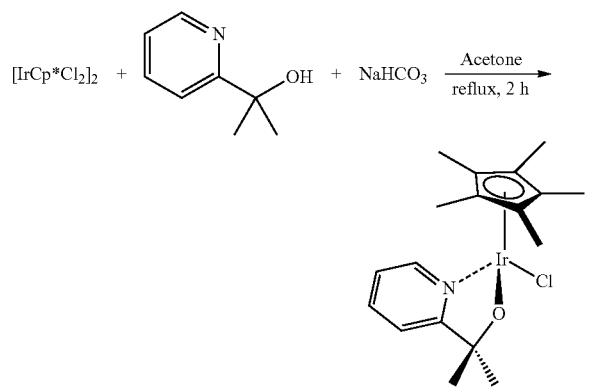

Green solid (34 mg, 30%); $^1$H NMR (600 MHz, CD$_2$Cl$_2$) δ 9.24 (dd, J=5.1, 1.4 Hz, 1H), 8.53 (dd, J=8.4, 1.4 Hz, 1H), 8.36 (d, J=8.6 Hz, 1H), 7.56 (dd, J=8.4, 5.1 Hz, 1H), 6.88 (d, J=8.6 Hz, 1H), 3.95 (s, 3H), 3.73 (s, 3H), 1.10 (s, 15H).

[Comparative Example 1] Preparation of Metal Complex A

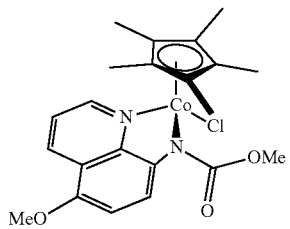

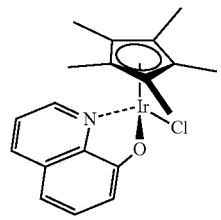

[IrCp*Cl$_2$]$_2$ (0.4106 g, 0.5154 mmol), 2-(2'-pyridyl)-2-propanol (0.1420 g, 1.036 mmol), sodium bicarbonate (0.345 g, 4.11 mmol), and acetone (50 mL) were added to a vial and the mixture was stirred at room temperature for 2 hours. After the reaction was completed, the reactants were filtered with celite (dichloromethane (15 mL×3)), the solvent was removed by distillation under reduced pressure, and separation and purification were performed by column chromatography (n-hexane/acetone=2:1 to 1:1) to prepare metal catalyst A.

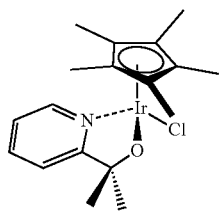

Yellow solid (0.416 g, 81%); $^1$H NMR (400 MHz, MeOD) δ 8.69 (dt, J=5.2, 1.3 Hz, 1H), 7.88 (td, J=7.9, 1.5 Hz, 1H), 7.46-7.31 (m, 2H), 1.67 (s, 15H), 1.46 (s, 6H); $^{13}$C NMR (150 MHz, MeOD) δ 177.34, 150.97, 139.53, 125.54, 122.95, 85.97, 84.74, 33.67, 9.01.

[Comparative Example 2] Preparation of Metal Complex B

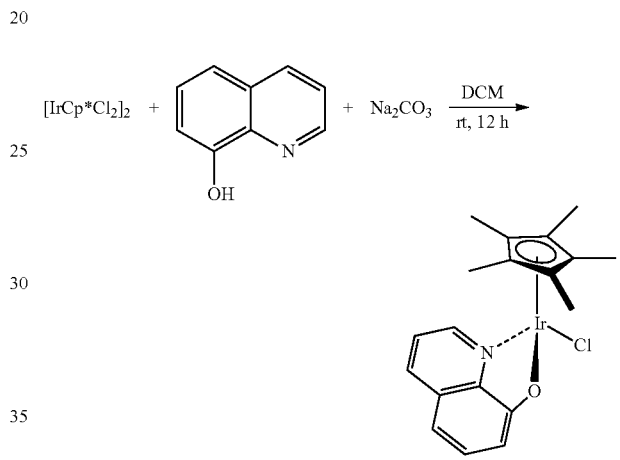

[IrCp*Cl$_2$]$_2$ (0.20 g, 0.25 mmol), quinolin-8-ol (72.6 mg, 0.50 mmol), sodium carbonate (0.21 g, 2.0 mmol), and acetone (10 mL) were added to a vial and the mixture was stirred at room temperature for 12 hours. After the reaction was completed, the reactants were filtered with celite (dichloromethane (15 mL×3)), the solvent was removed by distillation under reduced pressure, and separation and purification were performed by column chromatography (n-hexane/acetone=2:1 to 1:1) to prepare metal catalyst B.

8-Hydroxyquinoline Bound Cp*-iridium Complex (Metal Catalyst B)

Orange solid (0.20 g, 80%); $^1$H NMR (600 MHz, CDCl$_3$) δ 8.54 (d, J=4.9 Hz, 1H), 8.03 (d, J=8.3 Hz, 1H), 7.36 (t, J=7.9 Hz, 1H), 7.30 (dd, J=8.3, 4.9 Hz, 1H), 7.00 (d, J=7.9 Hz, 1H), 6.78 (d, J=7.9 Hz, 1H), 1.73 (s, 15H); $^{13}$C NMR (150 MHz, CDCl$_3$) δ 169.1, 146.0, 145.8, 137.7, 131.0, 130.7, 121.9, 115.6, 110.9, 84.8 (Cp*), 8.9 (Cp*); IR (cm$^{-1}$) 1564, 1455, 1367, 1320, 1111, 826, 751, 512; HRMS (EI) m/z calcd. for $C_{19}H_{21}ClIrNO$ [M]$^+$: 507.0941, found: 507.0943.

Preparation Example II: Preparation of Carboxylic Acid Compound

[Preparation Example 6] Preparation of 2-ethylbenzoic Acid

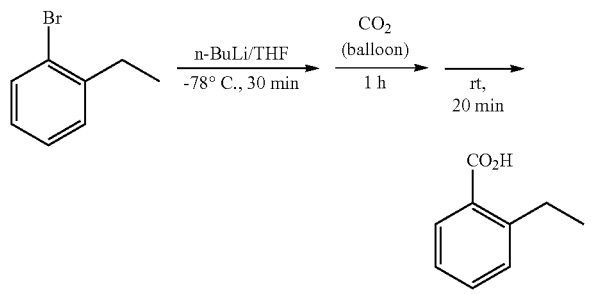

1-bromo-2-ethylbenzene (1.38 ml, 10 mmol) was dissolved in THF (30 mL), and n-BuLi (2.5 M in hexane, 6.0 ml, 15 mmol) was slowly added thereto at −78° C. Thereafter, the mixture was stirred at the same temperature for 30 minutes and then anhydrous $CO_2$ was bubbled for 1 hour. The temperature of the reaction mixture was raised again, and the mixture was stirred at room temperature for 20 minutes, quenched with a saturated aqueous $NaHCO_3$ solution, and washed with $Et_2O$. An aqueous solution layer was acidified with a 1 N aqueous HCl solution, and then extracted with $Et_2O$. The extracted solution was dried and concentrated to obtain 2-ethylbenzoic acid as a white solid (0.77 g, 50%).

[Preparation Example 7] Preparation of (S)-2-(1,3-dioxoisoindolin-2-yl)-4-methylpentanoic Acid and (S)-2-(1,3-dioxoisoindolin-2-yl)-4-phenylbutanoic Acid

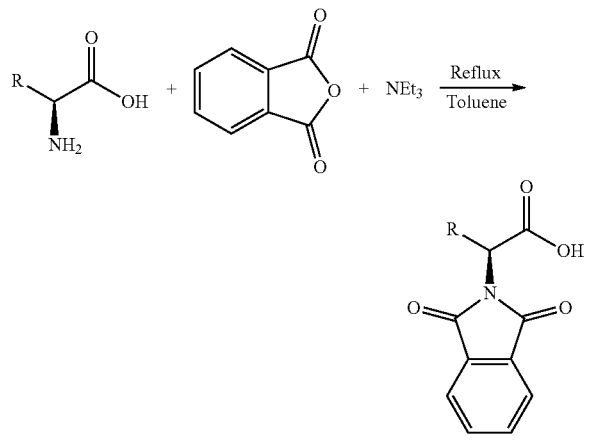

α-Amino acid (20 mmol), phthalic anhydride (3.0 g, 20 mmol), and triethylamine ($Et_3N$, 0.28 mL, 2 mmol) were added to toluene (20 mL). The reaction mixture was heated at 130° C. for 4 hours, and moisture produced during the reaction was collected by a water separator. The reaction mixture was cooled to room temperature, the solvent was removed under reduced pressure, and the reactants were dissolved in DCM (150 mL) and washed twice with an aqueous HCl solution (0.5-1.0 M, 100 mL) and three times with a saline (100 mL). The collected organic layer was dried with anhydrous $MgSO_4$, filtered with celite using DCM (30 mL), and distilled under reduced pressure to prepare a carboxylic acid protected by phthalimido with a yield of 95% or more.

[Preparation Example 8] Preparation of (R)-3-(1,3-dioxoisoindolin-2-yl)-4-methylpentanoic Acid

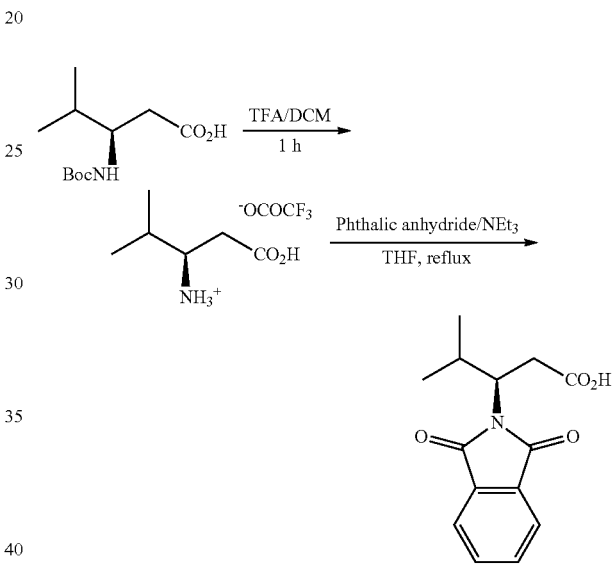

A mixed solution of Boc-β-leucine (0.75 g, 3.3 mmol) and trifluoroacetic acid/dichloromethane (TFA/DCM, 10 mL, 1:1) was added to a round flask and the solution was stirred for 1 hour. The reaction mixture was concentrated under reduced pressure to remove TFA, and the residue was triturated with toluene (3 mL) and then concentrated. A β-alanine TFA salt was dissolved in THF (15 mL), $Et_3N$ (0.66 g, 6.5 mmol) and phthalic anhydride (0.49 g, 3.3 mmol) were added thereto, and the reactants were heated to reflux overnight under an argon atmosphere. The reaction mixture was cooled to room temperature and concentrated under vacuum, and the residue was diluted with 1 N HCl (10 mL) and extracted with EtOAc (60 mL). The extracted organic layer was washed with a saline, dried with $Na_2SO_4$, and concentrated. The concentrated residue was separated and purified with column chromatography (DCM/MeOH, 9:1) to obtain (R)-3-(1,3-dioxoisoindolin-2-yl)-4-methylpentanoic acid as a colorless oil (0.40 g, 47%).

A carboxylic acid compound other than the carboxylic acid prepared by the above method was purchased from Aldrich, Alfa, TCI, or the like and used without separate purification.

Preparation Example III: Preparation of Hydroxamic Acid Compound

Method A. One-Pot Synthesis of Hydroxamic Acids from Carboxylic Acids

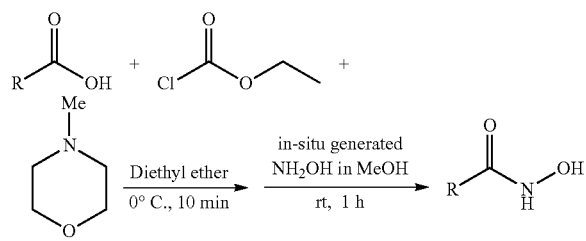

Preparation of in-situ generated hydroxylamine: A solution of hydroxylamine hydrochloride (1.0 g, 15 mmol) dissolved in methanol (10 mL) at 0° C. was added to a solution of potassium hydroxide (0.84 g, 15 mmol) dissolved in methanol (4 mL) and then the solution was stirred at the same temperature for 15 minutes. Precipitated potassium chloride was removed, and then the produced filtrate was used in the next reaction without purification.

A carboxylilc acid compound (10 mmol) was dissolved in diethyl ether (30 mL), ethylchloroformate (1.3 g, 12 mmol) and N-methylmorpholine (1.3 g, 13 mmol) were added thereto at 0° C., and then the reaction mixture was stirred for 10 minutes. After removing a solid by filtration, the filtrate was added to a hydroxylamine (0.5 g, 15 mmol) solution dissolved in methanol (in-situ generated hydroxylamine) and the solution was stirred at room temperature for 15 minutes to proceed with the reaction. The solvent was removed, and the residue was separated and purified by column chromatography (eluent: n-hexane/EtOAc, 1:1 to 1:5) to obtain the desired hydroxamic acid compound.

Method B. One-Pot Synthesis of Hydroxamic Acids from Carboxylic Acids

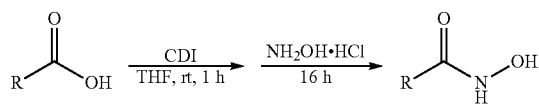

A carboxylic acid compound (10 mmol) was added to dried tetrahydrofuran (THF, 30 mL), 1,1'-Carbonyldiimidazole (CDI, 15 mmol, 1.5 equiv) was added thereto, and the mixture was stirred for 1 hour. Hydroxylamine hydrochloride (1.39 g, 20 mmol) in a powder form was added and the mixture was stirred for 16 hours. After the reaction was completed, the reaction mixture was added to a 5% aqueous $KHSO_4$ solution (30 mL), and extracted with EtOAc (2×30 mL). The collected organic layer was washed with a saline (50 mL), dried with $MgSO_4$, concentrated, and separated and purified by column chromatography (eluent: n-hexane/EtOAc, 1:1 to 1:5) to obtain the desired hydroxamic acid compound.

Method C. Synthesis of Hydroxamic Acids from Ester

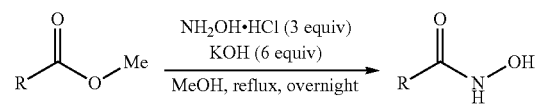

A methyl ester compound (10.0 mmol) and hydroxylamine hydrochloride (2.08 g, 30 mmol, 3.0 equiv) were dissolved in methanol (50 mL). Solid hydroxylamine hydrochloride (3.37 g, 60 mmol, 6.0 equiv) was added thereto and heated to reflux for 24 hours. 1 N HCl was added to the reaction mixture to adjust pH to 4 and concentrated to remove methanol. Water (50 mL) was added to the residue and extracted with EtOAc (3×50 mL). The collected organic layer was dried with $MgSO_4$ and concentrated, and then separated and purified with column chromatography (eluent: n-hexane/EtOAc, 1:1 to 1:5) to obtain the desired hydroxamic acid compound.

Method D. One-Pot Synthesis of Hydroxamic Acids from Carboxylic Acids

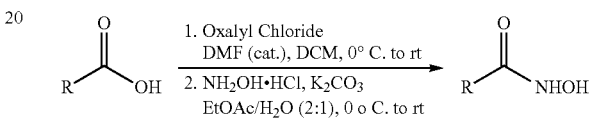

A carboxylic acid compound (2.0 mmol) was dissolved in dichloromethane (30 mL), and then oxalyl chloride (4.0 mmol) and DMF (2 drops) were added at 0° C. This mixture was stirred at room temperature for 2.5 to 4 hours. After the solvent was removed under reduced pressure, the residue was directly used in the next reaction without purification.

Hydroxylamine hydrochloride (1.2 equiv) and $K_2CO_3$ (2.0 equiv) were dissolved in a solvent in which water (8 mL) and EtOAc (16 mL) were mixed at 1:2, and then cooled to 0° C. In this solution, the acid chloride prepared above dissolved in a minimal amount of ethyl acetate was dissolved and then the reaction mixture was stirred at room temperature for 12 hours. An organic layer and an aqueous solution layer were separated, and then the aqueous solution layer was extracted with EA. The collected organic layer was dried with anhydrous $MgSO_4$, concentrated, and separated and purified by column chromatography (eluent: DCM/methanol=30:1 to 10:1) to obtain the desired hydroxamic acid compound.

[Preparation Example 9] Preparation of 4-phenylbutanyl Hydroxamic Acid

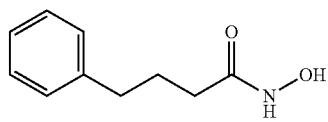 [SMILES: O=C(CCCc1ccccc1)NO]

Prepared from 4-phenylbutyric acid (2 mmol scale) by Method B; White solid (0.34 g, 95%); $^1$H NMR (600 MHz, $CDCl_3$) δ 8.50 (br, 2H), 7.28-7.24 (m, 2H), 7.18 (t, J=7.4 Hz, 1H), 7.14 (d, J=7.4 Hz, 2H), 2.61 (t, J=7.6 Hz, 2H), 2.11 (t, J=7.6 Hz, 2H), 1.94 (p, J=7.5 Hz, 2H); $^{13}$C NMR (150 MHz, $CDCl_3$) δ 171.4, 140.9, 128.4, 128.4, 126.1, 34.9, 32.1, 26.7.

[Preparation Example 10] Preparation of 4-(4-bromophenyl)butanyl Hydroxamic Acid

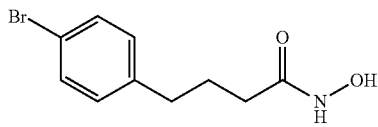 [SMILES: O=C(CCCc1ccc(Br)cc1)NO]

Prepared from 4-(4-bromophenyl)butyric acid (2.0 mmol scale) by Method B; solid (0.50, 96%); m.p. 99-101° C.; $^1$H NMR (600 MHz, CDCl$_3$) δ 8.15 (s, 2H), 7.40 (d, J=7.9 Hz, 2H), 7.03 (d, J=7.9 Hz, 2H), 2.59 (t, J=7.6 Hz, 2H), 2.13 (t, J=7.5 Hz, 2H), 1.95 (p, J=7.5 Hz, 2H); $^{13}$C NMR (150 MHz, CDCl$_3$) δ 170.8, 139.8, 131.5, 130.1, 119.9, 34.2, 31.8, 26.4; IR (cm$^{-1}$) 3206, 3037, 2896, 1623, 1486, 1071, 1009; HRMS (EI) m/z calcd. for C$_{10}$H$_{12}$BrNO$_2$ [M]$^+$: 257.0051, found: 257.0049.

[Preparation Example 11] Preparation of 4-(4-fluorophenyl)butanyl Hydroxamic Acid

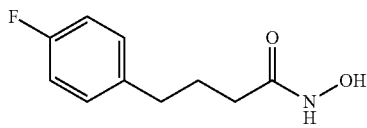 [SMILES: O=C(CCCc1ccc(F)cc1)NO]

Prepared from 4-(4-fluorophenyl)butyric acid (5 mmol scale) by Method B: White solid (0.71 g, 72%); m.p. 48-50° C.; $^1$H NMR (600 MHz, acetone-d$_6$) δ 9.98 (s, 1H), 8.24 (s, 1H), 7.27-7.17 (m, 2H), 7.01 (t, J=8.8 Hz, 2H), 2.60 (t, J=7.6 Hz, 2H), 2.11 (t, J=7.5 Hz, 2H), 1.88 (p, J=7.5 Hz, 2H); $^{13}$C NMR (150 MHz, acetone-d$_6$) δ 170.3, 161.2 (d, J=241.4 Hz), 137.8, 130.0 (d, J=8.0 Hz), 114.8 (d, J=21.1 Hz), 33.9, 31.6, 27.2; $^{19}$F NMR (564 MHz, acetone-d$_6$) δ-119.2 (m); IR (cm$^{-1}$) 3167, 2907, 1607, 1507, 1222, 1068, 820; HRMS (EI) m/z calcd. for C$_{10}$H$_{12}$FNO$_2$ [M]$^+$: 197.0852, found: 197.0850.

[Preparation Example 12] Preparation of 4-(4-nitrophenyl)butanyl Hydroxamic Acid

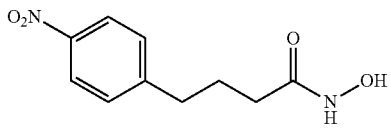 [SMILES: O=C(CCCc1ccc([N+](=O)[O-])cc1)NO]

Prepared from 4-(4-nitrophenyl)butyric acid (2.0 mmol scale) by Method B: White solid (0.43 g, 95%); m.p. 109-111° C.; $^1$H NMR (600 MHz, DMSO-d$_6$) δ 10.33 (s, 1H), 8.66 (s, 1H), 8.13 (d, J=8.7 Hz, 2H), 7.45 (d, J=8.4 Hz, 2H), 2.67 (t, J=7.8 Hz, 2H), 1.95 (t, J=7.4 Hz, 2H), 1.80 (q, J=7.6 Hz, 2H); $^{13}$C NMR (150 MHz, DMSO-d$_6$) δ 169.0, 150.6, 146.3, 130.1, 123.9, 34.7, 32.0, 26.8; IR (cm$^{-1}$) 3187, 3037, 2902, 1628, 1510, 1346, 849; HRMS (EI) m/z calcd. for C$_{10}$H$_{12}$N$_2$O$_4$ [M]$^+$: 224.0797, found: 224.0795.

[Preparation Example 13] Preparation of 4-(4-methoxyphenyl)butanyl Hydroxamic Acid

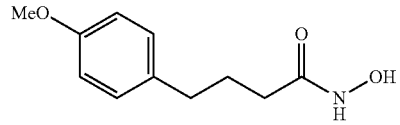 [SMILES: COc1ccc(CCCC(=O)NO)cc1]

Prepared from 4-(4-methoxyphenyl)butyric acid (2.0 mmol scale) by Method B; White solid (0.41 g, 97%); m.p. 97-99° C.; $^1$H NMR (600 MHz, CDCl$_3$) δ 8.56 (br, 1H), 8.25 (s, 1H), 7.06 (d, J=8.5 Hz, 2H), 6.82 (d, J=8.7 Hz, 2H), 3.78 (s, 3H), 2.57 (t, J=7.5 Hz, 2H), 2.11 (t, J=7.3 Hz, 2H), 1.94 (q, J=7.6 Hz, 2H); $^{13}$C NMR (150 MHz, CDCl$_3$) δ 171.3, 157.9, 132.9, 129.3, 113.9, 55.2, 33.9, 32.0, 26.8; IR (cm$^{-1}$) 3216, 3034, 2900, 1609, 1509, 1241, 1028; HRMS (EI) m/z calcd. for C$_{11}$H$_{15}$NO$_3$ [M]$^+$: 209.1052, found: 209.1052.

[Preparation Example 14] Preparation of tert-butyl [4-{4-(hydroxyamino)-4-oxobutyl}phenyl]carbamate

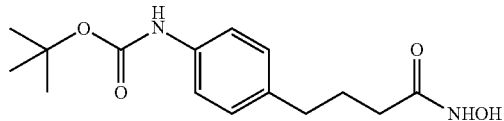

Prepared by Method A (2.0 mmol scale); White solid (0.44 g, 78%); m.p. 120-122° C.; $^1$H NMR (400 MHz, CDCl$_3$) δ 10.32 (s, 1H), 9.20 (s, 1H), 8.66 (s, 1H), 7.30 (d, J=8.1 Hz, 2H), 7.00 (d, J=8.5 Hz, 2H), 2.40 (t, J=7.6 Hz, 2H), 1.89 (t, J=7.4 Hz, 2H), 1.69 (p, J=7.8 Hz, 2H), 1.42 (s, 9H); $^{13}$C NMR (150 MHz, CDCl$_3$) δ 169.3, 153.3, 137.7, 135.6, 128.8, 118.7, 79.2, 34.4, 32.2, 28.6, 27.5; IR (cm$^{-1}$) 3343, 3286, 1695, 1624, 1523, 1239, 1162; HRMS (FAB) m/z calcd. for C$_{15}$H$_{22}$N$_2$O$_4$ [M+H]$^+$: 295.1658, found: 295.1661.

[Preparation Example 15] Preparation of 2,2-dimethyl-4-phenylbutanyl Hydroxamic Acid

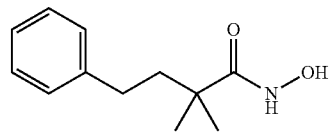

Prepared from 2,2-dimethyl-4-phenylbutanoic acid by Method D; White solid (0.89 g, 93%); m.p. 131-133° C.; $^1$H NMR (600 MHz, CDCl$_3$) δ 8.42 (br, 2H), 7.28-7.24 (m, 3H), 7.16 (dd, J=19.0, 7.4 Hz, 3H), 2.56-2.49 (m, 2H), 1.87-1.80 (m, 2H), 1.24 (s, 6H); $^{13}$C NMR (150 MHz, CDCl$_3$) δ 175.5, 141.7, 128.4, 128.3, 125.9, 42.8, 40.1, 31.2, 24.6; IR (cm$^{-1}$) 3250, 2920, 1606, 1516, 1492, 697; HRMS (EI) m/z calcd. for C$_{12}$H$_{17}$NO$_2$ [M]$^+$: 207.1259, found: 207.1261.

[Preparation Example 16] Preparation of 2-methyl-4-phenylbutanyl Hydroxamic Acid

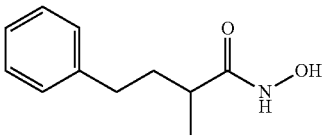

Prepared from 2-methyl-4-phenylbutanoic acid by Method D: White solid (0.34 g, 88%); m.p. 126-128° C.; $^1$H NMR (400 MHz, acetone-$d_6$) δ 10.09 (s, 1H), 8.42 (s, 1H), 7.25-7.20 (m, 2H), 7.18-7.08 (m, 3H), 2.60-2.46 (m, 2H), 2.31-2.19 (m, 1H), 1.96-1.83 (m, 1H), 1.72-1.53 (m, 1H), 1.08 (d, J=6.9 Hz, 3H); $^{13}$C NMR (151 MHz, acetone-$d_6$, one carbon merged to others) δ 173.4, 142.0, 128.2, 125.7, 37.0, 35.7, 33.3, 17.4; IR (cm$^{-1}$) 3201, 3027, 2918, 1620, 1453, 1033, 697; HRMS (EI) m/z calcd. for $C_{11}H_{15}NO_2$ [M]$^+$: 193.1103, found: 193.1103.

[Preparation Example 17] Preparation of 3-methyl-4-phenylbutanyl Hydroxamic Acid

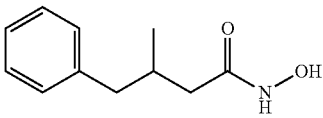

Prepared from 3-methyl-4-phenylbutanoic acid by Method B; White solid (1.24 g, 68%); m.p. 75-77° C.; $^1$H NMR (600 MHz, CDCl$_3$) δ 8.53 (br, 2H), 7.26 (t, J=7.2 Hz, 2H), 7.19 (t, J=7.2 Hz, 1H), 7.12 (d, J=7.2 Hz, 2H), 2.59 (dd, J=13.2, 6.5 Hz, 1H), 2.47 (dd, J=13.1, 7.8 Hz, 1H), 2.30-2.23 (m, 1H), 2.14 (dd, J=14.1, 4.9 Hz, 1H), 1.90-1.84 (m, 1H), 0.90 (d, J=6.4 Hz, 3H); $^{13}$C NMR (150 MHz, CDCl$_3$) δ 170.8, 139.9, 129.1, 128.3, 126.1, 43.0, 39.6, 32.4, 19.3; IR (cm$^{-1}$) 3208, 2920, 1632, 1453, 1030, 698; HRMS (EI) m/z calcd. for $C_{11}H_{15}NO_2$ [M]$^+$: 193.1103, found: 193.1100.

[Preparation Example 18] Preparation of 2-(2,3-dihydro-1H-inden-2-yl)acetyl Hydroxamic Acid

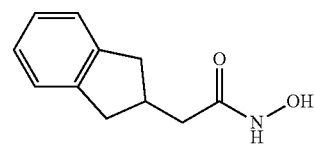 [SMILES: O=C(CC1Cc2ccccc2C1)NO]

Prepared from 2-indanylacetic acid by Method A: White solid (0.34 g, 89%); m.p. 142-144° C.; $^1$H NMR (600 MHz, DMSO-$d_6$) δ 10.36 (s, 1H), 8.70 (s, 1H), 7.19-7.15 (m, 2H), 7.10-7.06 (m, 2H), 2.97 (dd, J=15.7, 7.8 Hz, 2H), 2.71 (dt, J=14.9, 7.3 Hz, 1H), 2.55 (dd, J=15.6, 6.7 Hz, 2H), 2.08 (d, J=7.5 Hz, 2H); $^{13}$C NMR (150 MHz, DMSO-$d_6$) δ 168.7, 143.0, 126.6, 124.8, 38.8, 38.4, 36.6; IR (cm$^{-1}$) 3279, 2936, 1623, 1470, 974, 742; HRMS (EI) m/z calcd. for $C_{11}H_{13}NO_2$ [M]$^+$: 191.0946, found: 191.0944.

[Preparation Example 19] Preparation of 2-ethylbenzyl Hydroxamic Acid

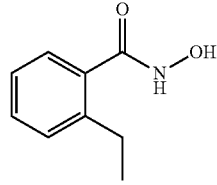

Prepared from 2-ethylbenzoic acid by Method D; White solid (0.29 g, 86%); m.p. 114-116° C.; $^1$H NMR (600 MHz, CDCl$_3$) δ 8.77 (br, 2H), 7.37 (t, J=7.5 Hz, 1H), 7.26 (t, J=8.5 Hz, 2H), 7.16 (t, J=7.5 Hz, 1H), 2.74 (q, J=7.5 Hz, 2H), 1.18 (t, J=7.5 Hz, 3H); $^{13}$C NMR (150 MHz, CDCl$_3$) δ 168.9, 143.2, 131.4, 130.9, 129.5, 127.3, 125.8, 26.1, 15.7; IR (cm$^{-1}$) 3186, 2969, 2873, 1617, 1517, 1018, 901; HRMS (EI) m/z calcd. for $C_9H_{11}NO_2$ [M]$^+$: 165.0790, found: 165.0789.

[Preparation Example 20] Preparation of 2-benzylbenzyl Hydroxamic Acid

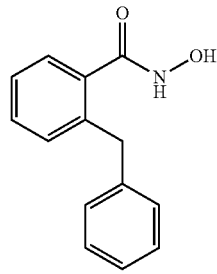 [SMILES: O=C(NO)c1ccccc1Cc1ccccc1]

Prepared from 2-benzylbenzoic acid by Method D; White solid (0.41 g, 39%); m.p. 146-148° C.; $^1$H NMR (600 MHz, DMSO-$d_6$) δ 10.90 (s, 1H), 9.06 (s, 1H), 7.31 (t, J=7.5 Hz, 1H), 7.26-7.20 (m, 6H), 7.15 (dd, J=12.7, 7.3 Hz, 2H), 4.04 (s, 2H); $^{13}$C NMR (150 MHz, DMSO-$d_6$) δ 166.1, 140.9, 139.4, 134.4, 130.1, 129.7, 128.9, 128.3, 127.5, 125.9, 125.8, 37.5; IR (cm$^{-1}$) 3243, 2864, 1613, 1450, 743, 701; HRMS (EI) m/z calcd. for $C_{14}H_{13}NO_2$ [M]: 227.0946, found: 277.0949.

[Preparation Example 21] Preparation of 4-(benzofuran-2-yl)butanyl Hydroxamic Acid

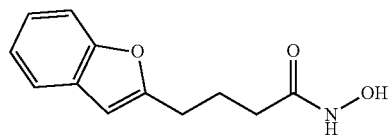 [SMILES: O=C(CCCc1cc2ccccc2o1)NO]

Prepared from methyl 4-(benzofuran-2-yl)butanoate by Method C; White solid (1.72 g, 78%); m.p. 101-103° C.; $^1$H NMR (400 MHz, CDCl$_3$) δ 8.24 (s, 2H), 7.47 (d, J=7.5 Hz, 1H), 7.40 (d, J=8.1 Hz, 1H), 7.20 (dt, J=20.9, 7.6 Hz, 2H), 6.41 (s, 1H), 2.82 (t, J=7.0 Hz, 2H), 2.22 (t, J=7.0 Hz, 2H), 2.11 (p, J=7.1 Hz, 2H); $^{13}$C NMR (150 MHz, CDCl$_3$) δ

193.2, 157.7, 154.7, 128.6, 123.4, 122.6, 120.3, 110.8, 102.8, 31.7, 27.4, 23.3; IR (cm$^{-1}$) 3163, 2999, 2890, 1624, 1452, 747, 619; HRMS (EI) m/z calcd. for C$_{12}$H$_{13}$NO$_3$ [M]$^+$: 219.0895, found: 219.0897.

[Preparation Example 22] Preparation of 4-(thiophen-2-yl)butanyl Hydroxamic Acid

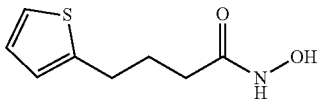 [SMILES: O=C(CCCc1cccs1)NO]

Prepared from 4-(thiophen-2-yl)butanoic acid by Method B; White solid (1.64 g, 88%); m.p. 69-71° C.; $^1$H NMR (400 MHz, CDCl$_3$) δ 8.76 (br, 2H), 7.11 (dd, J=5.1, 1.0 Hz, 1H), 6.90 (dd, J=5.1, 3.4 Hz, 1H), 6.77 (d, J=2.6 Hz, 1H), 2.84 (t, J=7.3 Hz, 2H), 2.16 (t, J=7.3 Hz, 2H), 2.00 (p, J=7.5 Hz, 2H); $^{13}$C NMR (150 MHz, CDCl$_3$) δ 171.2, 143.6, 126.8, 124.7, 123.4, 31.8, 28.9, 27.0; IR (cm$^{-1}$) 3218, 3034, 2898, 1621, 1528, 1071, 704; HRMS (EI) m/z calcd. for C$_8$H$_{11}$NO$_2$S [M]$^+$: 185.0510, found: 185.0513.

[Preparation Example 23] Preparation of 4-methylpentanyl hydroxamiclIII Acid

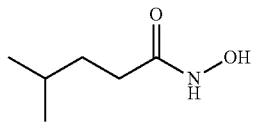

Prepared from 4-methylpentanoic acid by Method B; White solid (1.26 g, 96%); m.p. 47-49° C.; $^1$H NMR (600 MHz, CDCl$_3$) δ 9.18 (br, 2H), 2.14 (t, J=7.8 Hz, 2H), 1.61-1.47 (m, 3H), 0.88 (d, J=6.4 Hz, 6H); $^{13}$C NMR (150 MHz, CDCl$_3$) δ 172.2, 34.2, 31.0, 27.7, 22.2; IR (cm$^{-1}$) 3186, 2954, 2922, 1625, 1533, 1057, 586; HRMS (EI) m/z calcd. for C$_6$H$_{13}$NO$_2$ [M]$^+$: 131.0946, found: 131.0948.

[Preparation Example 24] Preparation of 3-cyclohexylpropanyl Hydroxamic Acid

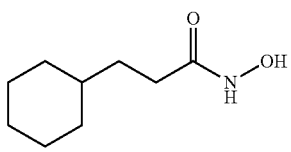 [SMILES: O=C(CCC1CCCCC1)NO]

Prepared from 3-cyclohexylpropanoic acid by Method B; White solid (1.63 g, 95%); m.p. 81-83° C.; $^1$H NMR (600 MHz, CDCl$_3$) δ 8.78 (br, 2H), 2.15 (t, J=8.3 Hz, 2H), 1.72-1.62 (m, 5H), 1.51 (q, J=7.1 Hz, 2H), 1.24-1.11 (m, 4H), 0.88 (q, J=14.4, 12.6 Hz, 2H); $^{13}$C NMR (150 MHz, CDCl$_3$) δ 172.2, 37.2, 32.9, 32.7, 30.6, 26.5, 26.2; IR (cm$^{-1}$) 3254, 2925, 2848, 1619, 1447, 736; HRMS (EI) m/z calcd. for C$_9$H$_{17}$NO$_2$ [M]$^+$: 171.1259, found: 171.1261.

[Preparation Example 25] Preparation of 2-isopropylbenzyl Hydroxamic Acid

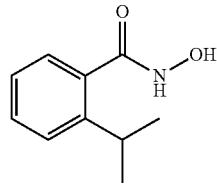

Prepared from 2-isopropylbenzoic acid by Method D; White solid (0.32 g, 88%); m.p. 89-91° C.; $^1$H NMR (600 MHz, CDCl$_3$) δ 8.60 (br, 2H), 7.43 (t, J=7.5 Hz, 1H), 7.39 (d, J=7.8 Hz, 1H), 7.27 (d, J=4.5 Hz, 1H), 7.19 (t, J=7.4 Hz, 1H), 3.27 (p, J=6.8 Hz, 1H), 1.23 (d, J=6.8 Hz, 6H); $^{13}$C NMR (150 MHz, CDCl$_3$) δ 169.0, 147.8, 131.1, 131.0, 127.2, 126.3, 125.8, 30.0, 24.1; IR (cm$^{-1}$) 3198, 2965, 1743, 1629, 1597, 1022, 761; HRMS (EI) m/z calcd. for C$_{10}$H$_{13}$NO$_2$ [M]$^+$: 179.0946, found: 179.0947.

[Preparation Example 26] Preparation of Pentanyl Hydroxamic Acid

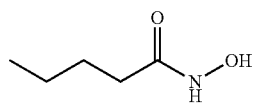

Prepared from pentanoic acid (5 mmol scale) by Method B; White solid (0.44 g, 75%); m.p. 52-54° C.; $^1$H NMR (600 MHz, CDCl$_3$) δ 8.76 (s, 2H), 2.15 (t, J=7.6 Hz, 2H), 1.61 (p, J=7.7 Hz, 2H), 1.34 (q, J=7.3 Hz, 2H), 0.90 (t, J=7.3 Hz, 3H); $^{13}$C NMR (150 MHz, CDCl$_3$) δ 171.9, 32.7, 27.4, 22.2, 13.6; IR (cm$^{-1}$) 3204, 2930, 1626, 1457, 1039; HRMS (EI) m/z calcd. for C$_5$H$_{11}$NO$_2$ [M]: 117.0790, found: 117.0788.

[Preparation Example 27] Preparation of 2-cyclopentylacetyl Hydroxamic Acid

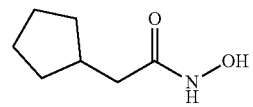

Prepared from 2-cyclopentylacetic acid (5 mmol scale) by Method B; White solid (1.33 g, 93%); m.p. 113-115° C.; $^1$H NMR (600 MHz, DMSO-d$_6$) δ 10.28 (s, 1H), 8.63 (s, 1H), 2.10 (hept, J=7.6 Hz, 1H), 1.91 (d, J=7.5 Hz, 2H), 1.69-1.63 (m, 2H), 1.53 (tq, J=10.6, 6.0, 4.3 Hz, 2H), 1.47 (ddd, J=11.6, 9.7, 7.2 Hz, 2H), 1.08 (dq, J=15.6, 7.8 Hz, 2H); $^{13}$C NMR (150 MHz, DMSO-d$_6$) δ 169.1, 38.8, 36.9, 32.3, 24.9; IR (cm$^{-1}$) 3171, 2950, 2864, 1625, 1448, 981, 534; HRMS (EI) m/z calcd. for C$_7$H$_{13}$NO$_2$ [M]$^+$: 143.0946, found: 143.0945.

[Preparation Example 28] Preparation of 2-(adamantan-1-yl)acetyl Hydroxamic Acid

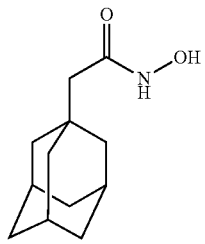 [SMILES: O=C(CC12CC3CC(CC(C3)C1)C2)NO]

Prepared from 1-adamantaneacetic acid by Method D; White solid (0.34 g, 80%); m.p. 179-181° C.; $^1$H NMR (600 MHz, DMSO-$d_6$) δ 10.21 (s, 1H), 8.60 (s, 1H), 1.89 (s, 3H), 1.67 (s, 2H), 1.63 (d, J=11.9 Hz, 3H), 1.55-1.52 (m, 9H); $^{13}$C NMR (150 MHz, DMSO-$d_6$) δ 167.2, 47.1, 42.5, 36.9, 32.6, 28.5; IR (cm$^{-1}$) 3199, 2897, 2842, 1622, 1536, 1068; HRMS (EI) m/z calcd. for $C_{12}H_{19}NO_2$ [M]$^+$: 209.1416, found: 209.1415.

[Preparation Example 29] Preparation of hex-5-enyl Hydroxamic Acid

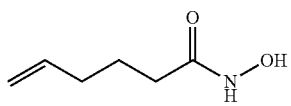

Prepared from methyl hex-5-enoate (15 mmol scale) by Method C; Yellowish oil (1.54 g, 80%); $^1$H NMR (400 MHz, CDCl$_3$) δ 9.24 (s, 2H), 5.74 (td, J=16.8, 6.7 Hz, 1H), 5.05-4.95 (m, 2H), 2.14 (t, J=7.6 Hz, 2H), 2.06 (q, J=7.2 Hz, 2H), 1.71 (p, J=7.5 Hz, 2H); $^{13}$C NMR (150 MHz, CDCl$_3$) δ 171.8, 137.4, 115.6, 32.9, 32.1, 24.5; IR (cm$^{-1}$) 3197, 2903, 1628, 911; HRMS (EI) m/z calcd. for $C_6H_{11}NO_2$ [M]$^+$: 129.0790, found: 129.0791.

[Preparation Example 30] Preparation of (E)-6-Phenylhex-5-enyl Hydroxamic Acid

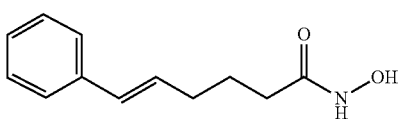 [SMILES: O=C(CCC/C=C/c1ccccc1)NO]

Prepared from methyl (E)-6-phenylhex-5-enoate (6.4 mmol scale) by Method C; White solid (0.80 g, 61%); m.p. 100-102° C.; $^1$H NMR (600 MHz, DMSO-$d_6$) δ 10.33 (s, 1H), 8.65 (s, 1H), 7.36 (d, J=7.7 Hz, 2H), 7.27 (t, J=7.5 Hz, 2H), 7.17 (t, J=7.4 Hz, 1H), 6.36 (d, J=15.9 Hz, 1H), 6.25 (dt, J=15.2, 6.8 Hz, 1H), 2.13 (q, J=7.3 Hz, 2H), 1.97 (t, J=7.5 Hz, 2H), 1.63 (p, J=7.5 Hz, 2H); $^{13}$C NMR (150 MHz, DMSO-$d_6$) δ 169.3, 137.7, 130.4, 128.9, 127.4, 126.3, 32.3, 32.2, 25.3; IR (cm$^{-1}$) 3174, 3020, 2922, 1625, 964, 689; HRMS (EI) m/z calcd. for $C_{12}H_{15}NO_2$ [M]$^+$: 205.1103, found: 205.1104.

[Preparation Example 31] Preparation of 5-phenylhex-5-enyl Hydroxamic Acid

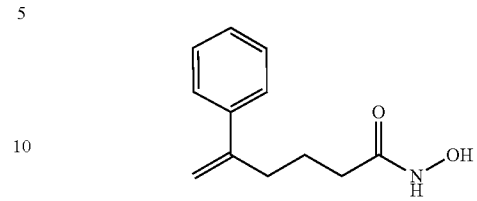

Prepared from methyl 5-phenylhex-5-enoate (3.5 mmol scale) by Method C; White solid (0.57 g, 79%); m.p. 77-79° C.; $^1$H NMR (400 MHz, CDCl$_3$, two protons can't detected due to broadness) δ 7.37 (d, J=7.6 Hz, 2H), 7.32 (t, J=6.9 Hz, 2H), 7.30-7.25 (m, 1H), 5.30 (s, 1H), 5.07 (s, 1H), 2.54 (t, J=7.2 Hz, 2H), 2.14 (t, J=6.8 Hz, 2H), 1.80 (p, J=7.3 Hz, 2H); $^{13}$C NMR (150 MHz, CDCl$_3$) δ 171.0, 147.3, 140.6, 128.4, 127.6, 126.1, 113.2, 34.4, 32.0, 23.5; IR (cm$^{-1}$) 3172, 3024, 2909, 1624, 1450, 904, 777, 707; HRMS (EI) m/z calcd. for $C_{12}H_{15}NO_2$ [M]$^+$: 205.1103, found: 205.1100.

[Preparation Example 32] Preparation of 6-phenylhex-5-ynyl Hydroxamic Acid

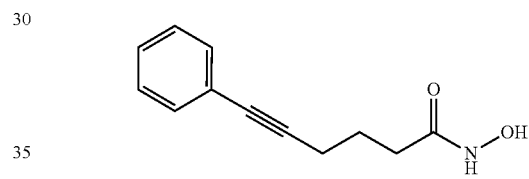

Prepared from methyl 6-phenylhex-5-ynoate by Method C; White solid (1.9 g, 93%); m.p. 66-68° C.; $^1$H NMR (400 MHz, CDCl$_3$) δ 8.66 (s, 2H), 7.39-7.34 (m, 2H), 7.28-7.23 (m, 3H), 2.45 (t, J=6.8 Hz, 2H), 2.32 (t, J=7.4 Hz, 2H), 1.92 (p, J=7.2 Hz, 2H); $^{13}$C NMR (150 MHz, CDCl$_3$) δ 171.1, 131.5, 128.2, 127.8, 123.5, 88.4, 81.8, 31.6, 24.2, 18.7; IR (cm$^{-1}$) 3269, 3200, 2903, 1624, 1438, 1035, 752, 689; HRMS (EI) m/z calcd. for $C_{12}H_{13}NO_2$ [M]$^+$: 203.0946, found: 203.0945.

[Preparation Example 33] Preparation of 7-phenylhept-5-ynyl Hydroxamic Acid

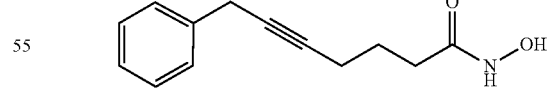

Prepared from methyl 7-phenylhept-5-ynoic acid (2 mmol scale) by Method B; Yellow resin (0.33 g, 75%); $^1$H NMR (600 MHz, acetone-$d_6$) δ 10.36 (s, 1H), 9.29 (s, 1H), 7.35-7.33 (m, 2H), 7.29 (t, J=7.6 Hz, 2H), 7.20 (t, J=7.3 Hz, 1H), 3.56 (s, 2H), 2.32-2.22 (m, 4H), 1.82 (p, J=7.3 Hz, 2H); $^{13}$C NMR (150 MHz, acetone-$d_6$) δ 170.5, 137.6, 128.4, 127.8, 126.3, 81.4, 78.4, 31.5, 25.0, 24.5, 18.0; IR (cm$^{-1}$) 3196, 2934, 1638, 1451, 1264, 766, 694; HRMS (ESI) m/z calcd. for $C_{13}H_{15}NO_2$ [M+H]$^+$: 218.1176, found: 218.1157.

[Preparation Example 34] Preparation of hept-5-ynyl Hydroxamic Acid

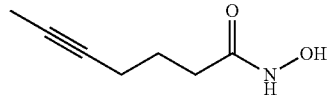

Prepared from hept-5-ynoic acid by Method B; White solid (1.45 g, 62%); m.p. 74-76° C.; $^1$H NMR (600 MHz, acetone-$d_6$) δ 10.07 (s, 1H), 8.78 (s, 1H), 2.19 (t, J=7.3 Hz, 2H), 2.14-2.10 (m, 2H), 1.76-1.66 (m, 5H); $^{13}$C NMR (150 MHz, acetone-$d_6$) δ 169.8, 77.9, 75.7, 31.2, 24.9, 17.8, 2.3; IR (cm$^{-1}$) 3255, 3060, 2740, 1657, 1433, 1021, 444; HRMS (EI) m/z calcd. for $C_7H_{11}NO_2$ [M]$^+$: 141.0790, found: 141.0790.

[Preparation Example 35] Preparation of 3-benzylpentanyl Hydroxamic Acid

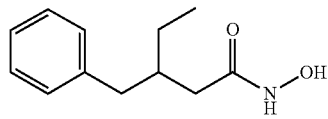

Prepared from 3-benzylpentanoic acid (1.5 mmol scale) by Method D; White solid (0.28 g, 89%); m.p. 90-92° C.; $^1$H NMR (400 MHz, CDCl$_3$, two protons can't detected due to broadness) δ 7.29 (t, J=7.3 Hz, 2H), 7.20 (t, J=7.3 Hz, 1H), 7.15 (d, J=7.5 Hz, 2H), 2.68 (dd J=13.6, 6.6 Hz, 1H), 2.51 (dd, J=13.6, 7.3 Hz, 1H), 2.25-2.09 (m, 1H), 2.04 (d, J=6.7 Hz, 2H), 1.37 (p, J=7.4 Hz, 2H), 0.92 (t, J=7.3 Hz, 3H); $^{13}$C NMR (150 MHz, CDCl$_3$) δ 171.2, 140.0, 129.2, 128.3, 126.1, 39.6, 38.5, 36.6, 25.9, 10.9; IR (cm$^{-1}$) 3223, 2961, 2928, 1636, 1494, 1453, 699; HRMS (FAB) m/z calcd. for $C_{12}H_{17}NO_2$ [M+H]$^+$ 208.1338, found: 208.1338.

[Preparation Example 36] Preparation of 3-benzyl-4-methylpentanyl Hydroxamic Acid

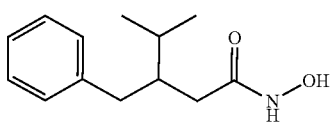 [SMILES: CC(C)C(CC(=O)NO)Cc1ccccc1]

Prepared from 3-benzyl-4-methylpentanoic acid (1.8 mmol scale) by Method D; Yellow solid (0.34 g, 82%); m.p. 80-82° C.; $^1$H NMR (400 MHz, CD$_2$Cl$_2$) 8.97 (s, 2H), 7.29 (t, J=7.2 Hz, 2H), 7.24-7.14 (m, 3H), 2.64 (dd, J=13.1, 6.0 Hz, 1H), 2.45 (dd, J=12.4, 6.8 Hz, 1H), 2.19-2.02 (m, 2H), 1.98-1.86 (m, 1H), 1.78-1.65 (m, 1H), 0.89 (dd, J=14.3, 6.5 Hz, 6H); $^{13}$C NMR (100 MHz, CD$_2$Cl$_2$) δ 172.0, 141.1, 129.4, 128.5, 126.1, 43.1, 36.8, 33.7, 28.6, 18.9, 18.3; IR (cm$^{-1}$) 3205, 2956, 1635, 698; HRMS (FAB) m/z calcd. for $C_{13}H_{19}NO_2$ [M+H]$^+$: 222.1494, found: 222.1496.

[Preparation Example 37] Preparation of (S)-2-(1,3-dioxoisoindolin-2-yl)-4-methylpentanylHydroxamic Acid

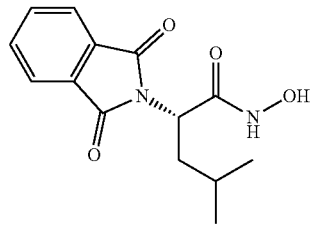 [SMILES: CC(C)C[C@@H](C(=O)NO)N1C(=O)c2ccccc2C1=O]

Prepared from (S)-2-(1,3-dioxoisoindolin-2-yl)-4-methylpentanoic acid by Method D; White solid (0.45 g, 81%); m.p. 155-157° C.; $^1$H NMR (600 MHz, CDCl$_3$, one proton can't detected due to broadness) δ 9.33 (s, 1H), 7.87 (dd, J=5.5, 3.1 Hz, 2H), 7.76 (dd, J=5.5, 3.0 Hz, 2H), 5.01 (dd, J=11.2, 5.2 Hz, 1H), 2.34-2.20 (m, 1H), 1.83 (ddd, J=14.2, 9.4, 5.3 Hz, 1H), 1.46 (q, J=7.8, 7.0 Hz, 1H), 0.93 (dd, J=6.7, 2.3 Hz, 6H); $^{13}$C NMR (150 MHz, CDCl$_3$) δ 168.1, 167.8, 134.5, 131.4, 123.7, 51.4, 37.5, 25.0, 22.9, 21.3; IR (cm$^{-1}$) 3228, 2957, 1715, 1644, 1380, 717; HRMS (EI) m/z calcd. for $C_{14}H_{16}N_2O_4$ [M]$^+$: 276.1110, found: 276.1111.

[Preparation Example 38] Preparation of (S)-2-(1,3-dioxoisoindolin-2-yl)-4-phenylbutanylhydroxamic Acid

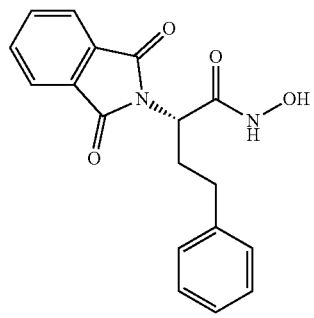 [SMILES: O=C(NO)[C@H](CCc1ccccc1)N1C(=O)c2ccccc2C1=O]

Prepared from (S)-2-(1,3-dioxoisoindolin-2-yl)-4-phenylbutanoic acid (3.0 mmol scale) by Method D; White solid (0.49 g, 76%); m.p. 114-116° C.; $^1$H NMR (600 MHz, DMSO-$d_6$) δ 10.80 (s, 1H), 8.87 (s, 1H), 7.88-7.83 (m, 4H), 7.18 (t, J=7.5 Hz, 2H), 7.11 (d, J=7.5 Hz, 2H), 7.07 (t, J=7.4 Hz, 1H), 4.62 (dd, J=10.4, 4.8 Hz, 1H), 2.58-2.51 (m, 2H), 2.48-2.41 (m, 2H); $^{13}$C NMR (150 MHz, DMSO-$d_6$) δ 167.7, 165.2, 140.6, 134.4, 131.7, 128.3, 128.3, 125.8, 123.1, 51.4, 32.1, 29.3; IR (cm$^{-1}$) 3303, 3165, 2954, 1695, 1653, 1386, 712; HRMS (EI) m/z calcd. for $C_{18}H_{16}N_2O_4$ [M]$^+$: 324.1110, found: 324.1112.

[Preparation Example 39] Preparation of (R)-3-(1,3-dioxoisoindolin-2-yl)-4-methylpentanyl Hydroxamic Acid

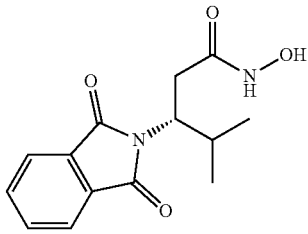 [SMILES: CC(C)[C@@H](CC(=O)NO)N1C(=O)c2ccccc2C1=O]

Prepared from (R)-3-(1,3-dioxoisoindolin-2-yl)-4-methylpentanoic acid (2.0 mmol scale) by Method B; White solid (0.39 g, 71%); m.p. 154-156° C.; $^1$H NMR (400 MHz, DMSO-d$_6$) δ 10.44 (s, 1H), 8.66 (s, 1H), 7.86-7.79 (m, 4H), 4.17 (td, J=9.8, 4.8 Hz, 1H), 2.75 (dd, J=14.7, 10.2 Hz, 1H), 2.56 (dd, J=14.7, 4.7 Hz, 1H), 2.24-2.09 (m, 1H), 0.97 (d, J=6.7 Hz, 3H), 0.77 (d, J=6.7 Hz, 3H); $^{13}$C NMR (100 MHz, DMSO-d$_6$) δ 168.4, 167.2, 134.9, 131.6, 123.5, 54.5, 33.2, 31.0, 20.4, 20.0; IR (cm$^{-1}$) 3255, 2963, 2872, 1695, 1359, 719; HRMS (EI) m/z calcd. for C$_{14}$H$_{16}$N$_2$O$_4$ [M]$^+$: 276.1110, found: 276.1113.

[Preparation Example 40] Preparation of 2-(1-((1,3-dioxoisoindolin-2-yl)methyl)cyclohexyl)acetylhydroxamic Acid

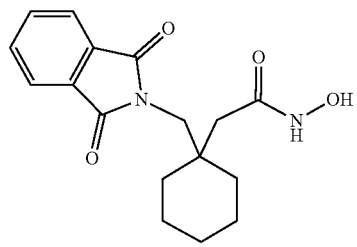 [SMILES: O=C(CC1(CN2C(=O)c3ccccc3C2=O)CCCCC1)NO]

Prepared from 2-(1-((1,3-dioxoisoindolin-2-yl)methyl)cyclohexyl)acetic acid (2.0 mmol scale) by Method D: White solid (0.43 g, 68%); m.p. 152-154° C.; $^1$H NMR (400 MHz, DMSO-d$_6$) δ 10.40 (s, 1H), 8.77 (s, 1H), 7.85 (m, 4H), 3.65 (s, 2H), 2.06 (s, 2H), 1.61-1.06 (m, 10H); $^{13}$C NMR (100 MHz, DMSO-d$_6$) δ 169.5, 167.8, 135.0, 132.4, 123.7, 46.8, 38.9, 38.8, 33.2, 25.9, 21.8; IR (cm$^{-1}$) 3274, 3140, 2922, 2868, 1697, 1396, 713; HRMS (EI) m/z calcd. for C$_{17}$H$_{20}$N$_2$O$_4$[M]$^+$: 316.1423, found: 316.1422.

[Preparation Example 41] Preparation of tert-butyl ([1-{2-(hydroxyamino)-2-oxoethyl}cyclohexyl]methyl)carbamate

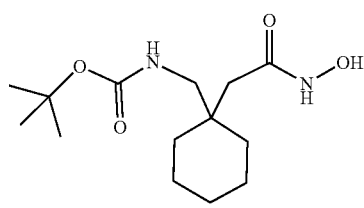 [SMILES: CC(C)(C)OC(=O)NCC1(CC(=O)NO)CCCCC1]

Prepared from 2-(1-[{(tert-butoxycarbonyl)amino}methyl]cyclohexyl)acetic acid (2.0 mmol scale) by Method B; White solid (0.39 g, 68%); m.p. 129-131° C.; $^1$H NMR (400 MHz, DMSO-d$_6$) δ 10.40 (s, 1H), 8.75 (s, 1H), 6.65 (s, 1H), 2.94 (d, J=6.3 Hz, 2H), 1.88 (s, 2H), 1.40-1.14 (m, 19H); $^{13}$C NMR (100 MHz, DMSO-d$_6$) δ 167.8, 156.5, 78.0, 47.3, 40.5, 37.2, 33.3, 28.7, 26.1, 21.5; IR (cm$^{-1}$) 3244, 2926, 1683, 1651, 1508, 1453, 1365, 1250, 1166; HRMS (FAB) m/z calcd. for C$_{14}$H$_{26}$N$_2$O$_4$ [M+H]$^+$: 287.1971, found: 287.1968.

[Preparation Example 42] Preparation of anti-(Z)-2-(3-oxo-2-(pent-2-en-1-yl)cyclopentyl)acetyl Hydroxamic Acid

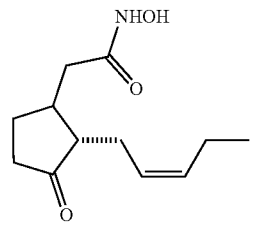

Prepared from Jasmonic acid by Method D; White solid (0.35 g, 78%); m.p. 91-93° C.; $^1$H NMR (400 MHz, DMSO-d$_6$) δ 10.40 (s, 1H), 8.72 (s, 1H), 5.34 (q, J=7.8 Hz, 1H), 5.23-5.14 (m, 1H), 2.27-2.11 (m, 5H), 2.04-1.86 (m, 6H), 1.43-1.30 (m, 1H), 0.87 (t, J=7.5 Hz, 3H); $^{13}$C NMR (150 MHz, DMSO-d$_6$) δ 219.2, 168.1, 133.3, 126.1, 53.8, 38.0, 37.7, 37.4, 26.9, 25.3, 20.5, 14.5; IR (cm$^{-1}$) 3206, 2931, 1733, 1647, 733, 701; HRMS (EI) m/z calcd. for C$_{12}$H$_{19}$NO$_3$ [M]$^+$: 225.1365, found: 225.1366.

[Preparation Example 43] Preparation of (4R)-4-((3R,8R,9S,10S,13R,14S,17R)-3-methoxy-10,13-dimethylhexadecahydro-1H-cyclopenta[a]phenanthren-17-yl)pentanoyl Hydroxamic Acid

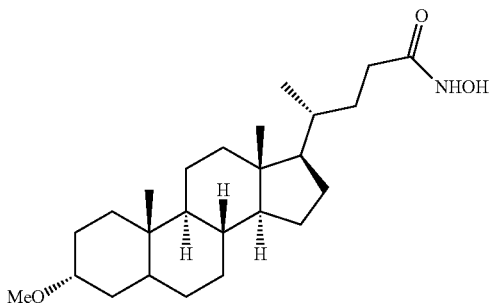

Prepared from 3α-methyl lithocholic acid (5.0 mmol scale) by Method B; White solid (1.38 g, 68%); m.p. 160-162° C.; $^1$H NMR (600 MHz, DMSO-d$_6$) δ 10.31 (s, 1H), 8.63 (s, 1H), 3.21 (s, 3H), 3.10 (tt, J=10.2, 4.3 Hz, 1H), 1.99-1.90 (m, 2H), 1.83 (dq, J=31.7, 12.8, 10.5 Hz, 3H), 1.76-1.62 (m, 3H), 1.55 (dd, J=23.8, 11.6 Hz, 3H), 1.33 (t, J=10.3 Hz, 6H), 1.23-1.11 (m, 5H), 1.10-0.99 (m, 5H), 0.92-0.86 (m, 7H), 0.61 (s, 3H); $^{13}$C NMR (150 MHz, DMSO-d$_6$, one carbon merged to solvent peak) δ 169.9, 79.9, 56.4, 56.0, 55.2, 42.7, 41.8, 40.1, 35.8, 35.3, 35.3, 34.9,

[Preparation Example 44] Preparation of 3,7-dimethyloct-6-enoylHydroxamic Acid

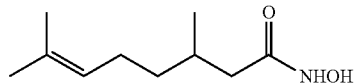

Prepared from citronellic acid (5.0 mmol scale) by Method B; White solid (0.62 g, 67%); m.p. 49-51° C.; $^1$H NMR (600 MHz, CDCl$_3$) δ 9.13 (br, 1H), 8.63 (s, 1H), 5.05 (t, J=7.3 Hz, 1H), 2.15 (dd, J=13.6, 5.4 Hz, 1H), 2.03-1.91 (m, 3H), 1.88 (dd, J=13.6, 8.6 Hz, 1H), 1.66 (s, 3H), 1.57 (s, 3H), 1.34 (td, J=14.9, 14.3, 6.0 Hz, 1H), 1.19 (dt, J=13.3, 6.7 Hz, 1H), 0.91 (d, J=6.5 Hz, 3H); $^{13}$C NMR (150 MHz, CDCl$_3$) δ 171.2, 131.7, 124.1, 40.5, 36.7, 30.2, 25.7, 25.4, 19.3, 17.6; IR (cm$^{-1}$) 3191, 2963, 2913, 1632, 1451, 735; HRMS (EI) m/z calcd. for C$_{10}$H$_{19}$NO$_2$ [M]$^+$: 185.1416, found: 185.1417.

[Preparation Example 45] Preparation of (S)-2-((2R,4aS)-4a,8-dimethyl-7-oxo-1,2,3,4,4a,7-hexahydronaphthalen-2-yl)propanoyl Hydroxamic Acid

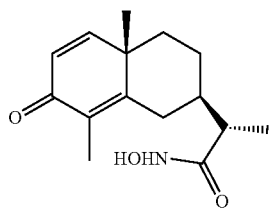

Prepared from (S)-2-((2R,4aS)-4a,8-dimethyl-7-oxo-1,2,3,4,4a,7-hexahydronaphthalen-2-yl)propanoic acid (1.0 mmol scale) by Method B; White solid (0.15 g, 58%); m.p. 119-121° C.; $^1$H NMR (400 MHz, acetone-d$_6$, two protons can't detected due to broadness) δ 6.83 (d, J=9.8 Hz, 1H), 6.07 (d, J=9.8 Hz, 1H), 2.84-2.74 (m, 1H), 2.26-2.14 (m, 1H), 1.94-1.85 (m, 1H), 1.83-1.71 (m, 4H), 1.60-1.41 (m, 2H), 1.32-1.19 (m, 1H), 1.19 (s, 3H), 1.14-1.09 (m, 4H); $^{13}$C NMR (100 MHz, acetone-d$_6$) δ 185.2, 172.6, 159.4, 156.6, 128.7, 125.9, 43.0, 42.6, 40.3, 37.9, 31.8, 24.7, 22.9, 15.0, 9.8; IR (cm$^{-1}$) 3186, 2921, 1650, 1596, 1451, 949, 834; HRMS (EI) m/z calcd. for C$_{15}$H$_{21}$NO$_3$ [M]$^+$: 263.1521, found: 263.1519.

Preparation Example IV: Preparation of 3-substituted-1,4,2-dioxazol-5-one Compound A hydroxamic acid compound (5.0 mmol) was dissolved in dichloromethane (50 mL), 1,1'-carbonyldiimidazole (0.81 g, 5.0 mmol) was added thereto all together at room temperature, and the mixture was stirred for 30 minutes. After the reaction was completed, the product was quenched with 1 N HCl (30 mL), extracted with dichloromethane (50 mL×3), and dried with magnesium sulfate, and the solvent was removed under reduced pressure. The residue was filtered with silica and washed with dichloromethane (10 mL×2), and then the filtrate was distilled under reduced pressure to obtain the title compound.

The following compound was prepared in the same manner as in the above, except that the starting material was different.

[Preparation Example 46] Preparation of 3-(3-phenylpropyl)-1,4,2-dioxazol-5-one

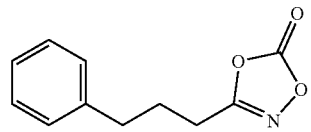 [SMILES: O=c1onc(CCCc2ccccc2)o1]

Colorless liquid (0.82 g, 80%); $^1$H NMR (600 MHz, CDCl$_3$) δ 7.32 (t, J=7.5 Hz, 2H), 7.23 (t, J=7.3 Hz, 1H), 7.18 (d, J=7.5 Hz, 2H), 2.75 (t, J=7.4 Hz, 2H), 2.62 (t, J=7.5 Hz, 2H), 2.07 (p, J=7.4 Hz, 2H); $^{13}$C NMR (150 MHz, CDCl$_3$) δ 166.4, 154.0, 139.7, 128.6, 128.4, 126.5, 34.5, 25.9, 24.0; IR (cm$^{-1}$) 3207, 2913, 1827, 1634, 1452, 980; HRMS (EI) m/z calcd. for C$_{11}$H$_{11}$NO$_3$ [M]$^+$: 205.0739, found: 205.0737.

[Preparation Example 47] Preparation of 3-(3-(4-bromophenyl)propyl)-1,4,2-dioxazol-5-one

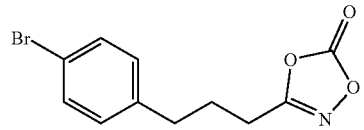

White solid (1.3 g, 93%); $^1$H NMR (400 MHz, CDCl$_3$) δ 7.44 (d, J=8.2 Hz, 2H), 7.06 (d, J=8.2 Hz, 2H), 2.70 (t, J=7.5 Hz, 2H), 2.62 (t, J=7.4 Hz, 2H), 2.04 (p, J=7.4 Hz, 2H); $^{13}$C NMR (150 MHz, CDCl$_3$) δ 166.2, 154.0, 138.7, 131.8, 130.1, 120.4, 33.9, 25.7, 23.9; IR (cm$^{-1}$) 2925, 1867, 1826, 1631, 1152, 985; HRMS (EI) m/z calcd. for C$_{11}$H$_{10}$BrNO$_3$ [M]$^+$: 282.9844, found: 282.9843.

[Preparation Example 48] Preparation of 3-(3-(4-fluorophenyl)propyl)-1,4,2-dioxazol-5-one

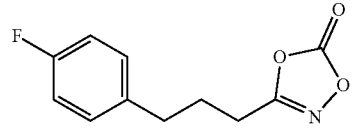 [SMILES: O=c1onc(CCCc2ccc(F)cc2)o1]

Colorless liquid (0.41 g, 90%); $^1$H NMR (600 MHz, CD$_2$Cl$_2$) δ 7.22-7.12 (m, 2H), 7.07-6.95 (m, 2H), 2.72 (t, J=7.5 Hz, 2H), 2.63 (t, J=7.5 Hz, 2H), 2.03 (p, J=7.5 Hz, 2H); $^{13}$C NMR (150 MHz, CD$_2$Cl$_2$) δ 166.6, 161.5 (d, J=243.4 Hz), 154.1, 135.9 (d, J=3.1 Hz), 129.9 (d, J=7.8 Hz), 115.2 (d, J=21.3 Hz), 33.7, 26.0, 24.0; $^{19}$F NMR (564 MHz, CD$_2$Cl$_2$) δ-117.7 (m); IR (cm$^{-1}$) 2934, 1870, 1825, 1508, 1218, 1150, 981; HRMS (EI) m/z calcd. for C$_{11}$H$_{10}$FNO$_3$ [M]$^+$: 223.0645, found: 223.0646.

[Preparation Example 49] Preparation of 3-(3-(4-nitrophenyl)propyl)-1,4,2-dioxazol-5-one

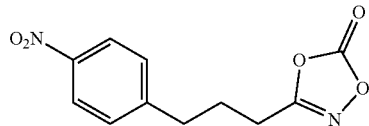 [SMILES: O=c1onc(CCCc2ccc([N+](=O)[O-])cc2)o1]

White solid (1.0 g, 81%); $^1$H NMR (600 MHz, CDCl$_3$) δ 8.18 (d, J=8.6 Hz, 2H), 7.36 (d, J=8.6 Hz, 2H), 2.86 (t, J=7.7 Hz, 2H), 2.67 (t, J=7.4 Hz, 2H), 2.12 (p, J=7.5 Hz, 2H); $^{13}$C NMR (150 MHz, CDCl$_3$) 165.9, 153.8, 147.5, 146.9, 129.2, 124.0, 34.4, 25.4, 24.1; IR (cm$^{-1}$) 1828, 1536, 1346, 1152, 990, 948; HRMS (EI) m/z calcd. for C$_{11}$H$_{10}$N$_2$O$_5$[M]$^+$: 250.0590, found: 250.0592.

[Preparation Example 50] Preparation of 3-(3-(4-methoxyphenyl)propyl)-1,4,2-dioxazol-5-one

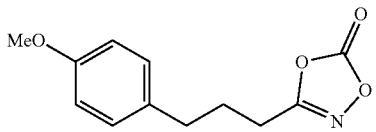 [SMILES: COc1ccc(CCCc2noc(=O)o2)cc1]

Yellowish oil (1.1 g, 95%); $^1$H NMR (600 MHz, CDCl$_3$) δ 7.09 (d, J=8.3 Hz, 2H), 6.85 (d, J=8.3 Hz, 2H), 3.80 (s, 3H), 2.69 (t, J=7.4 Hz, 2H), 2.60 (t, J=7.4 Hz, 2H), 2.03 (p, J=7.4 Hz, 2H); $^{13}$C NMR (150 MHz, CDCl$_3$) δ 166.5, 158.3, 154.1, 131.7, 129.4, 114.1, 55.3, 33.6, 26.1, 23.9; IR (cm$^{-1}$) 2936, 1870, 1825, 1510, 1242, 981; HRMS (EI) m/z calcd. for C$_{12}$H$_{13}$NO$_4$ [M]$^+$: 235.0845, found: 235.0846.

[Preparation Example 51] Preparation of tert-butyl [4-{3-(5-oxo-1,4,2-dioxazol-3-yl)propyl}phenyl]carbamate

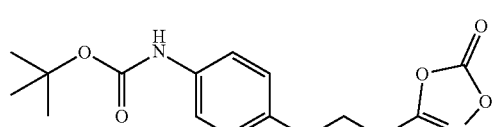

Prepared on a 1.2 mmol scale. Due to the stability of a Boc group, the desired compound was obtained through a silica filter directly using dichloromethane without quenching with 1 N HCl after the reaction. White solid (0.30 g, 78%); $^1$H NMR (600 MHz, CDCl$_3$) δ 7.28 (d, J=7.9 Hz, 2H), 7.07 (d, J=8.5 Hz, 2H), 6.43 (s, 1H), 2.66 (t, J=7.3 Hz, 2H), 2.58 (t, J=7.5 Hz, 2H), 2.00 (p, J=7.5 Hz, 2H), 1.49 (s, 9H); $^{13}$C NMR (150 MHz, CDCl$_3$) δ 166.4, 154.1, 152.8, 136.8, 134.4, 128.9, 118.9, 80.5, 33.8, 28.3, 25.9, 23.9; IR (cm$^{-1}$) 3334, 2978, 1870, 1825, 1703, 1520, 1151; HRMS (FAB) m/z calcd. for C$_{16}$H$_{20}$N$_2$O$_5$[M+H]$^+$: 321.1450, found: 321.1448.

[Preparation Example 52] Preparation of 3-(2-Methyl-4-phenylbutan-2-yl)-1,4,2-dioxazol-5-one

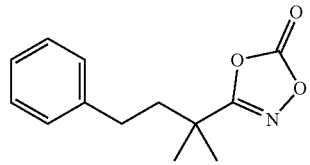 [SMILES: CC(C)(CCc1ccccc1)c1noc(=O)o1]

Colorless liquid (0.92 g, 79%); $^1$H NMR (600 MHz, CDCl$_3$) δ 7.29 (t, J=7.5 Hz, 2H), 7.21 (t, J=7.4 Hz, 1H), 7.16 (d, J=7.6 Hz, 2H), 2.64-2.59 (m, 2H), 1.98-1.93 (m, 2H), 1.40 (s, 6H); $^{13}$C NMR (150 MHz, CDCl$_3$) δ 171.3, 154.3, 140.4, 128.5, 128.3, 126.3, 41.2, 35.9, 30.8, 24.2; IR (cm$^{-1}$) 2978, 1869, 1824, 1110, 974; HRMS (EI) m/z calcd. for C$_{13}$H$_{15}$NO$_3$ [M]$^+$: 233.1052, found: 233.1051.

[Preparation Example 53] Preparation of 3-(4-phenylbutan-2-yl)-1,4,2-dioxazol-5-one

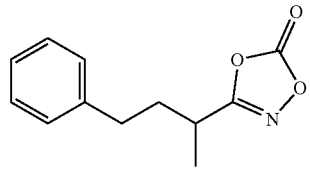 [SMILES: CC(CCc1ccccc1)c1noc(=O)o1]

Colorless liquid (0.42 g, 95%); $^1$H NMR (600 MHz, CD$_2$Cl$_2$) δ 7.30 (t, J=7.4 Hz, 2H), 7.24-7.16 (m, 3H), 2.91-2.81 (m, 1H), 2.76-2.64 (m, 2H), 2.14-2.03 (m, 1H), 1.97-1.86 (m, 1H), 1.35 (d, J=7.0 Hz, 3H); $^{13}$C NMR (150 MHz, CD$_2$Cl$_2$) δ 169.6, 154.2, 140.4, 128.5, 128.3, 126.2, 34.0, 32.6, 30.6, 16.0; IR (cm$^{-1}$) 3332, 1870, 1826, 1264, 976, 734; HRMS (EI) m/z calcd. for C$_{12}$H$_{13}$NO$_3$ [M]$^+$: 219.0895, found: 219.0893.

[Preparation Example 54] Preparation of 3-(2-methyl-3-phenylpropyl)-1,4,2-dioxazol-5-one

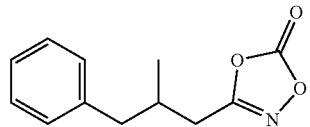 [SMILES: CC(Cc1ccccc1)Cc1noc(=O)o1]

Prepared on a 3.0 mmol scale. Yellowish oil (0.61 g, 95%); $^1$H NMR (600 MHz, CDCl$_3$) δ 7.31 (t, J=7.3 Hz, 2H), 7.24 (t, J=7.3 Hz, 1H), 7.16 (d, J=7.2 Hz, 2H), 2.70-2.59 (m, 3H), 2.44 (dd, J=15.4, 8.0 Hz, 1H), 2.30 (dq, J=14.0, 6.9 Hz, 1H), 1.05 (d, J=6.6 Hz, 3H); $^{13}$C NMR (150 MHz, CDCl$_3$) δ 165.9, 154.0, 138.8, 129.1, 128.6, 126.6, 42.7, 32.1, 31.0, 19.6; IR (cm$^{-1}$) 2929, 1875, 1826, 1631, 1145, 980; HRMS (EI) m/z calcd. for C$_{12}$H$_{13}$NO$_3$ [M]$^+$: 219.0895, found: 219.0894.

[Preparation Example 55] Preparation of 3-((2,3-dihydro-1H-inden-2-yl)methyl)-1,4,2-dioxazol-5-one

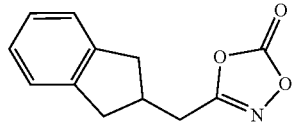 [SMILES: O=c1onc(CC2Cc3ccccc3C2)o1]

Colorless oil (0.43 g, 40%); $^1$H NMR (600 MHz, CDCl$_3$) δ 7.24-7.19 (m, 2H), 7.19-7.14 (m, 2H), 3.21 (dd, J=15.6, 7.8 Hz, 2H), 2.91 (hept, J=7.8, 7.2 Hz, 1H), 2.78 (d, J=7.4 Hz, 2H), 2.75 (dd, J=15.6, 6.4 Hz, 2H); $^{13}$C NMR (150 MHz, CDCl$_3$) δ 165.9, 154.0, 141.3, 126.8, 124.6, 38.7, 35.5, 30.3; IR (cm$^{-1}$) 1878, 1820, 1353, 1143, 990, 744; HRMS (EI) m/z calcd. for C$_{12}$H$_{11}$NO$_3$ [M]$^+$: 217.0739, found: 217.0740.

[Preparation Example 56] Preparation of 3-(2-ethylphenyl)-1,4,2-dioxazol-5-one

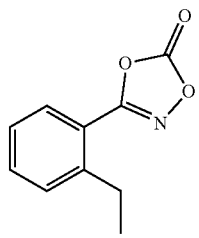

Prepared at 3.0 mmol scale. Colorless oil (0.28 g, 48%); $^1$H NMR (600 MHz, CDCl$_3$) δ 7.75 (d, J=7.8 Hz, 1H), 7.56 (t, J=7.7 Hz, 1H), 7.41 (d, J=7.8 Hz, 1H), 7.37 (t, J=7.7 Hz, 1H), 2.97 (q, J=7.5 Hz, 2H), 1.27 (t, J=7.5 Hz, 3H); $^{13}$C NMR (150 MHz, CDCl$_3$) δ 163.9, 153.7, 145.3, 133.4, 130.4, 129.1, 126.5, 118.6, 27.6, 14.9; IR (cm$^{-1}$) 1857, 1827, 1608, 1339, 1055, 969, 753; HRMS (EI) m/z calcd. for C$_{10}$H$_9$NO$_3$ [M]$^+$: 191.0582, found: 191.0581.

[Preparation Example 57] Preparation of 3-(2-benzylphenyl)-1,4,2-dioxazol-5-one

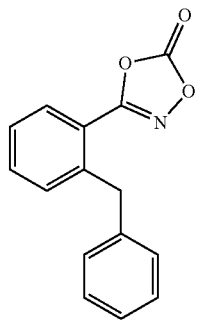 [SMILES: O=c1onc(-c2ccccc2Cc2ccccc2)o1]

White solid (0.77 g, 61%); $^1$H NMR (600 MHz, CDCl$_3$) δ 7.79 (d, J=7.9 Hz, 1H), 7.55 (t, J=7.6 Hz, 1H), 7.41 (t, J=7.6 Hz, 1H), 7.32-7.28 (m, 3H), 7.23 (t, J=7.4 Hz, 1H), 7.13 (d, J=7.6 Hz, 2H), 4.34 (s, 2H); $^{13}$C NMR (150 MHz, CDCl$_3$) δ 163.7, 153.5, 141.7, 138.8, 133.3, 131.9, 129.3, 129.0, 128.6, 127.0, 126.5, 119.3, 39.9; IR (cm$^{-1}$) 1861, 1829, 1348, 1173, 1042, 978; HRMS (EI) m/z calcd. for C$_{15}$H$_{11}$NO$_3$ [M]$^+$: 253.0739, found: 253.0739.

[Preparation Example 58] Preparation of 3-(3-(benzofuran-2-yl)propyl)-1,4,2-dioxazol-5-one

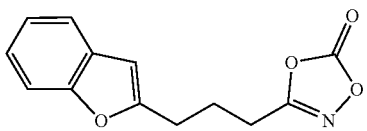 [SMILES: O=c1onc(CCCc2cc3ccccc3o2)o1]

Colorless oil (1.21 g, 99%); $^1$H NMR (400 MHz, CDCl$_3$) δ 7.54-7.49 (m, 1H), 7.43 (d, J=8.2 Hz, 1H), 7.28-7.18 (m, 2H), 6.47 (s, 1H), 2.93 (t, J=7.1 Hz, 2H), 2.72 (t, J=7.5 Hz, 2H), 2.20 (p, J=7.3 Hz, 2H); $^{13}$C NMR (150 MHz, CDCl$_3$) δ 166.1, 156.3, 154.8, 154.0, 128.5, 123.7, 122.7, 120.5, 110.9, 103.4, 27.2, 24.0, 22.6; IR (cm$^{-1}$) 1880, 1860, 1830, 1151, 981, 751; HRMS (EI) m/z calcd. for C$_{13}$H$_{11}$NO$_4$ [M]$^+$: 245.0688, found: 245.0690.

[Preparation Example 59] Preparation of 3-(3-(thiophen-2-yl)propyl)-1,4,2-dioxazol-5-one

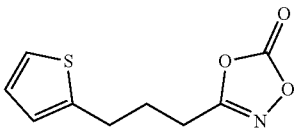 [SMILES: O=c1onc(CCCc2cccs2)o1]

Colorless liquid (0.99 g, 94%); $^1$H NMR (600 MHz, CDCl$_3$) δ 7.17 (dd, J=5.1, 1.2 Hz, 1H), 6.94 (dd, J=5.2, 3.4 Hz, 1H), 6.85-6.81 (m, 1H), 2.98 (t, J=7.2 Hz, 2H), 2.67 (t, J=7.5 Hz, 2H), 2.11 (p, J=7.3 Hz, 2H); $^{13}$C NMR (150 MHz, CDCl$_3$) δ 166.2, 154.0, 142.2, 127.0, 125.2, 123.9, 28.6, 26.2, 23.8; IR (cm$^{-1}$) 1868, 1823, 1635, 1148, 980, 695; HRMS (EI) m/z calcd. for C$_9$H$_9$NO$_3$S [M]$^+$: 211.0303, found: 211.0301.

[Preparation Example 60] Preparation of 3-isopentyl-1,4,2-dioxazol-5-one

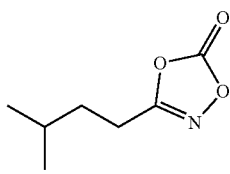

Colorless oil (0.67 g, 85%); $^1$H NMR (600 MHz, CDCl$_3$) δ 2.61 (t, J=7.6 Hz, 2H), 1.68-1.57 (m, 3H), 0.94 (d, J=6.4 Hz, 6H); $^{13}$C NMR (150 MHz, CDCl$_3$) δ 166.9, 154.2, 33.1, 27.4, 22.8, 21.9; IR (cm$^{-1}$) 2960, 1865, 1825, 1147, 981, 761; HRMS (EI) m/z calcd. for C$_7$H$_{11}$NO$_3$ [M]$^+$: 157.0739, found: 157.0738.

[Preparation Example 61] Preparation of 3-(2-cyclohexylethyl)-1,4,2-dioxazol-5-one

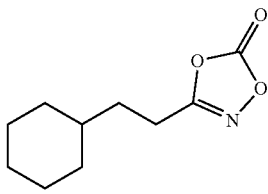 [SMILES: O=c1onc(CCC2CCCCC2)o1]

Colorless oil (0.95 g, 96%); $^1$H NMR (600 MHz, CDCl$_3$) δ 2.63 (t, J=8.0 Hz, 2H), 1.73 (d, J=10.9 Hz, 4H), 1.67 (d, J=12.6 Hz, 1H), 1.61 (q, J=7.3 Hz, 2H), 1.35-1.12 (m, 4H), 0.93 (q, J=12.0 Hz, 2H); $^{13}$C NMR (150 MHz, CDCl$_3$) δ 167.0, 154.2, 36.8, 32.7, 31.7, 26.3, 26.0, 22.3; IR (cm$^{-1}$) 2922, 2851, 1867, 1825, 1145, 974, 762; HRMS (EI) m/z calcd. for C$_{10}$H$_{15}$NO$_3$ [M]$^+$: 197.1052, found: 197.1050.

[Preparation Example 62] Preparation of 3-(2-isopropylphenyl)-1,4,2-dioxazol-5-one

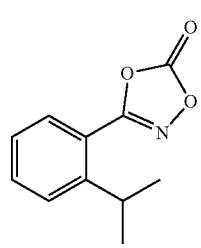

Prepared on a 0.84 mmol scale; Colorless oil (0.12 g, 67%); $^1$H NMR (600 MHz, CDCl$_3$) δ 7.69 (d, J=8.0 Hz, 1H), 7.59 (t, J=7.6 Hz, 1H), 7.53 (d, J=8.0 Hz, 1H), 7.35 (t, J=7.6 Hz, 1H), 3.60 (hept, J=6.8 Hz, 1H), 1.29 (d, J=6.8 Hz, 6H); $^{13}$C NMR (150 MHz, CDCl$_3$) δ 164.1, 153.8, 150.0, 133.5, 129.3, 126.9, 126.4, 118.3, 30.3, 23.6; IR (cm$^{-1}$) 2967, 1858, 1829, 1337, 1047, 970, 758; HRMS (EI) m/z calcd. for C$_{11}$H$_{11}$NO$_3$ [M]$^+$: 205.0739, found: 205.0737.

[Preparation Example 63] Preparation of (S)-3-(3-Methylpentyl)-1,4,2-dioxazol-5-one

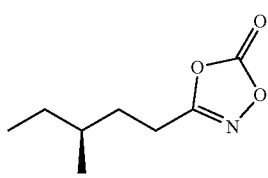

Prepared on a 7.65 mmol scale; colorless liquid (0.93 g, 71%, 2 steps yield from carboxylic acid); $^1$H NMR (400 MHz, CDCl$_3$) δ 2.73-2.56 (m, 2H), 1.82-1.71 (m, 1H), 1.60-1.49 (m, 1H), 1.49-1.35 (m, 2H), 1.29-1.18 (m, 1H), 0.97-0.88 (m, 6H); $^{13}$C NMR (100 MHz, CDCl$_3$) δ 167.2, 154.4, 33.9, 31.2, 29.1, 22.8, 18.7, 11.3; IR (cm$^{-1}$) 2962, 1859, 1825, 1147, 979; HRMS (ESI) m/z calcd. for C$_8$H$_{13}$NO$_3$ [M+Na]$^+$: 194.0788, found: 190.0794.

[Preparation Example 64] Preparation of 3-butyl-1,4,2-dioxazol-5-one

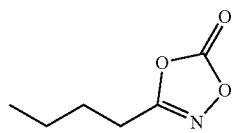

Prepared on a 3.5 mmol scale; Colorless liquid (0.39 g, 78%); $^1$H NMR (600 MHz, CDCl$_3$) δ 2.63 (t, J=7.5 Hz, 2H), 1.71 (p, J=7.6 Hz, 2H), 1.44 (h, J=7.4 Hz, 2H), 0.97 (t, J=7.4 Hz, 3H); $^{13}$C NMR (150 MHz, CDCl$_3$) δ 166.7, 154.2, 26.5, 24.4, 21.8, 13.4; IR (cm$^{-1}$) 2963, 1824, 1634, 1148, 980, 761; HRMS (EI) m/z calcd. for C$_6$H$_9$NO$_3$ [M]$^+$: 143.0582, found: 143.0583.

[Preparation Example 65] Preparation of 3-(cyclopentylmethyl)-1,4,2-dioxazol-5-one

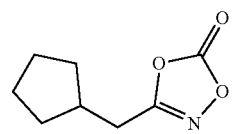 [SMILES: O=c1onc(CC2CCCC2)o1]

Prepared on a 4.4 mmol scale; Colorless liquid (0.70 g, 94%); $^1$H NMR (600 MHz, CDCl$_3$) δ 2.60 (d, J=7.4 Hz, 2H), 2.23 (hept, J=7.8 Hz, 1H), 1.88 (dq, J=11.9, 6.8 Hz, 2H), 1.71-1.64 (m, 2H), 1.64-1.56 (m, 2H), 1.24 (dq, J=15.0, 7.6 Hz, 2H); $^{13}$C NMR (150 MHz, CDCl$_3$) δ 166.4, 154.2, 35.9, 32.3, 30.5, 24.9; IR (cm$^{-1}$) 2952, 2869, 1868, 1825, 1631, 1149, 980; HRMS (EI) m/z calcd. for C$_8$H$_{11}$NO$_3$ [M]$^+$: 169.0739, found: 169.0739.

[Preparation Example 66] Preparation of 3-((adamantan-1-yl)methyl)-1,4,2-dioxazol-5-one

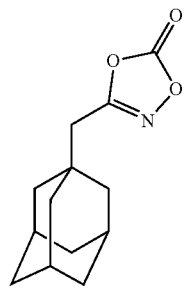 [SMILES: O=c1onc(CC23CC4CC(CC(C4)C2)C3)o1]

White solid (1.13 g, 96%); $^1$H NMR (600 MHz, CDCl$_3$) δ 2.36 (s, 2H), 2.01 (s, 3H), 1.72 (d, J=12.2 Hz, 3H), 1.65-1.58 (m, 9H); $^{13}$C NMR (150 MHz, CDCl$_3$) δ 165.0, 154.3, 42.1, 38.8, 36.3, 33.2, 28.3; IR (cm$^{-1}$) 2903, 2885, 2848, 1813, 1152, 985; HRMS (EI) m/z calcd. for C$_{13}$H$_{17}$NO$_3$ [M]$^+$: 235.1208, found: 235.1206.

[Preparation Example 67] Preparation of 3-neopentyl-1,4,2-dioxazol-5-one

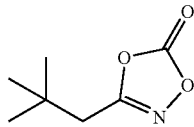

Colorless oil (0.55 g, 70%); $^1$H NMR (600 MHz, CDCl$_3$) δ 2.51 (s, 2H), 1.08 (s, 9H); $^{13}$C NMR (150 MHz, CDCl$_3$) δ 165.6, 154.2, 38.4, 31.3, 29.4; IR (cm$^{-1}$) 2963, 1829, 1629, 1352, 1143, 981.

[Preparation Example 68] Preparation of 3-(pent-4-en-1-yl)-1,4,2-dioxazol-5-one

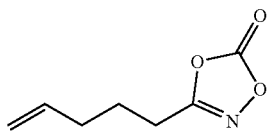

Colorless oil (0.44 g, 60%); $^1$H NMR (600 MHz, CDCl$_3$) δ 5.76 (ddt, J=17.0, 10.4, 6.7 Hz, 1H), 5.12-5.04 (m, 2H), 2.64 (t, J=7.5 Hz, 2H), 2.18 (q, J=6.6 Hz, 2H), 1.84 (p, J=7.4 Hz, 2H); $^{13}$C NMR (150 MHz, CDCl$_3$) δ 166.5, 154.1, 136.2, 116.6, 32.4, 23.9, 23.5; IR (cm$^{-1}$) 1868, 1824, 1638, 1148, 979, 761; HRMS (EI) m/z calcd. for C$_7$H$_9$NO$_3$ [M]$^+$: 155.0582, found: 155.0584.

[Preparation Example 69] Preparation of (E)-3-(5-phenylpent-4-en-1-yl)-1,4,2-dioxazol-5-one

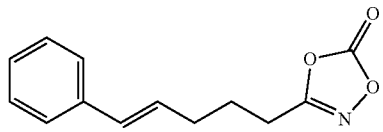 [SMILES: O=c1onc(CCC/C=C/c2ccccc2)o1]

Prepared on a 2.6 mmol scale; Colorless oil (0.36 g, 96%); $^1$H NMR (600 MHz, CDCl$_3$) δ 7.35 (d, J=7.4 Hz, 2H), 7.31 (t, J=7.2 Hz, 2H), 7.23 (t, J=7.1 Hz, 1H), 6.45 (d, J=15.8 Hz, 1H), 6.15 (dt, J=15.7, 6.9 Hz, 1H), 2.68 (t, J=7.4 Hz, 2H), 2.35 (q, J=7.0 Hz, 2H), 1.93 (q, J=7.3 Hz, 2H); $^{13}$C NMR (150 MHz, CDCl$_3$) δ 166.5, 154.1, 137.0, 132.0, 128.6, 127.7, 127.4, 126.0, 31.8, 24.1, 24.1; IR (cm$^{-1}$) 1868, 1824, 1633, 1146, 965, 740; HRMS (EI) m/z calcd. for C$_{13}$H$_{13}$NO$_3$ [M]$^+$: 231.0895, found: 231.0896.

[Preparation Example 70] Preparation of 3-(4-phenylpent-4-en-1-yl)-1,4,2-dioxazol-5-one

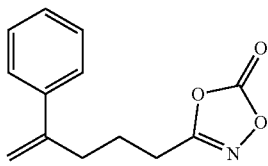 [SMILES: C=C(CCCc1noc(=O)o1)c1ccccc1]

Prepared on a 2.6 mmol scale; Colorless oil (0.58 g, 94%); $^1$H NMR (600 MHz, CDCl$_3$) δ 7.40-7.33 (m, 4H), 7.30 (t, J=7.0 Hz, 1H), 5.35 (s, 1H), 5.11 (s, 1H), 2.67-2.60 (m, 4H), 1.88 (p, J=8.1, 7.3 Hz, 2H); $^{13}$C NMR (150 MHz, CDCl$_3$) δ 166.4, 154.0, 146.3, 140.1, 128.5, 127.8, 126.1, 114.0, 34.1, 24.0, 22.7; IR (cm$^{-1}$) 1870, 1825, 1630, 1147, 979, 704; HRMS (EI) m/z calcd. for C$_{13}$H$_{13}$NO$_3$ [M]$^+$: 231.0895, found: 231.0896.

[Preparation Example 71] Preparation of 3-(5-phenylpent-4-yn-1-yl)-1,4,2-dioxazol-5-one

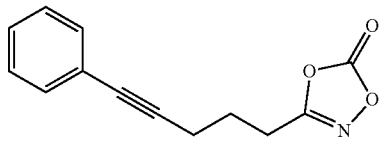 [SMILES: O=c1onc(CCCC#Cc2ccccc2)o1]

Colorless oil (1.0 g, 88%); $^1$H NMR (400 MHz, CD$_2$Cl$_2$) δ 7.42-7.36 (m, 2H), 7.32-7.27 (m, 3H), 2.84 (t, J=7.5 Hz, 2H), 2.58 (t, J=6.7 Hz, 2H), 2.02 (p, J=7.0 Hz, 2H); $^{13}$C NMR (150 MHz, CD$_2$Cl$_2$) δ 166.5, 154.2, 131.4, 128.3, 127.9, 123.3, 87.4, 82.0, 23.8, 23.5, 18.5; IR (cm$^{-1}$) 1870, 1823, 1634, 1146, 979, 754, 691; HRMS (EI) m/z calcd. for C$_{13}$H$_{11}$NO$_3$ [M]$^+$: 229.0739, found: 229.0741.

[Preparation Example 72] Preparation of 3-(6-phenylhex-4-yn-1-yl)-1,4,2-dioxazol-5-one

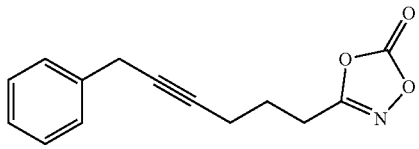 [SMILES: O=c1onc(CCCC#CCc2ccccc2)o1]

Prepared on a 1 mmol scale; Yellow oil (0.18 g, 75%); $^1$H NMR (600 MHz, CD$_2$Cl$_2$) δ 7.36-7.28 (m, 4H), 7.23 (t, J=6.5 Hz, 1H), 3.58 (s, 2H), 2.79 (t, J=7.5 Hz, 2H), 2.44-2.36 (m, 2H), 1.94 (p, J=7.0 Hz, 2H); $^{13}$C NMR (150 MHz, CD$_2$Cl$_2$) δ 166.5, 154.2, 137.2, 128.4, 127.7, 126.4, 79.8, 79.6, 24.9, 23.8, 23.7, 17.9; IR (cm$^{-1}$) 2939, 1869, 1825, 1636, 1149, 982, 760; HRMS (EI) m/z calcd. for C$_{14}$H$_{13}$NO$_3$ [M]$^+$: 243.0895, found: 243.0899.

[Preparation Example 73] Preparation of 3-(hex-4-yn-1-yl)-1,4,2-dioxazol-5-one

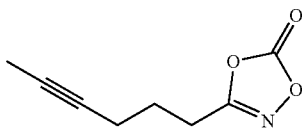

Prepared on a 1 mmol scale; Colorless oil (0.16 g, 96%); $^1$H NMR (600 MHz, CD$_2$Cl$_2$) δ 2.77 (t, J=7.5 Hz, 2H), 2.32-2.24 (m, 2H), 1.88 (p, J=6.8 Hz, 2H), 1.77 (s, 3H); $^{13}$C NMR (150 MHz, CD$_2$Cl$_2$) δ 166.6, 154.2, 77.3, 76.5, 23.8, 23.7, 17.8, 3.0; IR (cm$^{-1}$) 2920, 1869, 1825, 1634, 1148, 982, 759; HRMS (EI) m/z calcd. for $C_8H_9NO_3$ [M]$^+$: 167.0582, found: 167.0583.

[Preparation Example 74] Preparation of 3-(2-benzylbutyl)-1,4,2-dioxazol-5-one

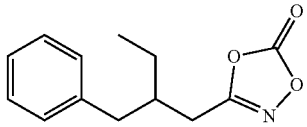 [SMILES: CCC(Cc1ccccc1)Cc1noc(=O)o1]

Prepared on a 1.2 mmol scale; Colorless oil (0.27 g, 96%); $^1$H NMR (600 MHz, CDCl$_3$) δ 7.31 (t, J=7.5 Hz, 2H), 7.23 (t, J=7.2 Hz, 1H), 7.16 (d, J=7.5 Hz, 2H), 2.82 (dd, J=13.9, 6.0 Hz, 1H), 2.56-2.50 (m, 3H), 2.12 (hept, J=6.6 Hz, 1H), 1.45 (dh, J=14.5, 7.2 Hz, 2H), 1.00 (t, J=7.4 Hz, 3H); $^{13}$C NMR (150 MHz, CDCl$_3$) 166.0, 154.0, 138.9, 129.1, 128.6, 126.6, 39.6, 38.4, 28.2, 26.2, 10.8; IR (cm$^{-1}$) 2964, 1869, 1826, 1145, 979, 699; HRMS (FAB) m/z calcd. for $C_{13}H_{15}NO_3$ [M+H]$^+$: 234.1130, found: 234.1133.

[Preparation Example 75] Preparation of 3-(2-benzyl-3-methylbutyl)-1,4,2-dioxazol-5-one

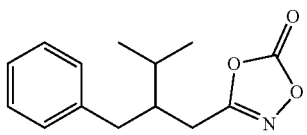 [SMILES: CC(C)C(Cc1ccccc1)Cc1noc(=O)o1]

Prepared on a 1.2 mmol scale; Colorless oil (0.24 g, 80%); $^1$H NMR (400 MHz, CD$_2$Cl$_2$) δ 7.29 (t, J=7.3 Hz, 2H), 7.24-7.13 (m, 3H), 2.84 (dd, J=13.9, 5.5 Hz, 1H), 2.58 (dd, J=15.7, 6.5 Hz, 1H), 2.52-2.40 (m, 2H), 2.15-2.06 (m, 1H), 1.86-1.74 (m, 1H), 0.98 (dd, J=19.0, 6.9 Hz, 6H); $^{13}$C NMR (150 MHz, CD$_2$Cl$_2$) δ 166.6, 154.1, 139.6, 129.0, 128.4, 126.3, 42.8, 36.6, 29.7, 26.0, 18.4; IR (cm$^{-1}$) 2960, 1869, 1825, 1631, 980, 699; HRMS (FAB) m/z calcd. for $C_{14}H_{17}NO_3$ [M+H]$^+$: 248.1287, found: 248.1285.

[Preparation Example 76] Preparation of (S)-2-(3-methyl-1-(5-oxo-1,4,2-dioxazol-3-yl)butyl)isoindoline-1,3-dione

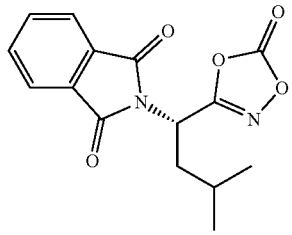 [SMILES: CC(C)C[C@@H](c1noc(=O)o1)N1C(=O)c2ccccc2C1=O]

White solid (0.93 g, 62%); $^1$H NMR (400 MHz, CDCl$_3$) δ 7.91 (dd, J=5.5, 3.1 Hz, 2H), 7.80 (dd, J=5.5, 3.1 Hz, 2H), 5.43 (dd, J=10.7, 4.7 Hz, 1H), 2.48-2.37 (m, 1H), 1.98 (ddd, J=14.3, 9.6, 4.7 Hz, 1H), 1.67-1.56 (m, 1H), 0.99 (dd, J=8.8, 6.6 Hz, 6H); $^{13}$C NMR (150 MHz, CDCl$_3$) δ 166.8, 164.3, 153.3, 134.8, 131.2, 124.0, 43.7, 36.4, 24.5, 22.8, 21.2; IR (cm$^{-1}$) 2959, 2924, 2876, 1830, 1716, 1380, 989, 756, 711; HRMS (EI) m/z calcd. for $C_{15}H_{14}N_2O_5$ [M]$^+$: 302.0903, found: 302.0904.

[Preparation Example 77] Preparation of (S)-2-(1-(5-oxo-1,4,2-dioxazol-3-yl)-3-phenylpropyl)isoindoline-1,3-dione

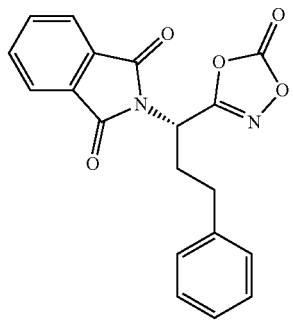 [SMILES: O=C1c2ccccc2C(=O)N1[C@@H](CCc1ccccc1)c1noc(=O)o1]

Prepared on a 2.0 mmol scale; White solid (0.44 g, 62%); $^1$H NMR (400 MHz, CDCl$_3$) δ 7.86 (dd, J=5.5, 3.0 Hz, 2H), 7.78 (dd, J=5.5, 3.1 Hz, 2H), 7.20 (t, J=7.5 Hz, 2H), 7.14 (d, J=6.6 Hz, 2H), 7.08 (t, J=7.2 Hz, 1H), 5.36 (t, J=4.8 Hz, 1H), 2.85-2.73 (m, 3H), 2.61-2.52 (m, 1H); $^{13}$C NMR (150 MHz, CDCl$_3$) δ 166.7, 163.9, 153.3, 138.9, 134.7, 131.2, 128.6, 128.3, 126.4, 123.9, 44.9, 31.8, 28.9; IR (cm$^{-1}$) 1834, 1781, 1716, 1381, 754; HRMS (EI) m/z calcd. for $C_{19}H_{14}N_2O_5$ [M]$^+$: 350.0903, found: 350.0900.

[Preparation Example 78] Preparation of (R)-2-(3-Methyl-1-(5-oxo-1,4,2-dioxazol-3-yl)butan-2-yl)isoindoline-1,3-dione

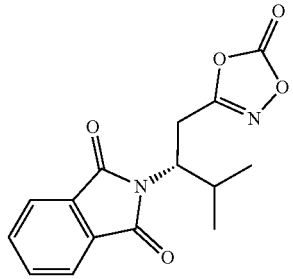 [SMILES: CC(C)[C@@H](Cc1noc(=O)o1)N1C(=O)c2ccccc2C1=O]

Prepared on a 2.0 mmol scale; White solid (0.22 g, 38%); $^1$H NMR (400 MHz, CDCl$_3$) δ 7.85-7.79 (m, 2H), 7.76-7.70 (m, 2H), 4.23 (ddd, J=10.9, 9.9, 3.5 Hz, 1H), 3.60 (dd, J=16.0, 11.0 Hz, 1H), 3.08 (dd, J=16.0, 3.6 Hz, 1H), 2.57-2.41 (m, 1H), 1.10 (d, J=6.7 Hz, 3H), 0.88 (d, J=6.7 Hz, 3H); $^{13}$C NMR (100 MHz, CDCl$_3$) δ 168.2, 164.7, 153.7, 134.5, 131.2, 123.7, 53.8, 30.4, 25.8, 20.2, 19.7; IR (cm$^{-1}$) 2967, 1865, 1828, 1703, 979, 719; HRMS (EI) m/z calcd. for $C_{15}H_{14}N_2O_5$ [M]$^+$: 302.0903, found: 302.0904.

[Preparation Example 79] Preparation of 2-((1-((5-oxo-1,4,2-dioxazol-3-yl)methyl)cyclohexyl)methyl)isoindoline-1,3-dione

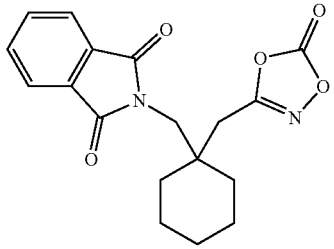 [SMILES: O=C1c2ccccc2C(=O)N1CC1(Cc2noc(=O)o2)CCCCC1]

Prepared on a 2.0 mmol scale; White solid (0.36 g, 52%); $^1$H NMR (400 MHz, CDCl$_3$) δ 7.84 (dd, J=5.5, 3.1 Hz, 2H), 7.74 (dd, J=5.5, 3.1 Hz, 2H), 3.76 (s, 2H), 2.72 (s, 2H), 1.74-1.63 (m, 2H), 1.52-1.42 (m, 8H); $^{13}$C NMR (100 MHz, CDCl$_3$) δ 169.2, 165.2, 154.1, 134.4, 131.8, 123.6, 45.4, 38.7, 33.5, 32.0, 25.4, 21.4; IR (cm$^{-1}$) 2922, 1824, 1707, 1390, 984, 711; HRMS (EI) m/z calcd. for C$_{18}$H$_{18}$N$_2$O$_5$ [M]$^+$: 342.1216, found: 342.1212.

[Preparation Example 80] Preparation of tert-butyl ([1-{(5-oxo-1,4,2-dioxazol-3-yl)methyl}cyclohexyl]methyl)carbamate

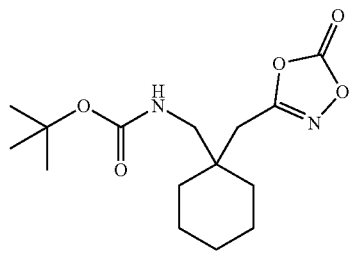 [SMILES: CC(C)(C)OC(=O)NCC1(Cc2noc(=O)o2)CCCCC1]

Prepared at 1.0 mmol scale; Colorless oil (0.23 g, 75%); $^1$H NMR (400 MHz, Methylene Chloride-d$_2$) δ 4.78 (s, 1H), 3.14 (d, J=6.9 Hz, 2H), 2.62 (s, 2H), 1.62-1.33 (m, 19H); $^{13}$C NMR (100 MHz, Methylene Chloride-d$_2$) δ 165.5, 156.1, 154.1, 79.1, 46.5, 38.1, 33.3, 31.3, 28.0, 25.6, 21.3; IR (cm$^{-1}$) 3349, 2929, 1829, 1698, 1628, 1510, 1455, 1365, 1246, 1163, 983, 763; HRMS (FAB) m/z calcd. for C$_{15}$H$_{24}$N$_2$O$_5$ [M+H]$^+$: 313.1763, found: 313.1760.

[Preparation Example 81] Preparation of anti-(Z)-3-((3-oxo-2-(pent-2-en-1-yl)cyclopentyl)methyl)-1,4,2-dioxazol-5-one

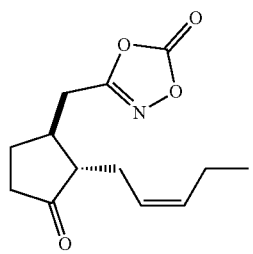

Prepared on a 1.8 mmol scale; Colorless oil (0.34 g, 77%); $^1$H NMR (600 MHz, CDCl$_3$) δ 5.53-5.47 (m, 1H), 5.23 (q, J=8.7, 8.2 Hz, 1H), 3.04 (dd, J=15.6, 4.3 Hz, 1H), 2.63 (dd, J=15.6, 9.2 Hz, 1H), 2.49-2.24 (m, 6H), 2.20-2.13 (m, 1H), 2.05 (p, J=7.4 Hz, 2H), 1.98-1.93 (m, 1H), 1.62-1.54 (m, 1H), 0.97 (t, J=7.6 Hz, 3H); $^{13}$C NMR (150 MHz, CDCl$_3$) δ 216.8, 165.1, 153.7, 134.8, 124.3, 53.8, 37.8, 37.4, 29.6, 27.0, 25.7, 20.6, 14.0; IR (cm$^{-1}$) 2963, 1870, 1826, 1736, 1147, 979; HRMS (EI) m/z calcd. for C$_{13}$H$_{17}$NO$_4$ [M]$^+$: 251.1158, found: 251.1155.

[Preparation Example 82] Preparation of 3-((3R)-3-((3R,8R,9S,10S,13R,14S,17R)-3-methoxy-10,13-dimethylhexadecahydro-1H-cyclopenta[a]phenanthren-17-yl)butyl)-1,4,2-dioxazol-5-one

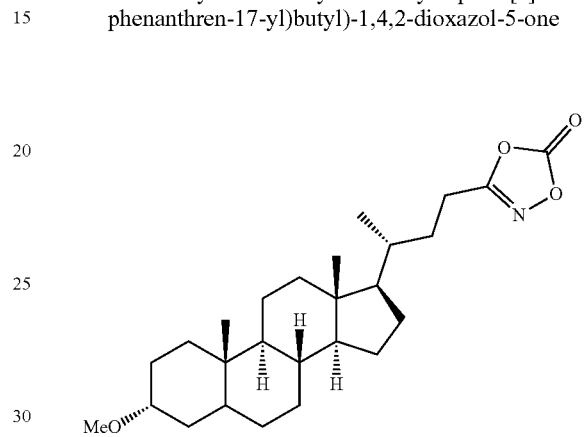

Prepared on a 3.0 mmol scale; White solid (1.23 g, 95%); $^1$H NMR (600 MHz, CDCl$_3$) δ 3.35 (s, 3H), 3.16 (dt, J=10.9, 5.6 Hz, 1H), 2.66 (ddd, J=15.2, 7.4, 3.4 Hz, 1H), 2.57-2.48 (m, 1H), 1.94 (d, J=12.4 Hz, 1H), 1.89-1.81 (m, 3H), 1.81-1.73 (m, 2H), 1.68 (q, J=12.7, 12.2 Hz, 1H), 1.59 (d, J=11.8 Hz, 2H), 1.50-1.34 (m, 7H), 1.28-1.21 (m, 4H), 1.09 (dt, J=33.9, 8.7 Hz, 5H), 0.97 (d, J=6.4 Hz, 3H), 0.94-0.92 (m, 4H), 0.65 (s, 3H); $^{13}$C NMR (150 MHz, CDCl$_3$) δ 167.1, 154.2, 80.4, 56.4, 55.6, 55.5, 42.8, 42.0, 40.3, 40.1, 35.8, 35.3, 35.2, 34.9, 32.7, 30.6, 28.2, 27.3, 26.8, 26.3, 24.1, 23.4, 21.8, 20.8, 18.0, 12.0; IR (cm$^{-1}$) 2923, 2865, 1856, 1822, 1634, 1091, 982; HRMS (EI) m/z calcd. for C$_{26}$H$_{41}$NO$_4$ [M]$^+$: 431.3036, found: 431.3033.

[Preparation Example 83] Preparation of 3-(2,6-dimethylhept-5-en-1-yl)-1,4,2-dioxazol-5-one

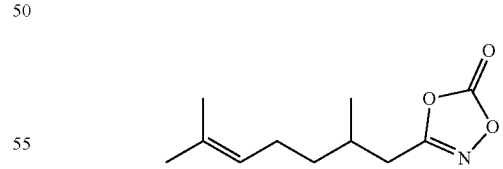

Prepared on a 3.2 mmol scale; Colorless oil (577 mg, 85%); $^1$H NMR (600 MHz, CDCl$_3$) δ 5.06 (t, J=7.0 Hz, 1H), 2.61 (dd, J=15.2, 5.8 Hz, 1H), 2.45 (dd, J=15.2, 8.1 Hz, 1H), 2.00 (tdd, J=27.5, 14.1, 7.0 Hz, 3H), 1.69 (s, 3H), 1.61 (s, 3H), 1.42 (td, J=14.7, 6.3 Hz, 1H), 1.32 (dt, J=13.7, 7.2 Hz, 1H), 1.02 (d, J=6.7 Hz, 3H); $^{13}$C NMR (150 MHz, CDCl$_3$) δ 166.1, 154.2, 132.4, 123.3, 36.3, 31.7, 29.8, 25.7, 25.1, 19.3, 17.7; IR (cm$^{-1}$) 2961, 1875, 1828, 1632, 1145, 979, 761; HRMS (EI) m/z calcd. for C$_{11}$H$_{17}$NO$_3$ [M]$^+$: 211.1208, found: 211.1209.

[Preparation Example 84] Preparation of 3-((S)-1-((2R,4aS)-4a,8-dimethyl-7-oxo-1,2,3,4,4a,7-hexahydronaphthalen-2-yl)ethyl)-1,4,2-dioxazol-5-one

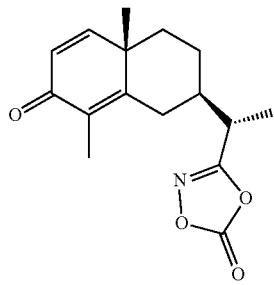 [SMILES: CC1=C2C[C@H]([C@H](C)c3noc(=O)o3)CC[C@@]2(C)C=CC1=O]

Prepared on a 1 mmol scale; White solid (0.14 g, 48%); $^1$H NMR (400 MHz, acetone-$d_6$) δ 6.85 (d, J=9.9 Hz, 1H), 6.09 (d, J=9.9 Hz, 1H), 3.14-3.04 (m, 1H), 2.95-2.85 (m, 1H), 2.24 (t, J=12.7 Hz, 1H), 1.98-1.89 (m, 1H), 1.87-1.69 (m, 6H), 1.42-1.27 (m, 4H), 1.24 (s, 3H); $^{13}$C NMR (100 MHz, acetone-$d_6$) δ 185.8, 169.7, 158.9, 157.1, 155.3, 130.0, 126.6, 42.1, 40.8, 38.1, 36.8, 31.8, 24.3, 23.7, 13.3, 10.5; IR (cm$^{-1}$) 2979, 2949, 2919, 1822, 1658, 1625, 980, 839; HRMS (EI) m/z calcd. for $C_{16}H_{19}NO_4$ [M]$^+$: 289.1314, found: 289.1312.

Example II: Preparation of Gamma-Lactam Compound from Dioxazol-One Compound

[Example 14] Preparation of 5-phenylpyrrolidin-2-one (1)

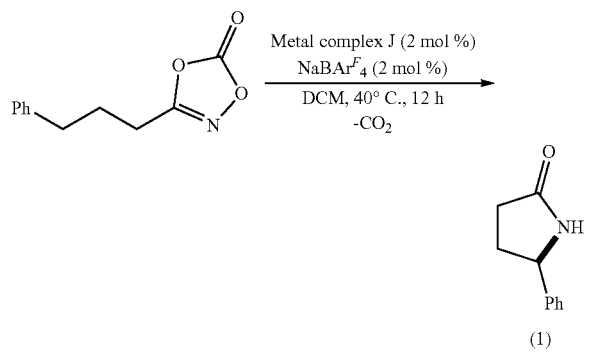

Metal complex J (2.4 mg, 2.0 mol %), sodium tetrakis[3,5-bis(trifluoromethyl)phenyl]borate (NaBAr$^F_4$, 4.5 mg, 2.0 mol %), and dichloromethane (2.4 mL) were added to a well-dried vial under an argon atmosphere, the mixture was stirred for 1 minute, 3-(3-phenylpropyl)-1,4,2-dioxazol-5-one (10.3 mg, 0.2 mmol) was added thereto, and the vial was sealed under an argon atmosphere. Thereafter, the reaction mixture was vigorously stirred at 40° C. for 12 hours, cooled to room temperature, filtered with celite, washed with dichloromethane (5 mL×4), and concentrated under reduced pressure. The concentrated residue was separated and purified with column chromatography (eluent: n-hexane/10% methanol-EtOAc solution, 2:1~1:1) to obtain the desired compound (35 mg, 95%).

5-Phenylpyrrolidin-2-one (1)

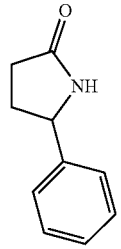 [SMILES: O=C1CCC(c2ccccc2)N1]

Catalyst J (2.4 mg, 2 mol %) was used. White solid (31 mg, 95%); $^1$H NMR (600 MHz, CDCl$_3$) δ 7.38-7.33 (m, 2H), 7.32-7.27 (m, 3H), 6.57 (br, 1H), 4.75 (t, J=7.1 Hz, 1H), 2.60-2.52 (m, 1H), 2.49-2.35 (m, 2H), 2.00-1.92 (m, 1H); $^{13}$C NMR (150 MHz, CDCl$_3$) δ 178.6, 142.5, 128.9, 127.8, 125.6, 58.1, 31.3, 30.3.

Gamma-lactam compounds having various structures were prepared in the same manner as in Example 14, except that the starting material, the reaction temperature, the catalyst, or the base was different, and the synthesis data of the prepared gamma-lactam compounds are shown in the following.

[Example 15] Preparation of 5-(4-bromophenyl)pyrrolidin-2-one (2)

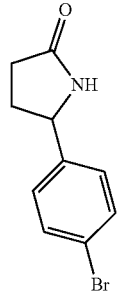

Catalyst J (2.4 mg, 2 mol %) was used. White solid (45 mg, 94%); m.p. 147-149° C.; $^1$H NMR (600 MHz, CDCl$_3$) δ 7.50 (d, J=8.4 Hz, 2H), 7.18 (d, J=8.3 Hz, 2H), 6.00 (s, 1H), 4.72 (t, J=7.1 Hz, 1H), 2.58 (dtd, J=12.8, 8.4, 7.8, 4.9 Hz, 1H), 2.45 (ddp, J=25.9, 17.2, 9.0 Hz, 2H), 1.93 (dt, J=15.8, 8.1 Hz, 1H); $^{13}$C NMR (150 MHz, CDCl$_3$) δ 178.1, 141.5, 132.0, 127.3, 121.8, 57.4, 31.3, 30.0; IR (cm$^{-1}$) 3175, 3074, 1677, 1262, 1008, 789; HRMS (EI) m/z calcd. for $C_{10}H_{10}BrNO$ [M]$^+$: 238.9946, found: 238.9943.

[Example 16] Preparation of 5-(4-fluorophenyl)pyrrolidin-2-one (3)

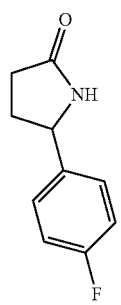 [SMILES: O=C1CCC(c2ccc(F)cc2)N1]

Catalyst J (2.4 mg, 2 mol %) was used. White solid (31 mg, 87%); m.p. 135-137° C.; $^1$H NMR (600 MHz, CDCl$_3$) δ 7.26-7.21 (m, 2H), 7.10 (s, 1H), 7.05-6.98 (m, 2H), 4.72 (t, J=7.1 Hz, 1H), 2.56-2.46 (m, 1H), 2.46-2.30 (m, 2H), 1.93-1.85 (m, 1H); $^{13}$C NMR (150 MHz, CDCl$_3$) δ 178.9, 162.4 (d, J=246.1 Hz), 138.4 (d, J=3.2 Hz), 127.4 (d, J=8.2 Hz), 115.8 (d, J=21.6 Hz), 57.7, 31.4, 30.5; $^{19}$F NMR (564 MHz, CDCl$_3$) δ −114.7 (m); IR (cm$^{-1}$) 3167, 3084, 1682, 1509, 1217, 793, 482; HRMS (EI) m/z calcd. for C$_{10}$H$_{10}$FNO [M]$^+$: 179.0746, found: 179.0745.

[Example 17] Preparation of 5-(4-nitrophenyl)pyrrolidin-2-one (4)

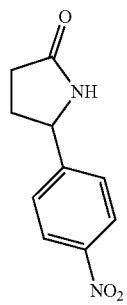 [SMILES: O=C1CCC(c2ccc([N+](=O)[O-])cc2)N1]

Catalyst J (2.4 mg, 2 mol %) was used. White solid (35 mg, 85%); m.p. 141-143° C.; $^1$H NMR (600 MHz, CDCl$_3$) δ 8.24 (d, J=8.6 Hz, 2H), 7.49 (d, J=8.6 Hz, 2H), 6.75 (s, 1H), 4.89 (t, J=7.2 Hz, 1H), 2.70-2.62 (m, 1H), 2.53-2.41 (m, 2H), 1.95 (dq, J=15.7, 8.5 Hz, 1H); $^{13}$C NMR (150 MHz, CDCl$_3$, one carbon merged to others) δ 149.9, 147.6, 126.4, 124.2, 57.4, 31.0, 30.2; IR (cm$^{-1}$) 3067, 1678, 1520, 1338; HRMS (EI) m/z calcd. for C$_{10}$H$_{10}$N$_2$O$_3$ [M]$^+$: 206.0691, found: 206.0688.

[Example 18] Preparation of 5-(4-methoxyphenyl)pyrrolidin-2-one (5)

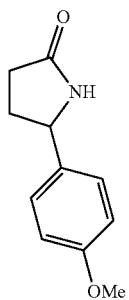 [SMILES: COc1ccc(C2CCC(=O)N2)cc1]

Catalyst J (2.4 mg, 2 mol %) was used. White solid (26 mg, 68%); m.p. 128-130° C.; $^1$H NMR (600 MHz, CDCl$_3$) δ 7.21 (d, J=8.3 Hz, 2H), 6.89 (d, J=8.2 Hz, 2H), 6.08 (s, 1H), 4.70 (t, J=7.2 Hz, 1H), 3.80 (s, 3H), 2.56-2.34 (m, 3H), 1.95 (dq, J=15.8, 8.3 Hz, 1H); $^{13}$C NMR (150 MHz, CDCl$_3$) δ 178.2, 159.3, 134.4, 126.9, 114.2, 57.0, 55.3, 31.6, 30.5; IR (cm$^{-1}$) 3179, 2918, 1681, 1515, 1241, 1022; HRMS (EI) m/z calcd. for C$_{11}$H$_{13}$NO$_2$ [M]$^+$: 191.0946, found: 191.0946.

[Example 19] Preparation of tert-butyl {4-(5-oxopyrrolidin-2-yl)phenyl}carbamate (6)

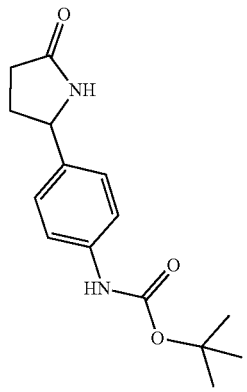 [SMILES: CC(C)(C)OC(=O)Nc1ccc(C2CCC(=O)N2)cc1]

Catalyst J (11.8 mg, 10 mol %) and NaBAr$^F_4$ (17.6 mg, 10 mol %) were used at 40° C. for 12 hours and further at 80° C. for 36 hours. White solid (36 mg, 67%); m.p. 201-203° C.; $^1$H NMR (400 MHz, CDCl$_3$) δ 7.36 (d, J=8.2 Hz, 2H), 7.21 (d, J=8.6 Hz, 2H), 6.59 (s, 1H), 5.92 (s, 1H), 4.70 (t, J=7.1 Hz, 1H), 2.59-2.50 (m, 1H), 2.49-2.34 (m, 2H), 2.00-1.88 (m, 1H), 1.51 (s, 9H); $^{13}$C NMR (150 MHz, CDCl$_3$) δ 178.2, 152.7, 138.2, 136.8, 126.3, 119.0, 80.7, 57.6, 31.5, 30.3, 28.3; IR (cm$^{-1}$) 2968, 1782, 1746, 1718, 1271; HRMS (FAB) m/z calcd. for C$_{15}$H$_{20}$N$_2$O$_3$ [M+H]$^+$: 277.1552, found: 277.1550.

[Example 20] Preparation of 3,3-dimethyl-5-phenylpyrrolidin-2-one (7)

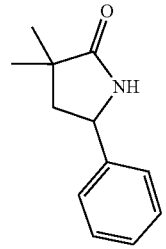

Catalyst J (11.8 mg, 10 mol %) and NaBAr$^F_4$ (17.7 mg, 10 mol %) were used at 80° C. White solid (20 mg, 53%); m.p. 161-163° C.; $^1$H NMR (600 MHz, CDCl$_3$) δ 7.37 (t, J=7.5 Hz, 2H), 7.31 (d, J=7.5 Hz, 3H), 5.85 (s, 1H), 4.68 (t, J=7.8 Hz, 1H), 2.38 (dd, J=12.8, 6.9 Hz, 1H), 1.84 (dd, J=12.8, 8.6 Hz, 1H), 1.26 (s, 3H), 1.22 (s, 3H); $^{13}$C NMR (150 MHz, CDCl$_3$) δ 182.6, 142.3, 128.9, 127.9, 125.7, 54.7, 47.4, 25.1, 24.5; IR (cm$^{-1}$) 3169, 3076, 2968, 2924, 1677, 1260, 701; HRMS (EI) m/z calcd. for C$_{12}$H$_{15}$NO [M]$^+$: 189.1154, found: 189.1152.

[Example 21] Preparation of 3-methyl-5-phenylpyrrolidin-2-one (8)

Using Catalyst K (2.4 mg, 2 mol %). White solid (19 mg, 53%); $^1$H NMR spectroscopic analysis of the unpurified reaction mixture represented 1:0.8 dr.

cis-3-Methyl-5-phenylpyrrolidin-2-one (8-A)

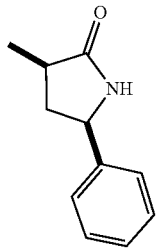

Major Diastereomer:
m.p. 101-103° C.; ¹H NMR (600 MHz, CDCl₃) δ 7.40-7.34 (m, 2H), 7.33-7.28 (m, 3H), 5.85 (s, 1H), 4.69-4.59 (m, 1H), 2.77-2.66 (m, 1H), 2.65-2.52 (m, 1H), 1.66-1.55 (m, 1H), 1.25 (d, J=7.0 Hz, 3H); ¹³C NMR (150 MHz, CDCl₃) δ 180.4, 142.2, 129.1, 128.2, 126.0, 56.6, 41.2, 37.3, 15.9; IR (cm⁻¹) 3193, 2926, 1682, 1284, 758, 697, 482; HRMS (EI) m/z calcd. for C₁₁H₁₃NO [M]⁺: 175.0997, found: 175.0996.

trans-3-Methyl-5-phenylpyrrolidin-2-one (8-B)

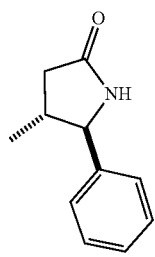

Minor Diastereomer:
m.p. 120-122° C.; ¹H NMR (400 MHz, CDCl₃) δ 7.40-7.33 (m, 2H), 7.33-7.25 (m, 3H), 6.00 (s, 1H), 4.77-4.69 (m, 1H), 2.70-2.54 (m, 1H), 2.31-2.15 (m, 2H), 1.25 (d, J=7.2 Hz, 3H); ¹³C NMR (100 MHz, CDCl₃) δ 181.1, 142.8, 129.0, 127.9, 125.6, 55.7, 39.6, 34.9, 16.1; IR (cm⁻¹) 3224, 2969, 1680, 1283, 737, 698; HRMS (ESI) m/z calcd. for C₁₁H₁₃NO [M+H]⁺: 176.1070, found: 176.1062.

[Example 22] Preparation of trans-4-methyl-5-phenylpyrrolidin-2-one (9)

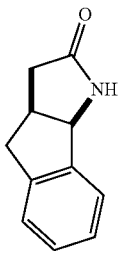

Catalyst J (2.4 mg, 2 mol %) was used. White solid (35 mg, 99%); ¹H NMR spectroscopic analysis of the unpurified reaction mixture indicated >20:1 dr; m.p. 116-118° C.; ¹H NMR (600 MHz, CDCl₃) δ 7.37 (t, J=7.3 Hz, 2H), 7.34-7.29 (m, 3H), 5.90 (br, 1H), 4.22 (d, J=7.3 Hz, 1H), 2.61 (dd, J=16.7, 8.2 Hz, 1H), 2.30 (dp, J=14.7, 6.8 Hz, 1H), 2.13 (dd, J=16.7, 9.5 Hz, 1H), 1.16 (d, J=6.7 Hz, 3H); ¹³C NMR (150 MHz, CDCl₃) δ 177.3, 141.0, 128.8, 128.1, 126.1, 65.9, 40.6, 38.8, 17.7; IR (cm⁻¹) 3175, 2966, 1674, 1340, 751, 702; HRMS (EI) m/z calcd. for C₁₁H₁₃NO [M]⁺: 175.0997, found: 175.0995.

[Example 23] Preparation of cis-3,3a,4,8b-tetrahydroindeno[1,2-b]pyrrol-2(1H)-one (10)

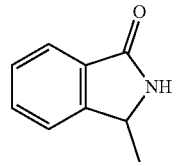

Catalyst J (2.4 mg, 2 mol %) was used. White solid (34 mg, 99%); ¹H NMR spectroscopic analysis of the unpurified reaction mixture indicated >20:1 dr; m.p. 215-217° C.; ¹H NMR (600 MHz, CDCl₃) δ 7.30-7.22 (m, 4H), 6.48 (br, 1H), 5.02 (d, J=6.9 Hz, 1H), 3.35-3.27 (m, 2H), 2.90-2.83 (m, 1H), 2.71 (dd, J=17.3, 9.2 Hz, 1H), 2.22 (dd, J=17.4, 4.6 Hz, 1H); ¹³C NMR (150 MHz, CDCl₃) δ 177.4, 142.5, 141.5, 128.7, 127.2, 125.4, 124.7, 63.2, 38.5, 37.6, 37.4; IR (cm⁻¹) 3207, 1692, 1645, 748; HRMS (EI) m/z calcd. for C₁₁H₁₁NO [M]⁺: 173.0841, found: 173.0842.

[Example 24] Preparation of 3-methylisoindolin-1-one (11)

Using Catalyst K (5.9 mg, 5 mol %) and NaBArᶠ₄ (8.8 mg, 5 mol %). White solid (22 mg, 75%); m.p. 114-116° C.; ¹H NMR (600 MHz, CDCl₃) δ 7.85 (d, J=7.6 Hz, 1H), 7.58 (t, J=7.9 Hz, 1H), 7.47 (t, J=7.5 Hz, 1H), 7.43 (d, J=8.0 Hz, 1H), 6.75 (s, 1H), 4.70 (q, J=6.8 Hz, 1H), 1.51 (d, J=6.7 Hz, 3H); ¹³C NMR (150 MHz, CDCl₃) δ 170.5, 148.8, 131.9, 131.4, 128.1, 123.8, 122.2, 52.4, 20.3; IR (cm⁻¹) 3219, 1693, 1655, 721, 682; HRMS (EI) m/z calcd. for C₉H₉NO [M]⁺: 147.0684, found: 147.0685.

[Example 25] Preparation of 3-phenylisoindolin-1-one (12)

Catalyst J (5.9 mg, 5 mol %) and NaBAr$^F_4$ (8.8 mg, 5 mol %) were used. White solid (37 mg, 88%); m.p. 216-218° C.; $^1$H NMR (600 MHz, CDCl$_3$) δ 7.89 (d, J=7.3 Hz, 1H), 7.49 (dt, J=21.2, 7.3 Hz, 2H), 7.38-7.31 (m, 3H), 7.28-7.25 (m, 2H), 7.23 (d, J=7.4 Hz, 1H), 6.63 (s, 1H), 5.62 (s, 1H); $^{13}$C NMR (150 MHz, CDCl$_3$) δ 170.9, 147.9, 138.4, 132.3, 130.7, 129.1, 128.5, 128.3, 126.8, 123.8, 123.3, 60.7; IR (cm$^{-1}$) 3172, 3055, 2855, 1680, 740, 695; HRMS (EI) m/z calcd. for C$_{14}$H$_{11}$NO [M]$^+$: 209.0841, found: 209.0842.

[Example 26] Preparation of 5-(benzofuran-2-yl)pyrrolidin-2-one (13)

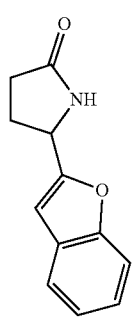 [SMILES: O=C1CCC(c2cc3ccccc3o2)N1]

Catalyst J (11.8 mg, 10 mol %) and NaBAr$^F_4$ (17.7 mg, 10 mol %) were used. White solid (37 mg, 92%); m.p. 122-124° C.; $^1$H NMR (600 MHz, CDCl$_3$) δ 7.53 (d, J=7.7 Hz, 1H), 7.45 (d, J=8.2 Hz, 1H), 7.30-7.26 (m, 1H), 7.23 (t, J=7.5 Hz, 1H), 6.61 (s, 1H), 6.30 (s, 1H), 4.91 (dd, J=7.6, 4.7 Hz, 1H), 2.62-2.54 (m, 2H), 2.46-2.39 (m, 1H), 2.38-2.31 (m, 1H); $^{13}$C NMR (150 MHz, CDCl$_3$) δ 178.0, 157.1, 155.0, 127.8, 124.5, 123.0, 121.0, 111.2, 102.8, 51.7, 29.3, 26.9; IR (cm$^{-1}$) 3193, 3072, 1688, 1257, 812, 743; HRMS (EI) m/z calcd. for C$_{12}$H$_{11}$NO$_2$ [M]$^+$: 201.0790, found: 201.0790.

[Example 27] Preparation of 5-(thiophen-2-yl)pyrrolidin-2-one (14)

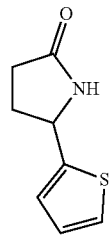 [SMILES: O=C1CCC(c2cccs2)N1]

Catalyst J (11.8 mg, 10 mol %) and NaBAr$^F_4$ (17.7 mg, 10 mol %) were used at 80° C. White solid (28 mg, 84%); m.p. 112-114° C.; $^1$H NMR (600 MHz, CDCl$_3$) δ 7.30-7.22 (m, 1H), 7.02-6.94 (m, 2H), 6.32 (s, 1H), 5.03 (t, J=6.8 Hz, 1H), 2.66-2.48 (m, 2H), 2.48-2.35 (m, 1H), 2.20-2.08 (m, 1H); $^{13}$C NMR (150 MHz, CDCl$_3$) δ 177.7, 146.4, 126.9, 124.8, 124.1, 53.8, 31.7, 30.0; IR (cm$^{-1}$) 3165, 3069, 1677, 1260, 784, 698, 481; HRMS (EI) m/z calcd. for C$_8$H$_9$NOS [M]$^+$: 167.0405, found: 167.0404.

[Example 28] Preparation of 5,5-dimethylpyrrolidin-2-one (15)

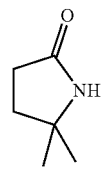

Catalyst J (2.4 mg, 2 mol %) was used. White solid (20 mg, 88%); $^1$H NMR (600 MHz, CDCl$_3$) δ 6.35 (s, 1H), 2.40 (t, J=7.9 Hz, 2H), 1.91 (t, J=7.9 Hz, 2H), 1.28 (s, 6H); $^{13}$C NMR (150 MHz, CDCl$_3$) δ 177.0, 56.5, 35.3, 30.6, 29.2.

[Example 29] Preparation of 1-azaspiro[4.5]decan-2-one (16)

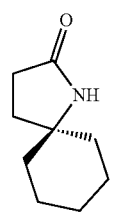

Catalyst J (2.4 mg, 2 mol %) was used. White solid (23 mg, 75%); m.p. 126-128° C.; $^1$H NMR (600 MHz, CDCl$_3$) 6.56 (s, 1H), 2.37 (t, J=8.1 Hz, 2H), 1.90 (t, J=8.1 Hz, 2H), 1.57-1.48 (m, 8H), 1.44-1.38 (m, 2H); $^{13}$C NMR (150 MHz, CDCl$_3$) δ 177.1, 59.2, 38.3, 32.7, 29.8, 25.1, 23.0; IR (cm$^{-1}$) 3209, 2929, 1683, 1264, 731, 701; HRMS (EI) m/z calcd. for C$_9$H$_{13}$NO [M]$^+$: 153.1154, found: 153.1156.

[Example 30] Preparation of 3,3-dimethylisoindolin-1-one (17)

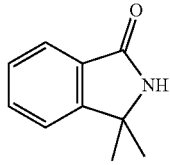

Prepared with Catalyst J (5.9 mg, 5 mol %) and NaBAr$^F_4$ (8.8 mg, 5 mol %). White solid (30 mg, 94%); m.p. 160-162° C.; $^1$H NMR (600 MHz, CDCl$_3$) δ 7.82 (d, J=7.6 Hz, 1H), 7.56 (t, J=7.5 Hz, 1H), 7.44 (t, J=7.5 Hz, 1H), 7.40 (d, J=7.7 Hz, 1H), 7.01 (s, 1H), 1.56 (s, 6H); $^{13}$C NMR (150 MHz, CDCl$_3$) δ 169.6, 153.0, 132.0, 130.6, 128.0, 123.8, 120.8, 59.0, 27.8; IR (cm$^{-1}$) 3199, 2967, 1689, 1264, 732; HRMS (EI) m/z calcd. for C$_{10}$H$_{11}$NO [M]$^+$: 161.0841, found: 161.0839.

[Example 31] Preparation of (R)-5-ethyl-5-methylpyrrolidin-2-one (18)

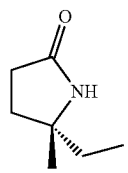

Catalyst J (2.4 mg, 2 mol %) was used. Colorless oil (21 mg, 83%); $^1$H NMR (400 MHz, CDCl$_3$) δ 6.86 (s, 1H), 2.44-2.28 (m, 2H), 1.93 (ddd, J=12.8, 8.9, 7.3 Hz, 1H), 1.80 (ddd, J=12.9, 9.2, 7.0 Hz, 1H), 1.57-1.46 (m, 2H), 1.21 (s, 3H), 0.89 (t, J=7.5 Hz, 3H); $^{13}$C NMR (100 MHz, CDCl$_3$) δ 177.5, 59.6, 34.6, 32.9, 30.6, 26.7, 8.4; IR (cm$^{-1}$) 3207, 2965, 1683, 1380; HRMS (FAB) m/z calcd. for C$_7$H$_{13}$NO [M+H]$^+$: 128.1075, found: 128.1077; Optical Rotation: [α]$_D$=−11.8 (c=1.0, benzene).

[Example 32] Preparation of 5-methylpyrrolidin-2-one (19)

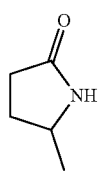

Using Catalyst K (5.9 mg, 5 mol %) and NaBAr$^F_4$ (8.8 mg, 5 mol %). $^1$H NMR (400 MHz, CDCl$_3$) δ 6.37 (s, 1H), 3.78 (q, J=6.4 Hz, 1H), 2.41-2.20 (m, 3H), 1.72-1.59 (m, 1H), 1.22 (d, J=6.2 Hz, 3H); $^{13}$C NMR (150 MHz, CDCl$_3$) δ 178.1, 50.0, 30.5, 29.2, 22.2.

[Example 33] Preparation of cis-hexahydrocyclopenta[b]pyrrol-2(1H)-one (20)

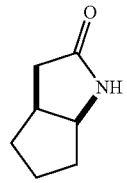

Using Catalyst K (5.9 mg, 5 mol %) and NaBAr$^F_4$ (8.8 mg, 5 mol %). White solid (18 mg, 72%); $^1$H NMR spectroscopic analysis of the unpurified reaction mixture indicated >20:1 dr; m.p. 53-55° C.; $^1$H NMR (600 MHz, CDCl$_3$) δ 5.87 (s, 1H), 4.14-4.04 (m, 1H), 2.83 (q, J=8.3, 7.7 Hz, 1H), 2.63 (dd, J=17.6, 10.3 Hz, 1H), 2.11-2.00 (m, 1H), 1.79 (dt, J=13.9, 7.8 Hz, 1H), 1.72-1.60 (m, 4H), 1.56-1.48 (m, 1H); $^{13}$C NMR (150 MHz, CDCl$_3$) δ 178.1, 59.1, 37.8, 37.3, 34.5, 34.3, 23.7; IR (cm$^{-1}$) 3221, 2953, 1683, 730; HRMS (EI) m/z calcd. for C$_7$H$_{11}$NO [M]$^+$: 125.0841, found: 125.0842.

[Example 34] Preparation of octahydro-3a,7:5,9-dimethanocycloocta[b]pyrrol-2(3H)-one (21)

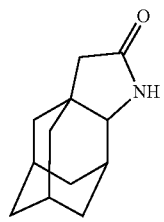 [SMILES: O=C1CC23CC4CC(CC(C4)C2N1)C3]

Using Catalyst K (5.9 mg, 5 mol %) and NaBAr$^F_4$ (8.8 mg, 5 mol %). White solid (35 mg, 91%); m.p. 161-163° C.; $^1$H NMR (600 MHz, CDCl$_3$) δ 5.70 (s, 1H), 3.47 (s, 1H), 2.11-2.01 (m, 3H), 1.93-1.87 (m, 3H), 1.84 (d, J=11.9 Hz, 2H), 1.80 (d, J=12.8 Hz, 1H), 1.76-1.70 (m, 3H), 1.67 (d, J=12.4 Hz, 1H), 1.61 (d, J=12.7 Hz, 1H), 1.42 (d, J=11.4 Hz, 1H); $^{13}$C NMR (150 MHz, CDCl$_3$) δ 178.9, 63.9, 46.2, 40.0, 38.5, 37.1, 37.0, 36.7, 29.5, 29.4, 28.9, 27.3; IR (cm$^{-1}$) 3172, 2910, 2851, 1682, 733; HRMS (EI) m/z calcd. for C$_{12}$H$_{17}$NO [M]$^+$: 191.1310, found: 191.1307.

[Example 35] Preparation of 4,4-dimethylpyrrolidin-2-one (22)

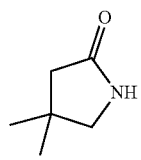

Using Catalyst K (5.9 mg, 5 mol %) and NaBAr$^F_4$ (8.8 mg, 5 mol %) in a solvent of hexafluoro-2-propanol (2.4 mL). Yellowish oil (7 mg, 31%); $^1$H NMR (600 MHz, CDCl$_3$) δ 6.04 (s, 1H), 3.11 (s, 2H), 2.14 (s, 2H), 1.17 (s, 6H); ¹³C NMR (150 MHz, CDCl₃) δ 178.0, 55.4, 45.2, 35.9, 27.7; IR (cm⁻¹) 3233, 2956, 2868, 1686, 1311, 1249; HRMS (FAB) m/z calcd. for C₆H₁₁NO [M+H]⁺: 114.0919, found: 114.0917.

[Example 36] Preparation of 5-vinylpyrrolidin-2-one (23)

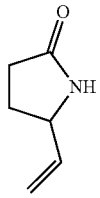

Using Catalyst K (11.8 mg, 10 mol %) and NaBAr$^F_4$ (17.7 mg, 10 mol %) Colorless resin (14 mg, 63%); ¹H NMR (600 MHz, CDCl₃) δ 6.40 (s, 1H), 5.79 (ddd, J=16.9, 10.2, 6.6 Hz, 1H), 5.21 (dd, J=16.9, 1.3 Hz, 1H), 5.11 (dd, J=10.3, 1.4 Hz, 1H), 4.15 (q, J=6.6 Hz, 1H), 2.42-2.26 (m, 3H), 1.88-1.77 (m, 1H); ¹³C NMR (150 MHz, CDCl₃) δ 178.4, 138.7, 115.7, 56.7, 29.8, 28.0.

[Example 37] Preparation of 5-(1-phenylvinyl)pyrrolidin-2-one (24)

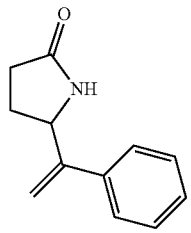

Catalyst J (11.8 mg, 10 mol %) and NaBAr$^F_4$ (17.7 mg, 10 mol %) were used. White solid (18 mg, 48%); m.p. 104-106° C.; ¹H NMR (600 MHz, CDCl₃) δ 7.37-7.30 (m, 5H), 6.56 (s, 1H), 5.35 (s, 1H), 5.28 (s, 1H), 4.70 (t, J=6.0 Hz, 1H), 2.42-2.29 (m, 3H), 1.84 (tt, J=10.2, 5.6 Hz, 1H); ¹³C NMR (150 MHz, CDCl₃) δ 178.6, 149.1, 138.9, 128.6, 128.0, 126.5, 111.5, 56.7, 29.4, 27.8; IR (cm⁻¹) 3203, 1684, 766, 700; HRMS (EI) m/z calcd. for C₁₂H₁₃NO [M]⁺: 187.0997, found: 187.0996.

[Example 38] Preparation of (E)-5-Styrylpyrrolidin-2-one (25)

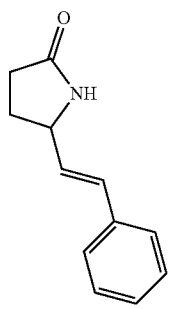 [SMILES: O=C1CCC(/C=C/c2ccccc2)N1]

Catalyst J (11.8 mg, 10 mol %) and NaBAr$^F_4$ (17.7 mg, 10 mol %) were used. White solid (33 mg, 88%); m.p. 101-103° C.; ¹H NMR (400 MHz, CDCl₃) δ 7.39-7.30 (m, 4H), 7.27 (t, J=7.4 Hz, 1H), 6.55 (d, J=15.8 Hz, 1H), 6.13 (dd, J=15.8, 7.4 Hz, 1H), 5.87 (s, 1H), 4.40-4.28 (m, 1H), 2.47-2.32 (m, 3H), 2.01-1.87 (m, 1H); ¹³C NMR (150 MHz, CDCl₃) δ 178.0, 136.0, 131.2, 129.8, 128.7, 128.0, 126.5, 56.4, 29.9, 28.5; IR (cm⁻¹) 3214, 3024, 1684, 965, 749, 692; HRMS (EI) m/z calcd. for C₁₂H₁₃NO [M]⁺: 187.0997, found: 187.0995.

[Example 39] Preparation of 5-(phenylethynyl)pyrrolidin-2-one (26)

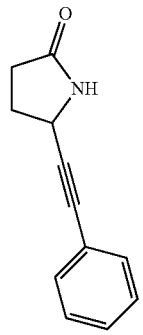 [SMILES: O=C1CCC(C#Cc2ccccc2)N1]

Catalyst J (11.8 mg, 10 mol %) and NaBAr$^F_4$ (17.7 mg, 10 mol %) were used. White solid (34 mg, 92%); m.p. 99-101° C.; ¹H NMR (600 MHz, CDCl₃) δ 7.41 (dd, J=7.7, 1.7 Hz, 2H), 7.34-7.29 (m, 3H), 5.84 (s, 1H), 4.62 (dd, J=7.5, 5.1 Hz, 1H), 2.57-2.50 (m, 2H), 2.40-2.34 (m, 1H), 2.34-2.27 (m, 1H); ¹³C NMR (150 MHz, CDCl₃) δ 177.3, 131.6, 128.6, 128.3, 122.1, 87.8, 84.1, 45.2, 29.4, 29.2; IR (cm⁻¹) 3176, 3066, 1693, 1335, 1257, 754; HRMS (EI) m/z calcd. for C₁₂H₁₁NO [M]⁺: 185.0841, found: 185.0838.

[Example 40] Preparation of 5-(3-phenylprop-1-yn-1-yl)pyrrolidin-2-one (27)

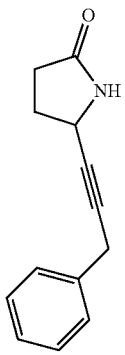 [SMILES: O=C1CCC(C#CCc2ccccc2)N1]

Catalyst J (11.8 mg, 10 mol %) and NaBAr$^F_4$ (17.7 mg, 10 mol %) were used. Yellow resin (30 mg, 75%); ¹H NMR (600 MHz, CDCl₃) δ 7.35-7.26 (m, 4H), 7.27-7.20 (m, 1H), 6.59 (s, 1H), 4.46-4.34 (m, 1H), 3.58 (s, 2H), 2.49-2.36 (m, 2H), 2.34-2.24 (m, 1H), 2.20-2.11 (m, 1H); ¹³C NMR (150 MHz, CDCl₃) δ 177.9, 136.3, 128.7, 127.9, 126.8, 82.2, 81.4, 45.2, 29.7, 29.4, 25.1; IR (cm⁻¹) 3229, 3028, 1685,

[Example 41] Preparation of 5-(prop-1-yn-1-yl)pyrrolidin-2-one (28)

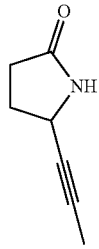

Catalyst J (11.8 mg, 10 mol %) and NaBAr$^F_4$ (17.7 mg, 10 mol %) were used. White solid (15 mg, 61%); m.p. 77-79° C.; $^1$H NMR (600 MHz, CDCl$_3$) δ 6.23 (s, 1H), 4.36-4.28 (m, 1H), 2.49-2.34 (m, 2H), 2.34-2.24 (m, 1H), 2.16-2.06 (m, 1H), 1.80 (s, 3H); $^{13}$C NMR (150 MHz, CDCl$_3$) δ 177.8, 80.4, 78.3, 45.2, 29.7, 29.4, 3.6; IR (cm$^{-1}$) 3165, 3075, 1688, 1257, 777, 675, 495; HRMS (EI) m/z calcd. for C$_7$H$_9$NO [M]$^+$: 123.0684, found: 123.0685.

[Example 42] Preparation of trans-4-Ethyl-5-phenylpyrrolidin-2-one (29)

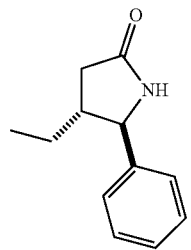

Catalyst J (2.4 mg, 2 mol %) was used. White solid (34 mg, 90%); >20:1 d.r. and 12.6:1 r.r. were confirmed by $^1$H NMR spectroscopy; m.p. 131-133° C.; $^1$H NMR (400 MHz, CDCl$_3$) δ 7.39-7.32 (m, 2H), 7.32-7.27 (m, 3H), 6.46 (s, 1H), 4.28 (d, J=6.7 Hz, 1H), 2.69-2.49 (m, 1H), 2.17-2.06 (m, 2H), 1.74-1.58 (m, 1H), 1.50-1.35 (m, 1H), 0.89 (t, J=7.4 Hz, 3H); $^{13}$C NMR (100 MHz, CDCl$_3$) δ 177.6, 141.6, 128.7, 127.9, 126.2, 64.1, 47.0, 36.4, 26.0, 11.9; IR (cm$^{-1}$) 3211, 2959, 1690, 1455, 1282, 755, 699; HRMS (FAB) m/z calcd. for C$_{12}$H$_{15}$NO [M+H]$^+$: 190.1232, found: 190.1230.

[Example 43] Preparation of 4-benzyl-5,5-dimethylpyrrolidin-2-one (30-A)/trans-4-Isopropyl-5-phenylpyrrolidin-2-one (30-B)

Catalyst J (2.4 mg, 2 mol %) was used. Combined isolated yield: 96% (39 mg). 1.3:1 r.r was confirmed by $^1$H NMR spectroscopy.

4-Benzyl-5,5-dimethylpyrrolidin-2-one (30-A)

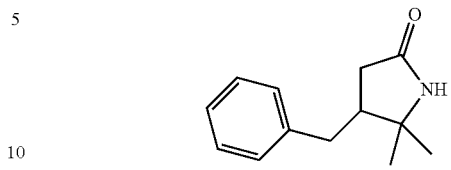

Major Regioisomer:
White solid (22 mg); m.p. 124-126° C.; $^1$H NMR (400 MHz, CDCl$_3$) δ 7.29 (t, J=7.4 Hz, 2H), 7.21 (t, J=7.3 Hz, 1H), 7.16 (d, J=7.2 Hz, 2H), 6.66 (s, 1H), 2.81 (dd, J=13.3, 4.6 Hz, 1H), 2.52 (dd, J=13.2, 10.6 Hz, 1H), 2.43-2.33 (m, 1H), 2.28-2.12 (m, 2H), 1.26 (s, 3H), 1.22 (s, 3H); $^{13}$C NMR (150 MHz, CDCl$_3$) δ 176.0, 139.7, 128.6, 128.6, 126.3, 58.8, 47.5, 36.5, 35.9, 28.4, 23.5; IR (cm$^{-1}$) 3217, 2966, 1691; HRMS (FAB) m/z calcd. for C$_{13}$H$_{17}$NO [M+H]$^+$: 204.1388, found: 204.1387.

trans-4-Isopropyl-5-phenylpyrrolidin-2-one (30-B)

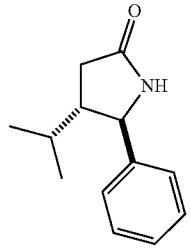

Minor Regioisomer:
Colorless oil (17 mg); >20:1 d.r. was confirmed by $^1$H NMR spectroscopy; $^1$H NMR (400 MHz, CDCl$_3$) δ 7.43-7.33 (m, 2H), 7.32-7.26 (m, 3H), 6.17 (s, 1H), 4.43 (d, J=5.7 Hz, 1H), 2.55-2.44 (m, 1H), 2.25-2.16 (m, 2H), 1.85-1.75 (m, 1H), 0.96 (d, J=6.7 Hz, 3H), 0.86 (d, J=6.8 Hz, 3H); $^{13}$C NMR (100 MHz, CDCl$_3$) δ 177.4, 142.4, 128.8, 127.9, 126.4, 61.7, 50.8, 33.0, 30.1, 20.8, 18.8; IR (cm$^{-1}$) 3209, 2957, 1694, 700; HRMS (FAB) m/z calcd. for C$_{13}$H$_{17}$NO [M+H]$^+$: 204.1388, found: 204.1389.

[Example 44] Preparation of (S)-2-(5,5-dimethyl-2-oxopyrrolidin-3-yl)isoindoline-1,3-dione (31)

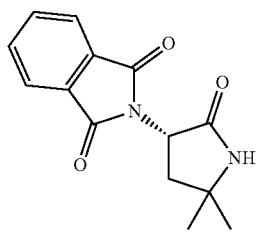 [SMILES: CC1(C)C[C@H](N2C(=O)c3ccccc3C2=O)C(=O)N1]

Using Catalyst K (5.9 mg, 5 mol %) and NaBAr$^F_4$ (8.8 mg, 5 mol %). White solid (29 mg, 56%); m.p. 217-219° C.; $^1$H NMR (400 MHz, CDCl$_3$) δ 7.85 (dd, J=5.4, 3.1 Hz, 2H), 7.72 (dd, J=5.5, 3.1 Hz, 2H), 5.86 (s, 1H), 5.13-5.05 (m, 1H), 2.44 (t, J=11.6 Hz, 1H), 2.33 (dd, J=12.4, 9.3 Hz, 1H), 1.47 (s, 3H), 1.38 (s, 3H); $^{13}$C NMR (150 MHz, CDCl$_3$) δ 170.6, 167.5, 134.1, 131.9, 123.5, 53.6, 49.7, 39.5, 29.9, 29.3; IR (cm$^{-1}$) 3180, 3087, 1701, 1387, 716; HRMS (EI) m/z calcd. for C$_{14}$H$_{14}$N$_2$O$_3$ [M]$^+$: 258.1004, found: 258.1007; Optical Rotation: [a]$^{28}_D$=−60 (c=1.0, CHCl$_3$); HPLC Analysis (250 mm CHIRALPAK AD-H column, 20% i-PrOH/hexanes, 0.8 mL/min, 254 nm, 25° C.) indicated 99% ee: $t_R$(major)=35.2 min, $t_R$ (minor)=11.1 min.

[Example 45] Preparation of 2-((3S,5S)-2-oxo-5-phenylpyrrolidin-3-yl)isoindoline-1,3-dione (32)

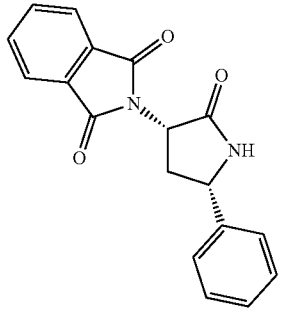 [SMILES: O=C1N[C@H](c2ccccc2)C[C@@H]1N1C(=O)c2ccccc2C1=O]

Using Catalyst K (5.9 mg, 5 mol %) and NaBAr$^F_4$ (8.8 mg, 5 mol %). White solid (29 mg, 48%); $^1$H NMR spectroscopic analysis of the unpurified reaction mixture indicated 10:1 dr; m.p. 260-262° C.; $^1$H NMR (600 MHz, CDCl$_3$) δ 7.89-7.81 (m, 2H), 7.76-7.70 (m, 2H), 7.53 (d, J=7.4 Hz, 2H), 7.41 (t, J=7.6 Hz, 2H), 7.34 (t, J=7.5 Hz, 1H), 6.28 (s, 1H), 5.09 (t, J=10.3 Hz, 1H), 4.74 (t, J=8.1 Hz, 1H), 2.90-2.80 (m, 1H), 2.61-2.45 (m, 1H); $^{13}$C NMR (150 MHz, CDCl$_3$) δ 172.0, 167.6, 141.2, 134.4, 132.1, 129.2, 128.7, 126.8, 123.7, 55.2, 50.2, 36.3; IR (cm$^{-1}$) 3356, 2923, 1710, 1390, 718; HRMS (EI) m/z calcd. for C$_{18}$H$_{14}$N$_2$O$_3$ [M]$^+$: 306.1004, found: 306.1007; Optical Rotation: [a]$^{28}_D$=−34 (c=1.0, CHCl$_3$); HPLC Analysis (250 mm CHIRALPAK AD-H column, 20% i-PrOH/hexanes, 0.8 mL/min, 254 nm, 25° C.) indicated 98% ee: $t_R$ (major)=41.8 min, $t_R$ (minor)=27.7 min.

[Example 46] Preparation of (R)-2-(2,2-dimethyl-5-oxopyrrolidin-3-yl)isoindoline-1,3-dione (33)

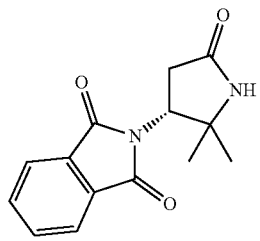 [SMILES: CC1(C)NC(=O)C[C@H]1N1C(=O)c2ccccc2C1=O]

Using Catalyst K (5.9 mg, 5 mol %) and NaBAr$^F_4$ (8.8 mg, 5 mol %). White solid (28 mg, 55%); m.p. 172-174° C.; $^1$H NMR (600 MHz, CDCl$_3$) δ 7.85 (dd, J=5.5, 3.1 Hz, 2H), 7.74 (dd, J=5.5, 3.1 Hz, 2H), 6.84 (s, 1H), 4.73 (dd, J=9.4, 5.9 Hz, 1H), 3.32 (dd, J=17.2, 5.9 Hz, 1H), 2.75 (dd, J=17.2, 9.4 Hz, 1H), 1.42 (s, 3H), 1.20 (s, 3H); $^{13}$C NMR (150 MHz, CDCl$_3$) δ 174.2, 168.4, 134.5, 131.6, 123.7, 60.2, 55.3, 33.0, 29.6, 24.1; IR (cm$^{-1}$) 2962, 1830, 1710, 1371, 712; HRMS (EI) m/z calcd. for C$_{14}$H$_{14}$N$_2$O$_3$ [M]$^+$: 258.1004, found: 258.1005; Optical Rotation: [a]$^{28}_D$=33 (c=1.0, CHCl$_3$); HPLC Analysis (250 mm CHIRALCEL OD-H column, 20% i-PrOH/hexanes, 0.8 mL/min, 254 nm, 25° C.) indicated 99% ee: $t_R$ (major)=31.0 min, $t_R$ (minor)=24.8 min.

[Example 47] Preparation of 2-((2-oxooctahydro-3aH-indol-3a-yl)methyl)isoindoline-1,3-dione (34)

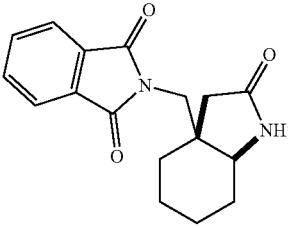

Using Catalyst K (5.9 mg, 5 mol %) and NaBAr$^F_4$ (8.8 mg, 5 mol %). White solid (53 mg, 88%); m.p. 174-176° C.; $^1$H NMR (400 MHz, CDCl$_3$) δ 7.86 (dd, J=5.5, 3.1, 2H), 7.75 (dd, J=5.5, 3.1 Hz, 2H), 5.52 (s, 1H), 3.79 (d, J=0.8 Hz, 2H), 3.58 (t, J=4.0 Hz, 1H), 2.48 (d, J=16.4, 1H), 2.03 (d, J=16.4 Hz, 1H), 1.94-1.82 (m, 1H), 1.72-1.64 (m, 1H), 1.60-1.42 (m, 6H); $^{13}$C NMR (100 MHz, CDCl$_3$) δ 176.7, 169.0, 134.4, 131.9, 123.7, 55.5, 43.2, 43.1, 42.6, 30.8, 26.5, 21.2, 20.0; IR (cm$^{-1}$) 3218, 2931, 1772, 1708, 1394, 724; HRMS (EI) m/z calcd. for C$_{17}$H$_{18}$N$_2$O$_3$ [M]$^+$: 298.1317, found: 298.1318.

[Example 48] Preparation of cis-tert-butyl {(2-oxooctahydro-3aH-indol-3a-yl)methyl}carbamate (35)

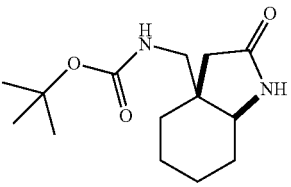

Using Catalyst K (5.9 mg, 5 mol %) and NaBAr$^F_4$ (8.8 mg, 5 mol %) in a solvent of hexafluoro-2-propanol (2.4 mL); Beige solid (24 mg, 45%); m.p. 62-64° C.; $^1$H NMR (400 MHz, CDCl$_3$) δ5.96 (s, 1H), 4.72 (s, 1H), 3.46 (t, J=3.8 Hz, 1H), 3.31-3.09 (m, 2H), 2.24 (d, J=16.2 Hz, 1H), 1.99 (d, J=16.2 Hz, 1H), 1.76-1.54 (m, 2H), 1.53-1.34 (m, 15H); $^{13}$C NMR (100 MHz, CDCl$_3$) δ177.0, 156.2, 79.6, 55.3, 45.0, 42.4, 42.0, 30.0, 28.3, 26.8, 21.0, 20.0; IR (cm$^{-1}$) 3279, 2929, 1681, 1526, 1365, 1249, 1166, 1008, 918, 730; HRMS (FAB) m/z calcd. for C$_{14}$H$_{24}$N$_2$O$_3$ [M+H]$^+$: 269.1865, found: 269.1862.

[Example 49] Preparation of tert-butyl 2-methyl-5-oxopyrrolidine-1-carboxylate (36)

5-Methylpyrrolidin-2-one was separated by one-pot Boc-protection and then prepared.

The catalytic reaction mixture of 3-butyl-1,4,2-dioxazol-5-one was cooled to room temperature, di-tert-butyl dicarbonate (Boc₂O, 91.9 μL 0.4 mmol), 4-(dimethylamino)pyridine (DMAP, 24.4 mg, 0.2 mmol), and triethylamine (27.8 μL, 0.2 mmol) were added thereto and the mixture was vigorously stirred at room temperature for 12 hours. The reaction mixture was filtered with celite, washed with dichloromethane (10 mL×4), and concentrated under reduced pressure to obtain a residue, which was separated and purified by column chromatography (eluent: n-hexane/EtOAc, 2:1~1:2) to obtain the desired compound.

The compound prepared by the above method is shown in the following.

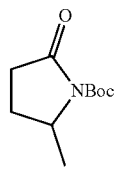

Yellowish oil (22 mg, 55%); ¹H NMR (600 MHz, CDCl₃) δ 4.28-4.18 (m, 1H), 2.60 (dt, J=19.8, 10.0 Hz, 1H), 2.42 (ddd, J=17.6, 9.4, 2.7 Hz, 1H), 2.16 (dt, J=20.6, 9.9 Hz, 1H), 1.66-1.61 (m, 1H), 1.52 (s, 9H), 1.31 (d, J=6.3 Hz, 3H); ¹³C NMR (150 MHz, CDCl₃) δ 174.2, 149.9, 82.6, 54.0, 31.3, 28.0, 25.2, 20.2.

[Examples 50 to 58, and Comparative Examples 3 to 7] Preparation of Gamma-Lactam Compound

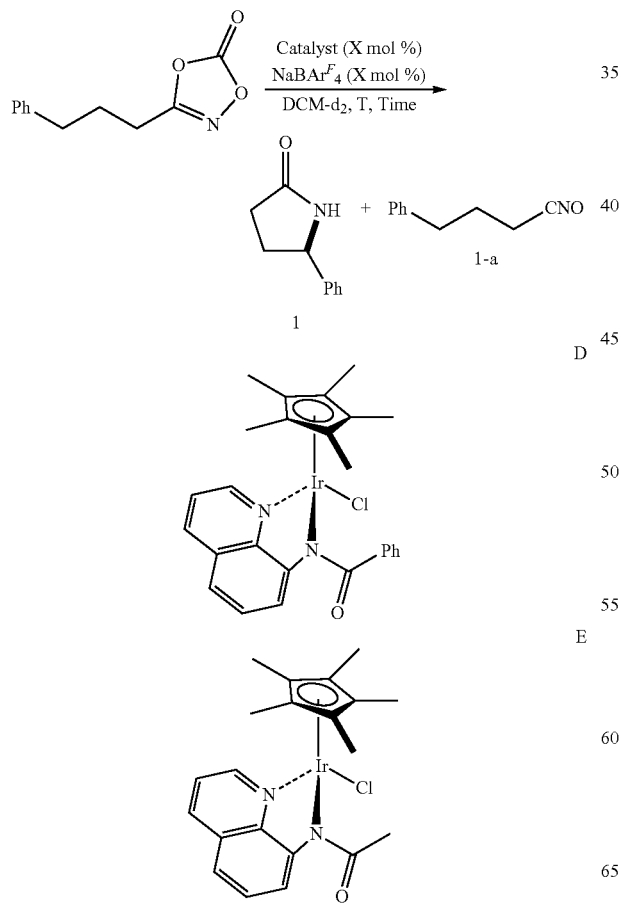

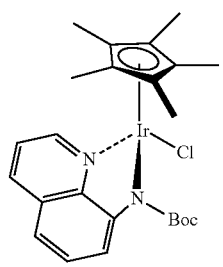

F

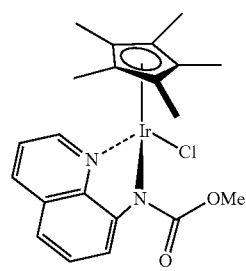

G

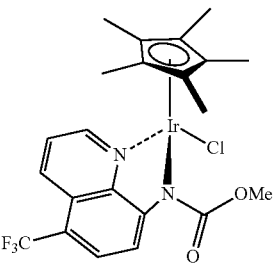

I

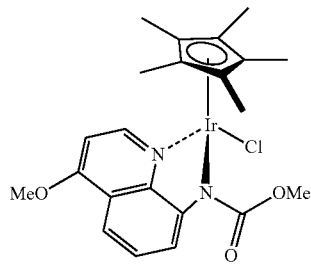

J

K

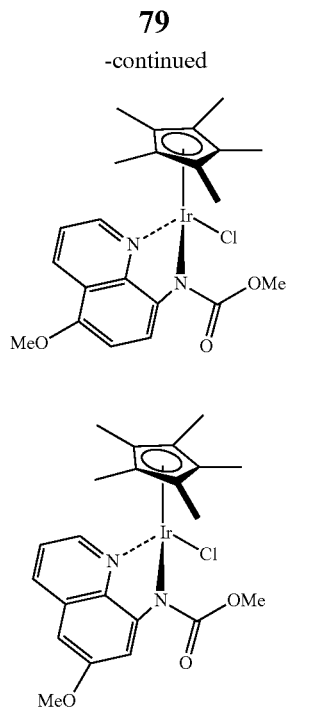

L

A

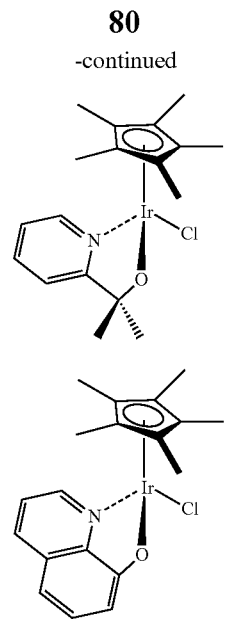

B

A gamma-lactam compound was prepared in the same manner as in Example 19, except that the catalyst and time were different as shown in Table 1, and the results are shown in Table 1.

TABLE 1

| | Catalyst (mol %) | NaBAr$^F_4$ (mol %) | Reaction temperature, T (° C.) | Reaction time (h) | Yield (%) of gamma-lactam compound (1) | Yield of Compound 1-a | Mole ratio of 1:1-a |
|---|---|---|---|---|---|---|---|
| Example 50 | Complex D (10 mol %) | NaBAr$^F_4$ (10 mol %) | rt | 18 | 73 | 14 | 5.2:1 |
| Example 51 | Complex E (10 mol %) | NaBAr$^F_4$ (10 mol %) | rt | 18 | 81 | 17 | 4.8:1 |
| Example 52 | Complex F (10 mol %) | NaBAr$^F_4$ (10 mol %) | rt | 12 | 86 | 13 | 6.2:1 |
| Example 53 | Complex G (10 mol %) | NaBAr$^F_4$ (10 mol %) | rt | 12 | 90 | 9 | 9.8:1 |
| Example 54 | Complex I (10 mol %) | NaBAr$^F_4$ (10 mol %) | rt | 24 | 80 | 8 | 9.5:1 |
| Example 55 | Complex J (10 mol %) | NaBAr$^F_4$ (10 mol %) | rt | 2 | 97 | <5 | >20:1 |
| Example 56 | Complex K (10 mol %) | NaBAr$^F_4$ (10 mol %) | rt | 6 | 98 | <5 | >20:1 |
| Example 57 | Complex L (10 mol %) | NaBAr$^F_4$ (10 mol %) | rt | 6 | 98 | <5 | >20:1 |
| Example 58 | Complex J (2 mol %) | NaBAr$^F_4$ (2 mol %) | rt | 12 | 94 | <5 | >20:1 |
| Comparative Example 3 | Complex A (10 mol %) | NaBAr$^F_4$ (10 mol %) | 60 | 12 | 39 | 17 | 2.3:1 |
| Comparative Example 4 | Complex B (10 mol %) | NaBAr$^F_4$ (10 mol %) | 40 | 18 | 73 | 15 | 4.8:1 |
| Comparative Example 5 | Rh$_2$(OAc)$_4$[b] (5 mol %) | — | 40 | 12 | <5 | <5 | — |
| Comparative Example 6 | Rh$_2$(esp)$_2$[b] (5 mol %) | — | 40 | 12 | <5 | <5 | — |

TABLE 1-continued

| | Catalyst (mol %) | NaBAr$^F_4$ (mol %) | Reaction temperature, T (° C.) | Reaction time (h) | Yield (%) of gamma-lactam compound (1) | Yield of Compound 1-a | Mole ratio of 1:1-a |
|---|---|---|---|---|---|---|---|
| Comparative Example 7 | Ru(TPP)CO[b] (5 mol %) | NaBAr$^F_4$ (5 mol %) | 40 | 12 | <5 | 35 | — | rt: room temperature,
[b]The catalyst of Comparative Example 5-7 was purchased from Aldrich and TCI.

As shown in Table 1 above, the catalyst which is the metal complex having a specific ligand of the present invention produced a lactam compound with surprisingly excellent selectivity and yield as compared with the catalysts of Comparative Examples 3 to 7.

Furthermore, with the metal catalyst of the present invention, the reaction is performed under mild conditions and simultaneously, a gamma-lactam compound may be obtained with a high yield and excellent selectivity, and the method of preparing a gamma-lactam compound of the present invention may be very usefully applied to a raw material and an intermediate such as various natural products and medicines.

Example III: Application of Method of Preparing Gamma-Lactam Compound of the Present Invention

[Example 59] Preparation of (Z)-6a-(pent-2-en-1-yl)hexahydrocyclopenta[b]pyrrole-2,6-dione

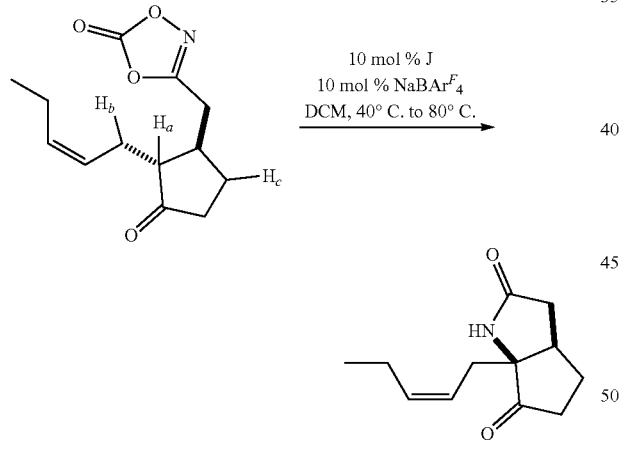

(Z)-6a-(Pent-2-en-1-yl)hexahydrocyclopenta[b]pyrrole-2,6-dione was prepared in the same manner as in Example 19, except that the starting material was different.

Preparation was performed by stirring at 40° C. for 12 hours and stirring again at 80° C. for 12 hours, using Catalyst J (11.8 mg, 10 mol %) and NaBAr$^F_4$ (17.7 mg, 10 mol %). Colorless oil (29 mg, 70%) $^1$H NMR (400 MHz, CDCl$_3$) δ 5.69 (s, 1H), 5.62 (dt, J=10.9, 7.4 Hz, 1H), 5.35-5.18 (m, 1H), 2.82-2.62 (m, 2H), 2.52 (ddd, J=18.1, 8.1, 4.5 Hz, 1H), 2.41-2.15 (m, 5H), 2.05 (p, J=7.7 Hz, 2H), 1.76-1.63 (m, 1H), 0.97 (t, J=7.5 Hz, 3H); $^{13}$C NMR (150 MHz, CDCl$_3$) δ 214.9, 175.8, 137.2, 120.2, 67.9, 38.9, 37.2, 36.9, 32.2, 26.0, 20.7, 14.0; IR (cm$^{-1}$) 3214, 2961, 2932, 2872, 1739, 1686; HRMS (EI) m/z calcd. for C$_{12}$H$_{17}$NO$_2$ [M]$^+$: 207.1259, found: 207.1258.

[Example 60] Preparation of (5S)-5-((3R,5R,9S,10S,13S,14S)-3-methoxy-10,13-dimethylhexadecahydro-1H-cyclopenta[a]phenanthren-17-yl)-5-methylpyrrolidin-2-one

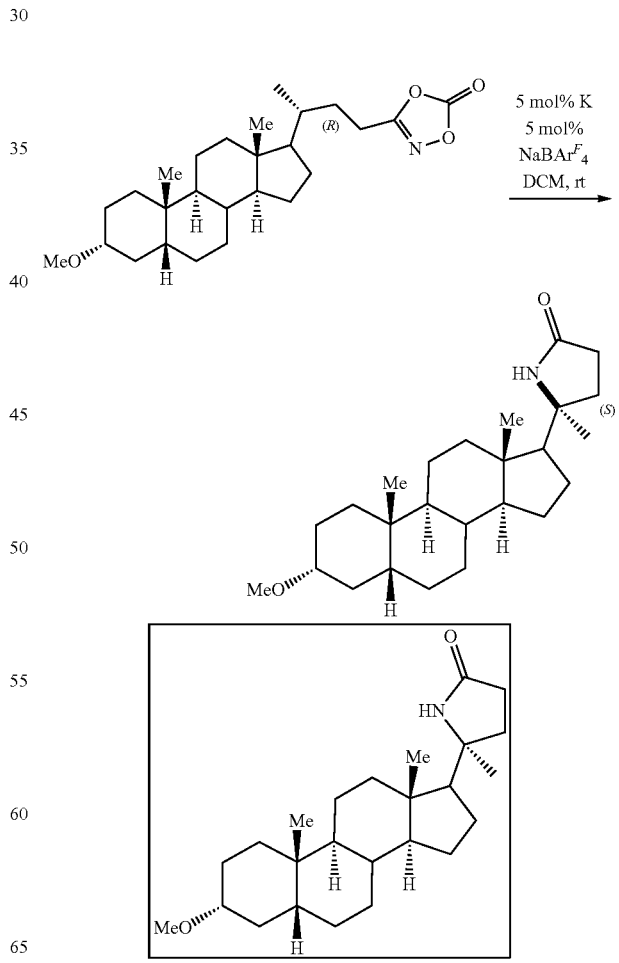

Prepared with Catalyst K (5.9 mg, 5 mol %) and NaBAr$^F_4$ (8.8 mg, 5 mol %). White solid (26 mg, 32%); m.p. 231-233° C.; $^1$H NMR (600 MHz, CDCl$_3$) δ 5.57 (s, 1H), 3.35 (s, 3H), 3.16 (tt, J=10.5, 4.6 Hz, 1H), 2.37 (dt, J=18.1, 8.8 Hz, 1H), 2.31-2.21 (m, 1H), 2.12-1.98 (m, 2H), 1.90-1.81 (m, 1H), 1.80-1.54 (m, 10H), 1.36 (d, J=21.9 Hz, 7H), 1.29-1.16 (m, 4H), 1.14-1.02 (m, 3H), 0.98-0.85 (m, 4H), 0.73 (s, 3H); $^{13}$C NMR (150 MHz, CDCl$_3$, one carbon merged to others) δ 177.6, 80.3, 61.7, 59.6, 56.3, 55.6, 43.5, 41.9, 40.2, 35.3, 35.2, 34.8, 34.8, 32.7, 29.1, 28.7, 27.2, 26.8, 26.2, 23.7, 23.3, 23.0, 20.5, 13.6; IR (cm$^{-1}$) 3230, 2925, 2862, 1689, 1448, 1369, 1098; HRMS (EI) m/z calcd. for C$_{25}$H$_{41}$NO$_2$ [M]$^+$: 387.3137, found: 387.3139.

[Example 61] Preparation of (±)-trans-4-Methyl-5-(3-methylbut-2-en-1-yl)pyrrolidin-2-one

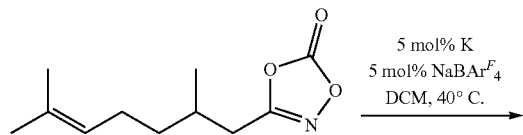

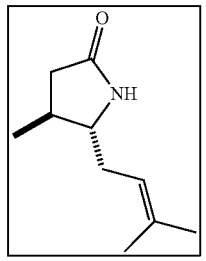

Prepared with Catalyst K (5.9 mg, 5 mol %) and NaBAr$^F_4$ (8.8 mg, 5 mol %). Colorless oil (15 mg, 45%); $^1$H NMR spectroscopic analysis of the unpurified reaction mixture indicated 3.4:1 dr; major isomer (anti diastereomer); $^1$H NMR (400 MHz, CDCl$_3$) δ 5.68 (s, 1H), 5.08 (t, J=7.9 Hz, 1H), 3.18 (dt, J=8.3, 5.7 Hz, 1H), 2.51 (dd, J=16.6, 8.3 Hz, 1H), 2.30-2.18 (m, 1H), 2.17-2.07 (m, 2H), 1.99 (dt, J=16.5, 8.0 Hz, 1H), 1.71 (s, 3H), 1.62 (s, 3H), 1.12 (d, J=6.7 Hz, 3H); $^{13}$C NMR (150 MHz, CDCl$_3$) δ 176.9, 135.4, 119.4, 61.9, 38.8, 35.4, 33.8, 25.8, 18.9, 18.0; IR (cm$^{-1}$) 3213, 2961, 2923, 1686, 1376; HRMS (EI) m/z calcd. for C$_{10}$H$_{17}$NO [M]$^+$: 167.1310, found: 167.1312.

[Example 62] Preparation of (3S,3aS,5aS,9bR)-3,5a,9-Trimethyl-1,3a,4,5,5a,9b-hexahydro-2H-benzo[g]indole-2,8 (3H)-dione

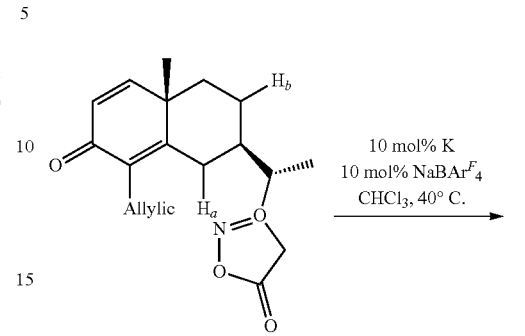

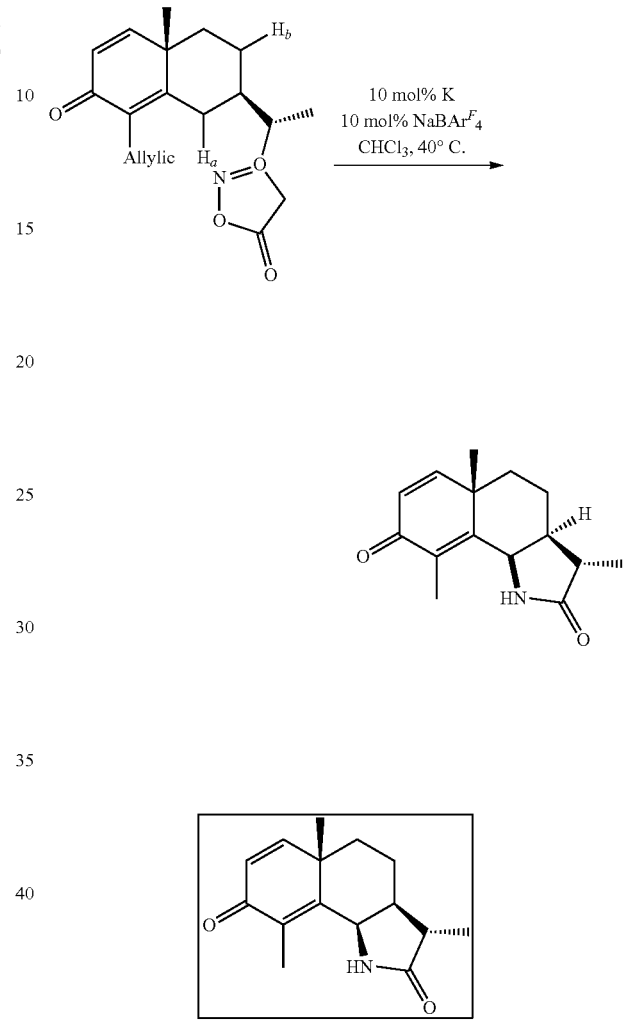

Prepared with Catalyst K (11.8 mg, 10 mol %), NaBAr$^F_4$ (17.7 mg, 10 mol %), and chloroform (2.4 mL) as a solvent. White solid (21 mg, 43%); $^1$H NMR spectroscopic analysis of the unpurified reaction mixture indicated >20:1 dr; m.p. 299-301° C.; $^1$H NMR (600 MHz, CDCl$_3$) 6.73 (d, J=9.8 Hz, 1H), 6.24 (d, J=9.8 Hz, 1H), 5.50 (s, 1H), 4.90 (d, J=5.5 Hz, 1H), 2.32-2.25 (m, 1H), 2.14-2.07 (m, 1H), 2.02 (s, 3H), 1.84-1.79 (m, 2H), 1.78-1.70 (m, 1H), 1.49-1.38 (m, 1H), 1.33 (s, 3H), 1.30 (d, J=7.5 Hz, 3H); $^{13}$C NMR (150 MHz, CDCl$_3$) δ 186.1, 180.8, 157.6, 151.6, 135.9, 125.9, 52.8, 44.9, 43.6, 39.6, 34.8, 25.7, 23.6, 15.0, 11.2; IR (cm$^{-1}$) 3181, 2948, 1696, 1651, 1624, 1271, 853, 769; HRMS (EI) m/z calcd. for C$_{15}$H$_{19}$NO$_2$ [M]$^+$: 245.1416, found: 245.1417.

As seen from Examples 59 to 62, it was found that the method of preparing a gamma-lactam compound from a dioxazol-one compound which was an intentionally selected starting material, using the metal complex of the present invention as a catalyst may be very useful in preparation of an intermediate and a raw material of synthesis of medicines, natural materials, and the like.

The invention claimed is:

1. A metal complex represented by the following Chemical Formula 1:

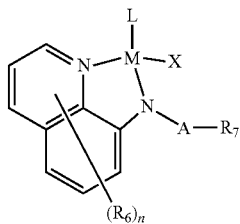

Chemical Formula 1 wherein
M is iridium, rhodium, ruthenium, or cobalt;
L is

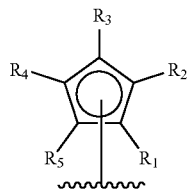

wherein each of $R_1$, $R_2$, $R_3$, $R_4$ and $R_5$ is independently of one another (C1-C20)alkyl;
X is Cl or Br;
$R_6$ is halo(C1-C20)alkyl or (C1-C20)alkoxy;
A is —CO— or —SO$_2$—;
$R_7$ is (C1-C20)alkyl, (C1-C20)alkoxy, (C6-C20)aryl, (C1-C20)alkyl(C6-C20)aryl, or —NR$_{11}$R$_{12}$;
$R_{11}$ and $R_{12}$ are independently of each other hydrogen or (C1-C20)alkyl; and
n is an integer of 0 to 6.

2. The metal complex of claim 1, wherein Chemical Formula 1 is represented by the following Chemical Formula 2:

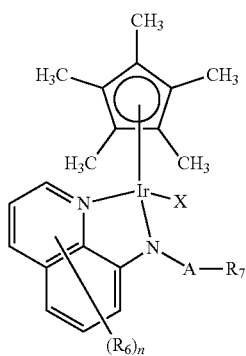

Chemical Formula 2 wherein
X is Cl or Br;
$R_6$ is halo(C1-C20)alkyl or (C1-C20)alkoxy;
A is —CO— or —SO$_2$—;
$R_7$ is (C1-C20)alkyl, (C1-C20)alkoxy, (C6-C20)aryl, (C1-C20)alkyl(C6-C20)aryl, or —NR$_{11}$R$_{12}$;
$R_{11}$ and $R_{12}$ are independently of each other hydrogen or (C1-C20)alkyl; and
n is an integer of 0 or 1.

3. The metal complex of claim 2, wherein A is —CO—, $R_6$ and $R_7$ are independently of each other (C1-C20)alkoxy, and n is an integer of 1.

4. A method of preparing a metal complex represented by the following Chemical Formula 1, the method comprising: reacting a metal precursor compound of the following Chemical Formula 3A and a quinoline-based compound of the following Chemical Formula 3B in the presence of a base to prepare the metal complex of the following Chemical Formula 1:

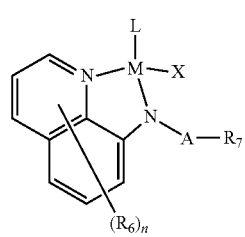

Chemical Formula 1

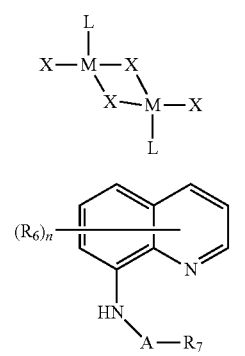

Chemical Formula 3A

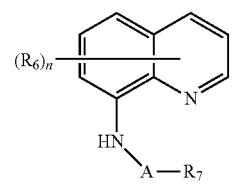

Chemical Formula 3B wherein
M is iridium, rhodium, ruthenium, or cobalt;
L is

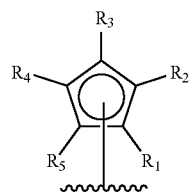

wherein each of $R_1$, $R_2$, $R_3$, $R_4$ and $R_6$ is independently of one another hydrogen or (C1-C20)alkyl;
X is Cl or Br;
$R_6$ is halo(C1-C20)alkyl or (C1-C20)alkoxy;
A is —CO— or —SO$_2$—;
$R_7$ is (C1-C20)alkyl, (C1-C20)alkoxy, (C6-C20)aryl, (C1-C20)alkyl(C6-C20)aryl, or —NR$_{11}$R$_{12}$;
$R_{11}$ and $R_{12}$ are independently of each other hydrogen or (C1-C20)alkyl; and
n is an integer of 0 to 6.

5. The method of preparing a metal complex of claim 4, wherein the base is any one or two or more selected from NaOAc, Na$_2$CO$_3$, NaHNO$_3$, Cu(OAc)$_2$, Cu(OAc)$_2$.H$_2$O, and NEt$_3$.

6. The method of preparing a metal complex of claim 4, wherein the base is used at 2 to 10 mol with respect to 1 mol of the metal precursor compound of Chemical Formula 3A, and the quinoline-based compound of Chemical Formula 3B is used at 1.5 to 2.5 mol with respect to 1 mol of the metal precursor compound of Chemical Formula 3A.

* * * * *